United States Patent
Gross et al.

(10) Patent No.: US 11,071,628 B2
(45) Date of Patent: Jul. 27, 2021

(54) LEAFLET-RESTRAINING TECHNIQUES

(71) Applicant: Valtech Cardio, Ltd., Or Yehuda (IL)

(72) Inventors: Amir Gross, Tel Aviv-Jaffa (IL); Tai Reich, Moledet (IL); Yaron Herman, Givat Ada (IL); Ehud Iflah, Tel Aviv-Jaffa (IL); Haim Brauon, Beit Dagan (IL); Meir Kutzik, Holon (IL); Meni Iamberger, Kfar Saba (IL)

(73) Assignee: Valtech Cardio, Ltd., Or Yehuda (IL)

( * ) Notice: Subject to any disclaimer, the term of this patent is extended or adjusted under 35 U.S.C. 154(b) by 134 days.

(21) Appl. No.: 16/254,518

(22) Filed: Jan. 22, 2019

(65) Prior Publication Data
US 2019/0151090 A1 May 23, 2019

Related U.S. Application Data

(63) Continuation of application No. 15/519,520, filed as application No. PCT/IL2015/051027 on Oct. 14, 2015, now Pat. No. 10,195,030.
(Continued)

(51) Int. Cl.
*A61F 2/24* (2006.01)
*A61B 17/068* (2006.01)
(Continued)

(52) U.S. Cl.
CPC .......... *A61F 2/2454* (2013.01); *A61B 17/068* (2013.01); *A61F 2/2445* (2013.01);
(Continued)

(58) Field of Classification Search
CPC .......... A61B 17/068; A61B 2017/0647; A61B 2017/0649; A61F 2/2445; A61F 2/2451;
(Continued)

(56) References Cited

U.S. PATENT DOCUMENTS

| 3,604,488 A | 9/1971 | Wishart et al. |
|---|---|---|
| 3,656,185 A | 4/1972 | Carpentier |

(Continued)

FOREIGN PATENT DOCUMENTS

| EP | 1034753 A1 | 9/2000 |
|---|---|---|
| EP | 3531975 A1 | 9/2019 |

(Continued)

OTHER PUBLICATIONS

Agarwal et al. International Cardiology Perspective Functional Tricuspid Regurgitation, Circ Cardiovasc Interv 2009;2;2;565-573 (2009).
(Continued)

*Primary Examiner* — Jocelin C Tanner
(74) *Attorney, Agent, or Firm* — Thomas C. Richardson

(57) ABSTRACT

A linking member extends from a first linking site of a longitudinal member to a second linking site of the longitudinal member. An anchor driver is configured to anchor portions of the longitudinal member to tissue using tissue anchors. A distal portion is anchorable to a first tissue location while the first linking site is within a catheter. While the distal portion is anchored to the first location, and the second linking site is within the catheter, a second portion is advanceable distally out of the catheter and is anchorable to a second tissue location. While the second portion is anchored to the second location, the second linking site and a third portion are advanceable distally out of the catheter. After the second linking site has been advanced out of the catheter, the third portion is anchorable to a third tissue location. Other embodiments are also described.

19 Claims, 30 Drawing Sheets

Related U.S. Application Data

(60) Provisional application No. 62/063,468, filed on Oct. 14, 2014.

(51) Int. Cl.
*A61B 17/00* (2006.01)
*A61B 17/064* (2006.01)

(52) U.S. Cl.
CPC .......... *A61F 2/2451* (2013.01); *A61F 2/2457* (2013.01); *A61F 2/2466* (2013.01); *A61B 2017/00292* (2013.01); *A61B 2017/0647* (2013.01); *A61B 2017/0649* (2013.01); *A61F 2220/0016* (2013.01)

(58) Field of Classification Search
CPC .... A61F 2/2454; A61F 2/2457; A61F 2/2466; A61F 2220/0016
See application file for complete search history.

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Ferrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,782,844 A | 7/1998 | Yoon et al. |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,202,315 B1 | 3/2001 | Schmick, Jr. |
| 6,210,347 B1 | 4/2001 | Forsell |
| 6,217,610 B1 | 4/2001 | Carpenter et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,343,174 B1 | 1/2002 | Neuberger |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy |
| 6,406,493 B1 | 6/2002 | Tu et al. |
| 6,419,696 B1 | 7/2002 | Ortiz et al. |
| 6,449,573 B1 | 9/2002 | Amos |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Farodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |
| 6,689,125 B1 | 2/2004 | Keith et al. |

(56) References Cited

U.S. PATENT DOCUMENTS

| | | |
|---|---|---|
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,730,121 B2 | 5/2004 | Ortiz et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Flinchbaugh |
| 6,858,039 B2 | 2/2005 | McCarthy |
| 6,870,949 B2 | 3/2005 | Baldwin |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,964,684 B2 | 11/2005 | Ortiz et al. |
| 6,964,686 B2 | 11/2005 | Gordon |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kirriblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,087,064 B1 | 6/2006 | Hyde |
| 7,077,850 B2 | 7/2006 | Kortenbach |
| 7,077,862 B2 | 7/2006 | Vidlund et al. |
| 7,101,395 B2 | 9/2006 | Trernulis et al. |
| 7,101,396 B2 | 9/2006 | Arthf et al. |
| 7,112,207 B2 | 9/2006 | Alien et al. |
| 7,118,595 B2 | 10/2006 | Ryan et al. |
| 7,125,421 B2 | 10/2006 | Trernulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Weber et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,326 B2 | 9/2009 | Aiferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,780,726 B2 | 6/2010 | Seguin |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hirotsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |

(56) References Cited

U.S. PATENT DOCUMENTS

| | | |
|---|---|---|
| 8,142,493 B2 | 3/2012 | Spence et al. |
| 8,142,495 B2 | 3/2012 | Hasenkam et al. |
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webier et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Abn et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Aikhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0229350 A1 | 12/2003 | Kay |
| 2003/0229395 A1 | 12/2003 | Cox |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |

(56) References Cited

U.S. PATENT DOCUMENTS

| | | |
|---|---|---|
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Boom et al. |
| 2004/0260344 A1 | 12/2004 | Lyons et al. |
| 2004/0260393 A1 | 12/2004 | Randert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Saiahieh et al. |
| 2005/0137695 A1 | 6/2005 | Salahieh et al. |
| 2005/0177228 A1 | 6/2005 | Solem et al. |
| 2005/0159728 A1 | 7/2005 | Armour et al. |
| 2005/0171601 A1 | 8/2005 | Cosgrove et al. |
| 2005/0177180 A1 | 8/2005 | Kaganov et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0065011 A1 | 3/2006 | Komatsu et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0184240 A1 | 6/2006 | Jimenez et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Beef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1 | 5/2007 | Loulmet |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0255397 A1 | 11/2007 | Ryan et al. |
| 2007/0255400 A1 | 11/2007 | Parravicini et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065204 A1 | 3/2008 | Macoviak et al. |
| 2008/0071366 A1 | 3/2008 | Tuval et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |

(56) References Cited

U.S. PATENT DOCUMENTS

| | | |
|---|---|---|
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0172035 A1 | 7/2008 | Starksen et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0234729 A1 | 9/2008 | Page et al. |
| 2008/0262480 A1 | 10/2008 | Stahler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0088837 A1 | 4/2009 | Gillinov et al. |
| 2009/0166913 A1 | 7/2009 | Guo et al. |
| 2010/0106141 A1 | 4/2010 | Osypka et al. |
| 2010/0130989 A1 | 5/2010 | Bourque et al. |
| 2010/0249497 A1 | 9/2010 | Peine et al. |
| 2010/0280605 A1* | 11/2010 | Hammer .............. A61F 2/2436 623/2.11 |
| 2010/0298929 A1 | 11/2010 | Thornton et al. |
| 2012/0053628 A1 | 3/2012 | Sojka et al. |
| 2012/0089125 A1 | 4/2012 | Scheibe et al. |
| 2013/0053884 A1 | 2/2013 | Roorda |
| 2013/0282059 A1 | 10/2013 | Ketai et al. |
| 2013/0331930 A1 | 12/2013 | Rowe et al. |
| 2014/0067054 A1 | 3/2014 | Chau et al. |
| 2014/0088646 A1 | 3/2014 | Wales et al. |
| 2014/0114390 A1 | 4/2014 | Tobis et al. |
| 2014/0251042 A1 | 9/2014 | Asselin et al. |
| 2015/0094800 A1 | 4/2015 | Chawla |
| 2015/0100116 A1 | 4/2015 | Mohl et al. |
| 2015/0133997 A1 | 5/2015 | Deitch et al. |
| 2015/0230919 A1 | 8/2015 | Chau et al. |
| 2015/0351910 A1 | 12/2015 | Gilmore et al. |
| 2016/0120642 A1 | 5/2016 | Shaolian et al. |
| 2017/0042670 A1 | 2/2017 | Shaolian et al. |
| 2017/0224489 A1 | 8/2017 | Starksen et al. |
| 2018/0008409 A1 | 1/2018 | Kutzik et al. |
| 2018/0168803 A1 | 6/2018 | Pesce et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175346 A1 | 6/2019 | Schaffner et al. |
| 2019/0183648 A1 | 6/2019 | Trapp et al. |
| 2019/0290260 A1 | 9/2019 | Caffes et al. |
| 2019/0290431 A1 | 9/2019 | Genovese et al. |
| 2019/0343633 A1 | 11/2019 | Garvin et al. |

FOREIGN PATENT DOCUMENTS

| | | |
|---|---|---|
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

Ahmadi, Ali et al. "Percutaneously adjustable pulmonary artery band." The Annals of thoracic surgery 60 (1995): S520-S522.

Alfieri et al., "An effective technique to correct anterior mitral leaflet prolapse," J Card 14(6):468-470 (1999).

Alfieri et al., "The double orifice technique in mitral valve repair: a simple solution for complex problems," Journal of Thoracic Cardiovascular Surgery 122:674-681 (2001).

Alfieri et al., "The edge to edge technique," The European Association for Cardio-Thoracic Surgery 14th Annual Meeting Oct. 7-11, Book of Proces. (2000).

Alfieri et al."Novel Suture Device for Beating-Heart Mitral Leaflet Approximation", Ann Thorac Surg. 2002, 74:1488-1493.

Alfieri, "The edge-to-edge repair of the mitral valve," [Abstract] 6th Annual NewEra Cardiac Care: Innovation & Technology, Heart Surgery Forum pp. 103. (2000).

Amplatzer Cardiac Plug brochure (English pages), AGA Medical Corporation (Plymouth, MN) (copyright 2008-2010, downloaded Jan. 11, 2011).

Amplatzer® Cribriform Occluder. A patient guide to Percutaneous, Transcatheter, Atrial Septal Defect Closuer, AGA Medical Corporation, Apr. 2008.

Amplatzer® Septal Occluder. A patient guide to the Non-Surgical Closuer of the Atrial Septal Defect Using the Amplatzer Septal Occluder System, AGA Medical Corporation, Apr. 2008.

Assad, Renato S. "Adjustable Pulmonary Artery Banding." (2014).

Brennan, Jennifer, 510(k) Summary of safety and effectiveness, Jan. 2008.

Daebritz, S. et al. "Experience with an adjustable pulmonary artery banding device in two cases: initial success-midterm failure." The Thoracic and cardiovascular surgeon 47.01 (1999): 51-52.

Dang NC et al. "Simplified Placement of Multiple Artificial Mitral Valve Chords," The Heart Surgery Forum #2005-1005, 8 (3) (2005).

Dictionary.com definition of "lock", Jul. 29, 2013.

Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).

Elliott, Daniel S., Gerald W. Timm, and David M. Barrett. "An implantable mechanical urinary sphincter: a new nonhydraulic design concept." Urology52.6 (1998): 1151-1154.

Langer et al. Ring plus String: Papillary muscle repositioning as an adjunctive repair technique for ischemic mitral regurgitation, the Journal of Thoracic Cardiovascular surgery vol. 133 No. 1, Jan. 2007.

Langer et al. Ring+String, Successful Repair technique for ischemic mitral regurgitation with severe leaflet Tethering, the Department of Thoracic Cardiovascular surgery, Hamburg, Germany, Nov. 2008.

Maisano, The double-orifice technique as a standardized approach to treat mitral . . . , European Journal of Cardio-thoracic Surgery 17 (2000) 201-205.

Odell JA et al., "Early Results o4yf a Simplified Method of Mitral Valve Annuloplasty," Circulation 92:150-154 (1995).

(56) References Cited

OTHER PUBLICATIONS

O'Reilly S et al., "Heart valve surgery pushes the envelope," Medtech Insight 8(3): 73, 99-108 (2006).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence," Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

\* cited by examiner

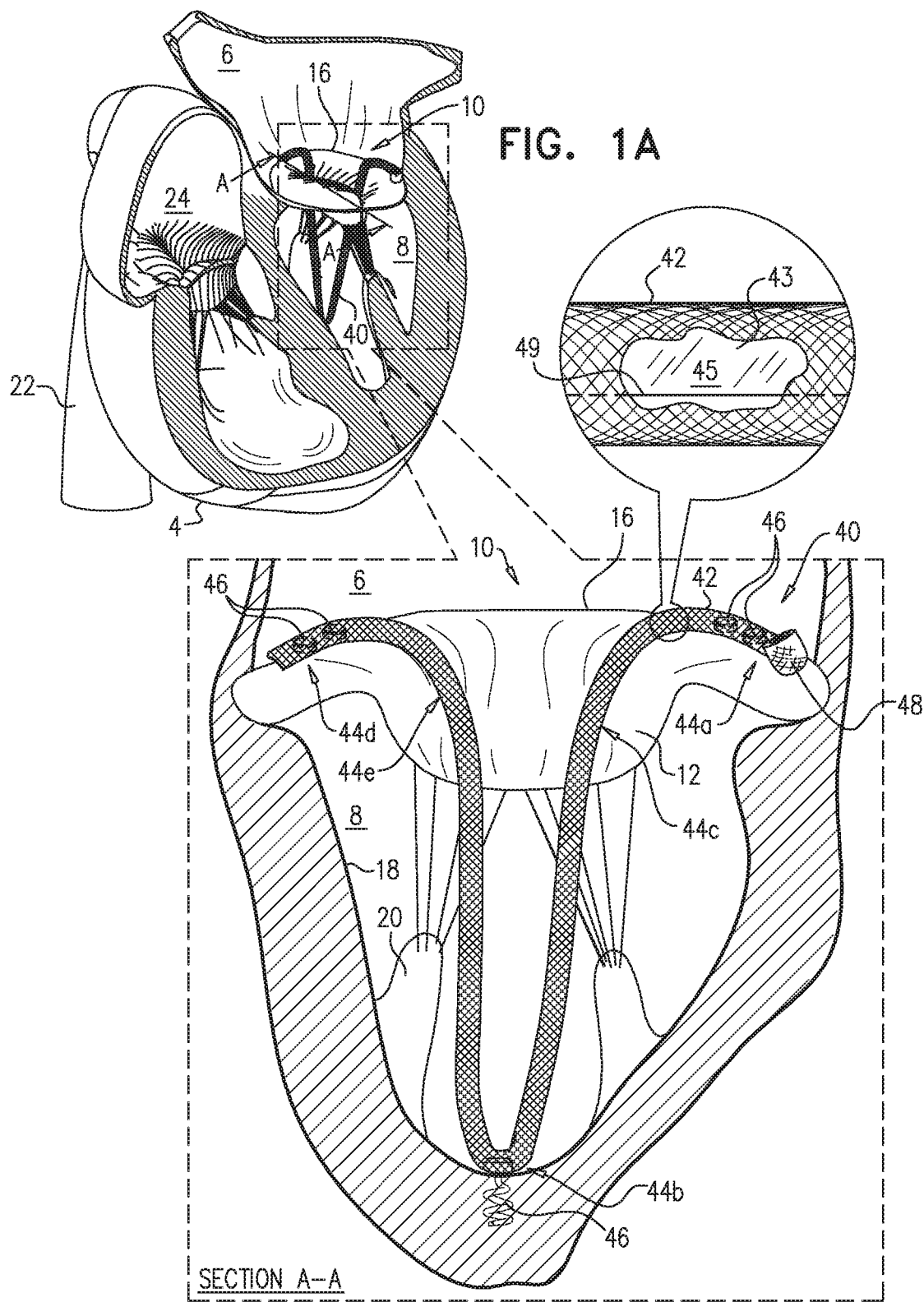

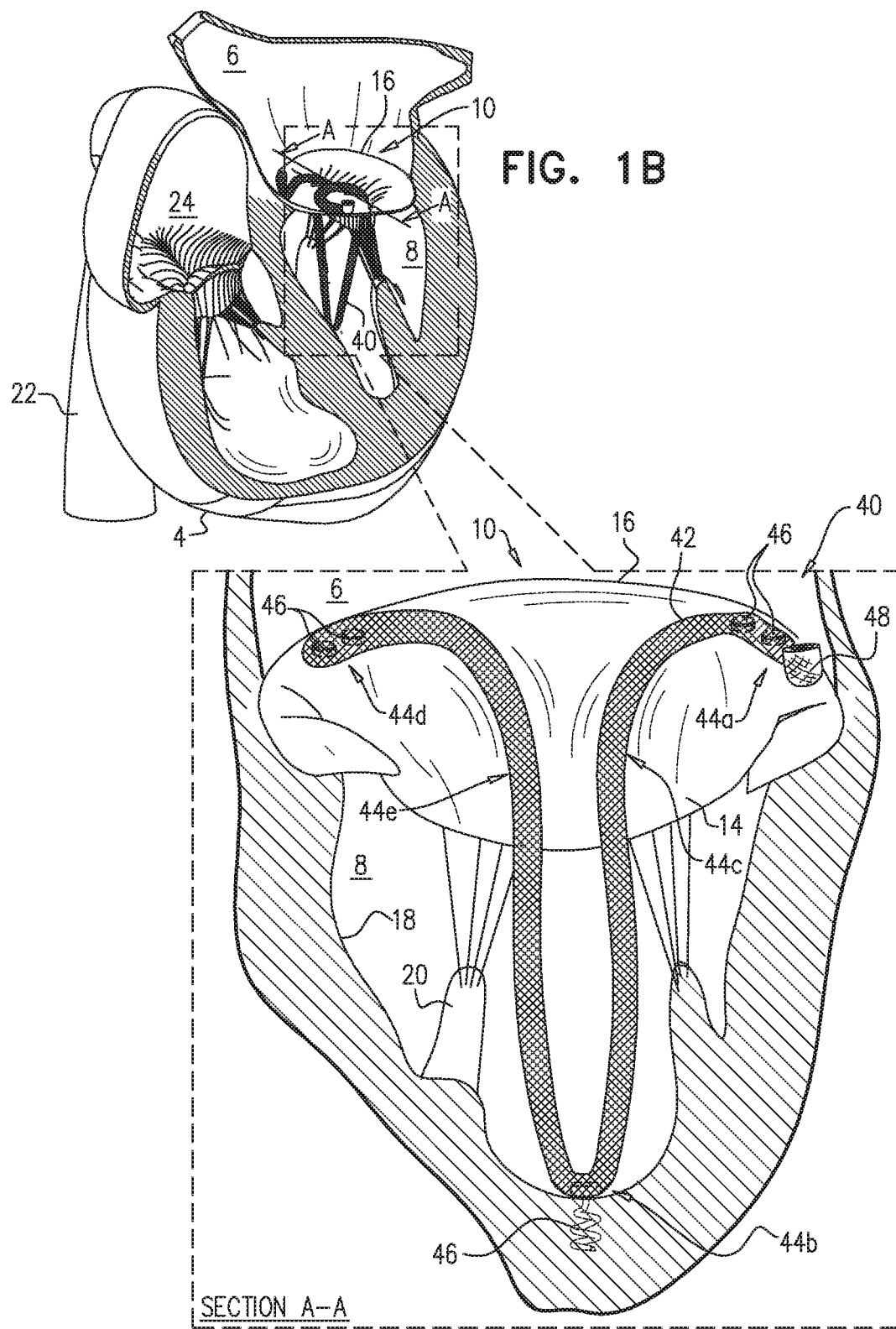

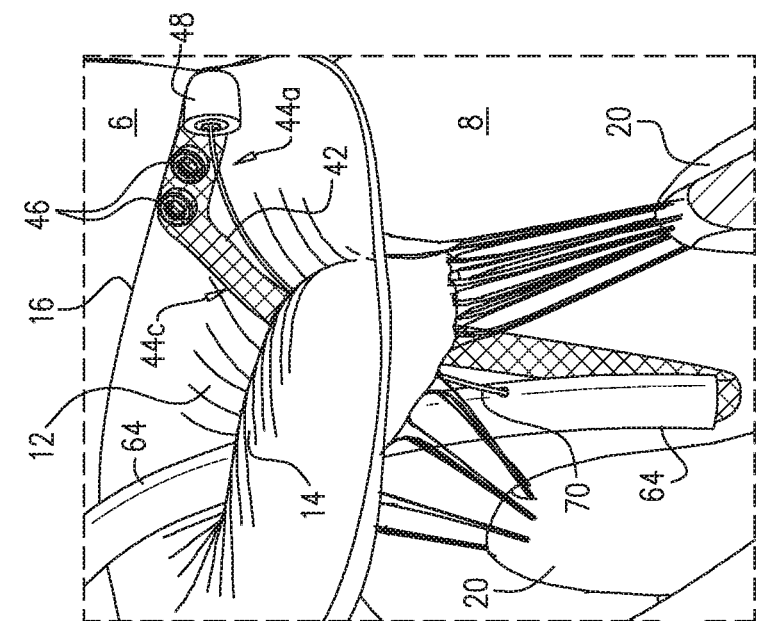
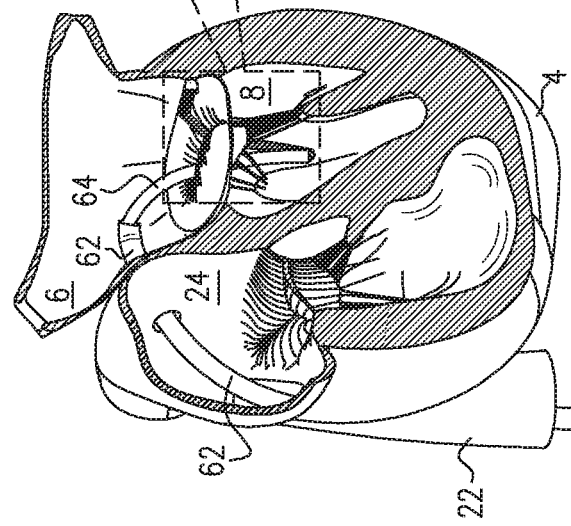
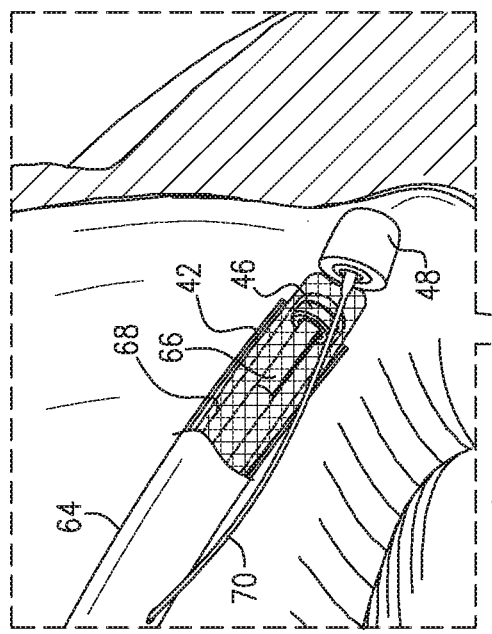
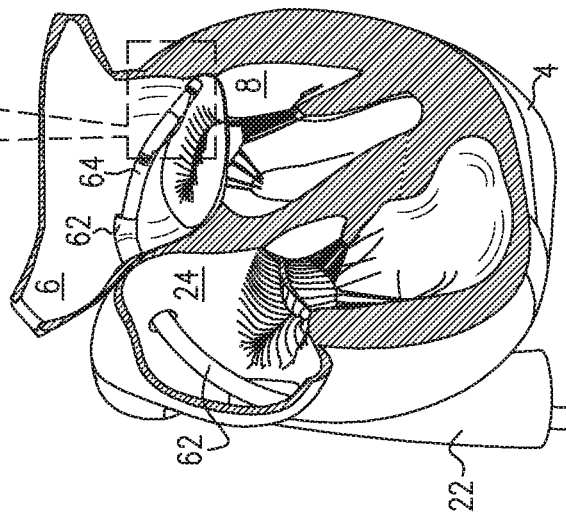
FIG. 2A
FIG. 2B

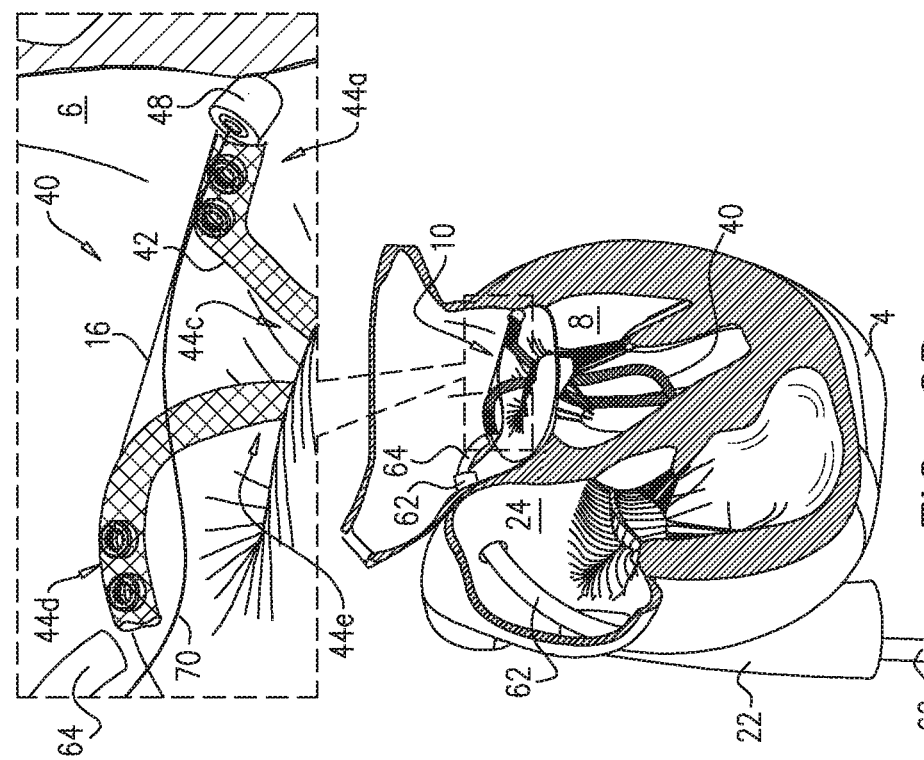
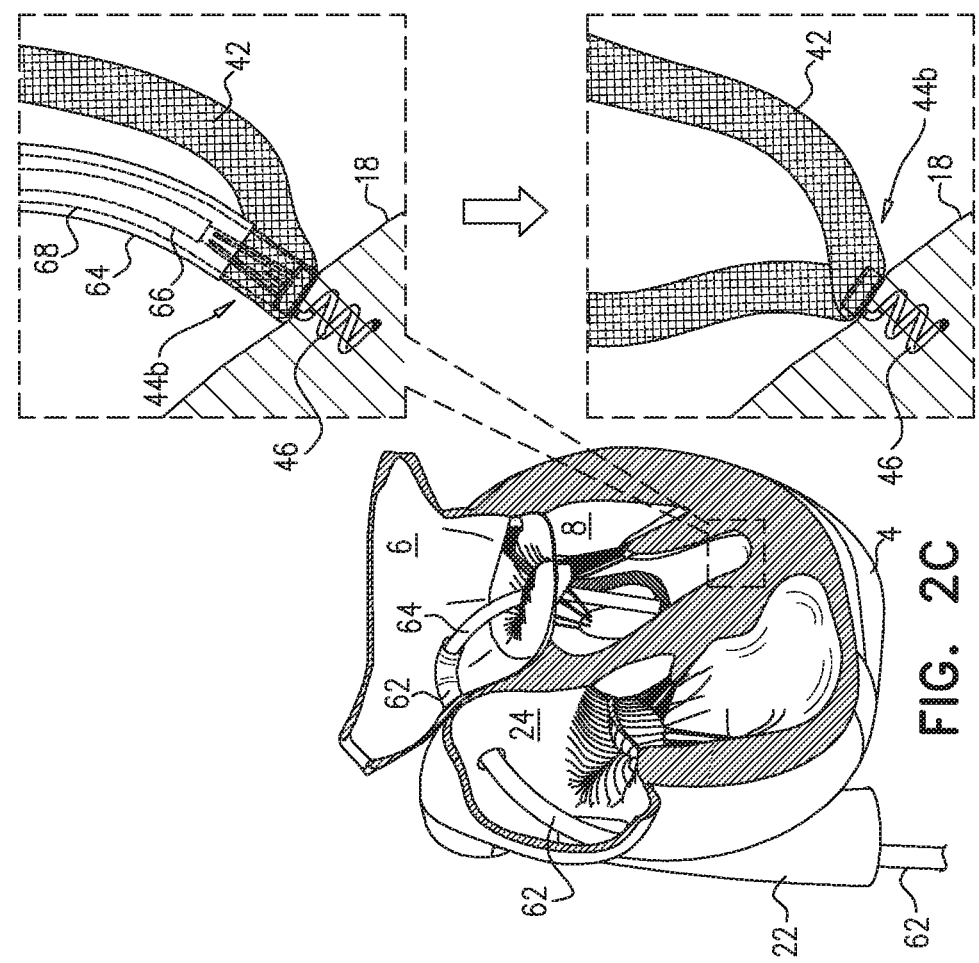
FIG. 2C
FIG. 2D

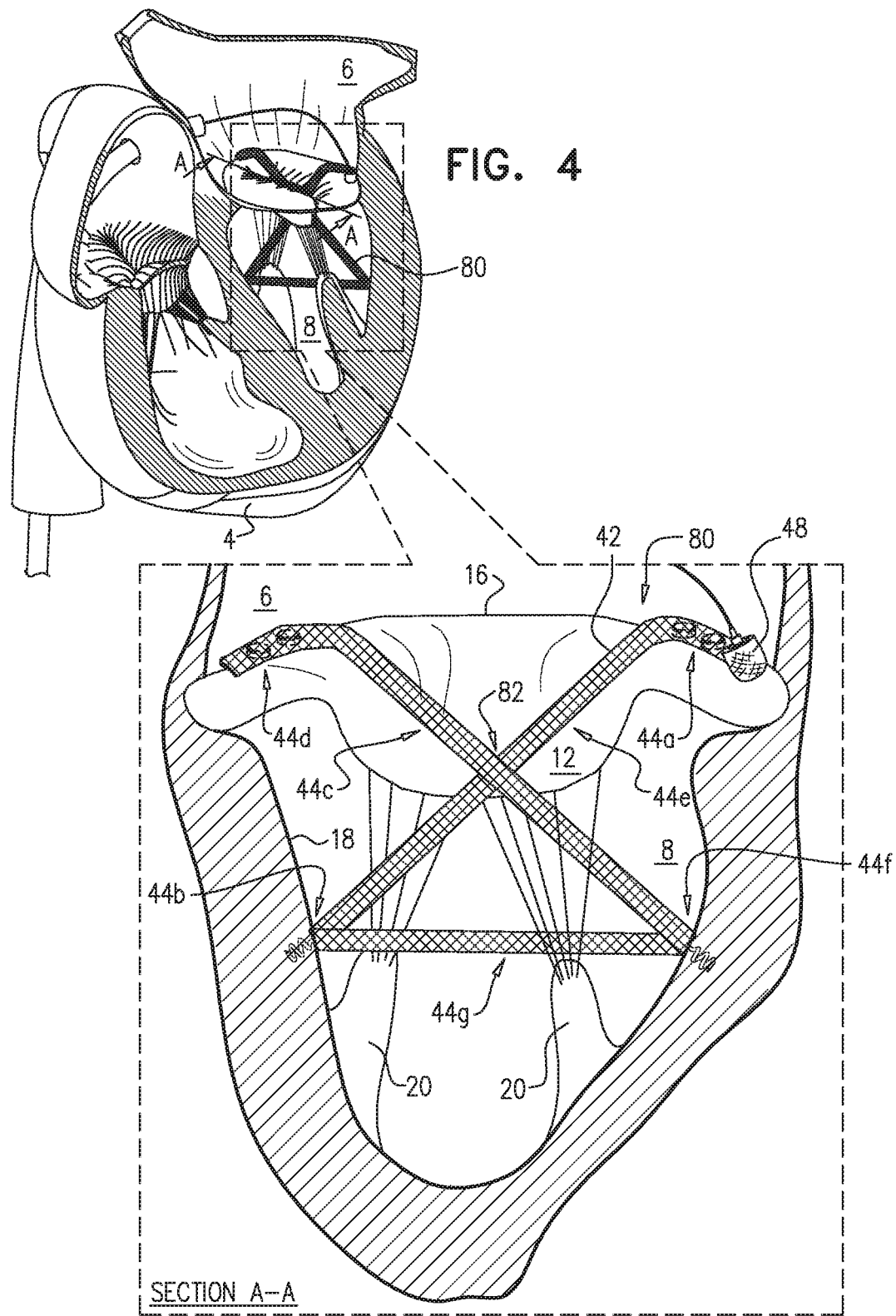

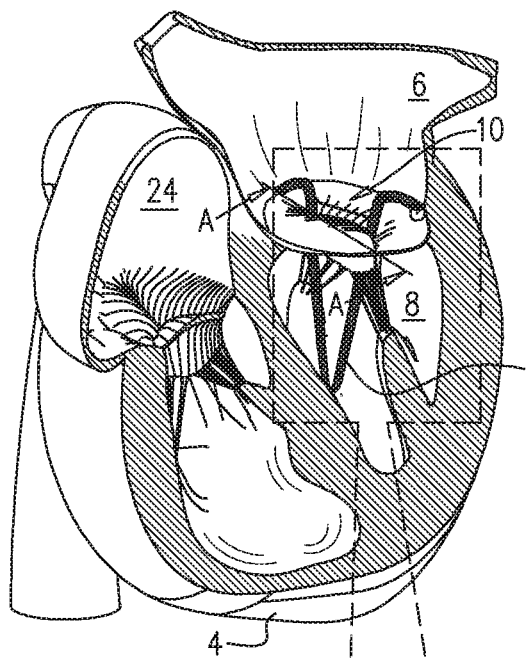
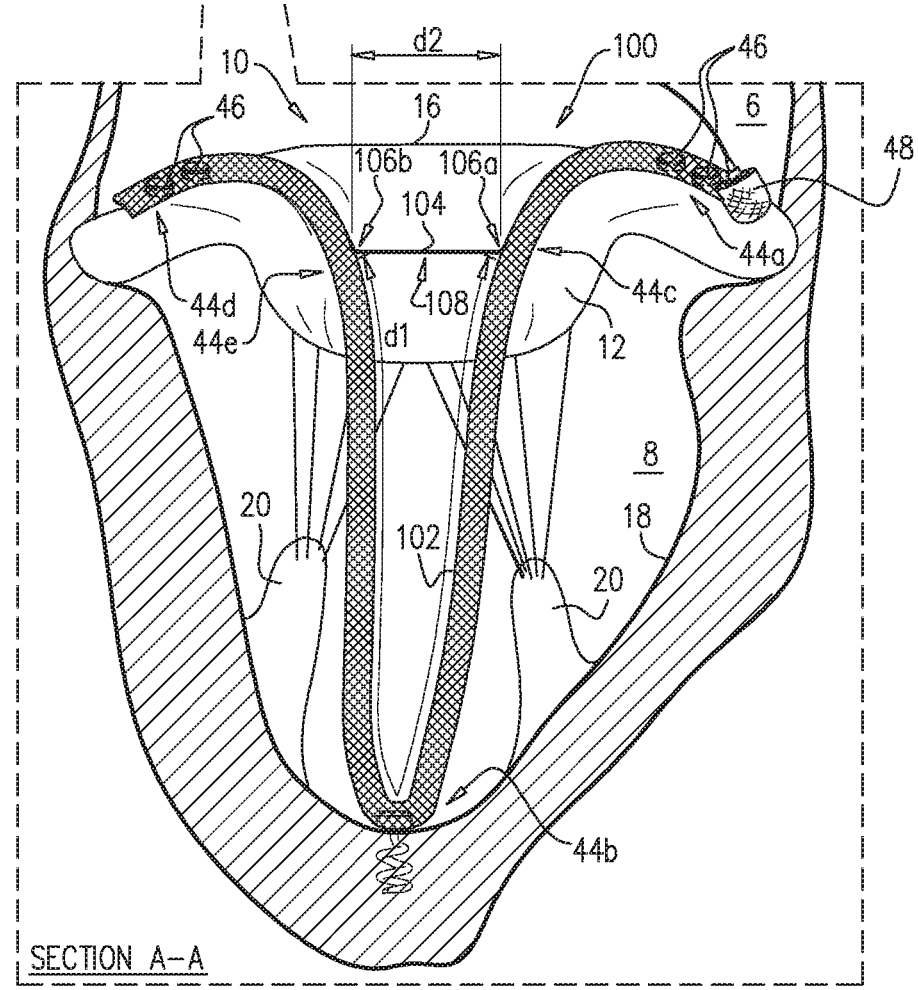
FIG. 5A

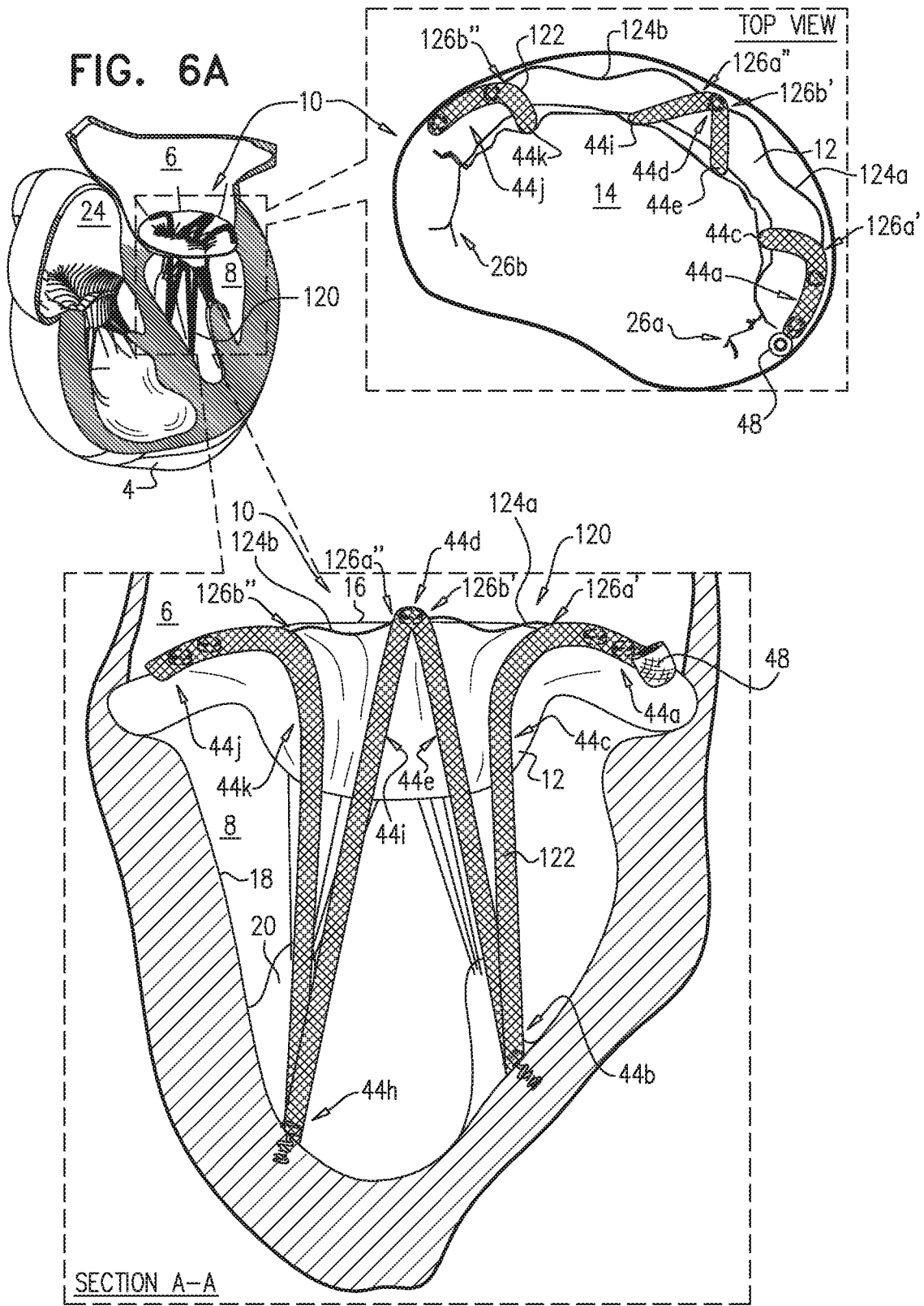

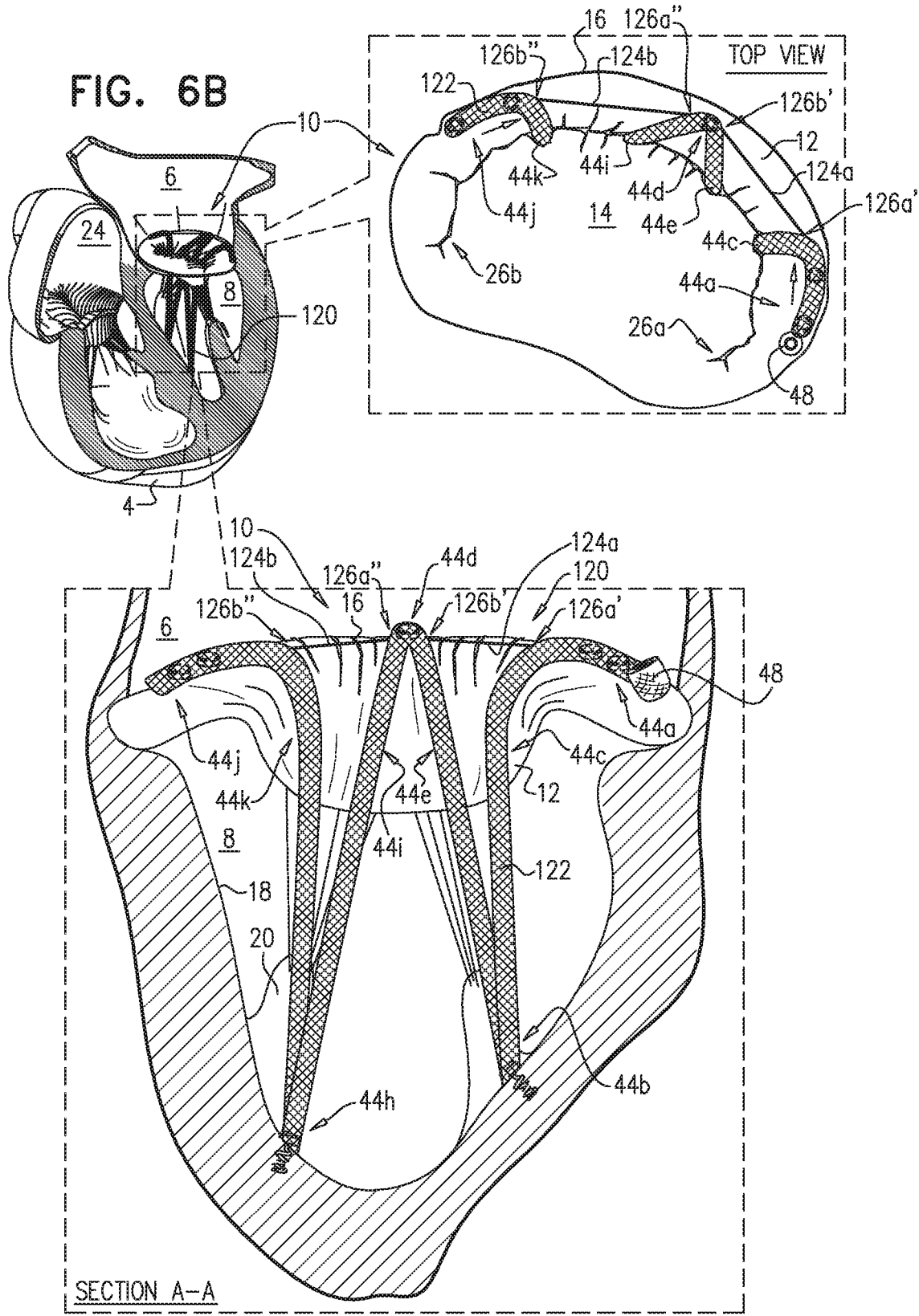

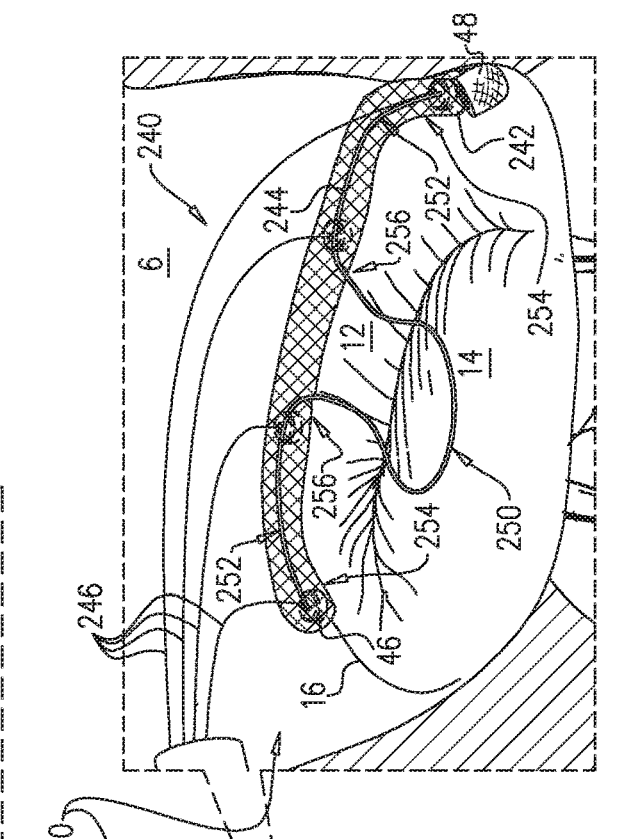
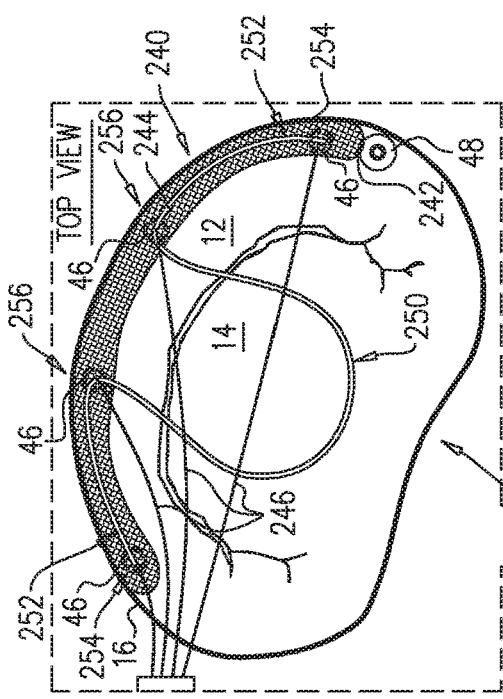
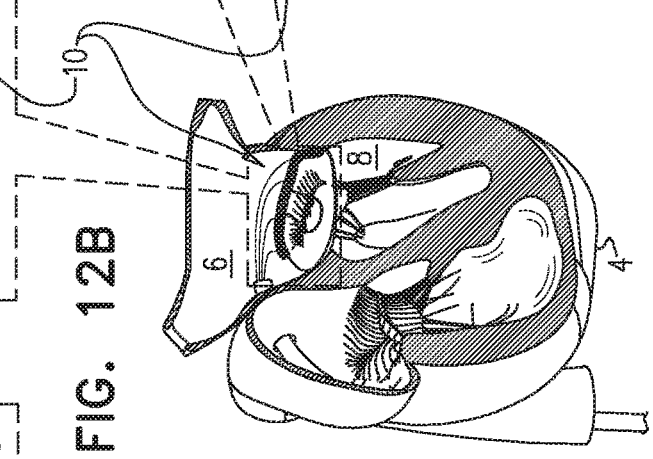
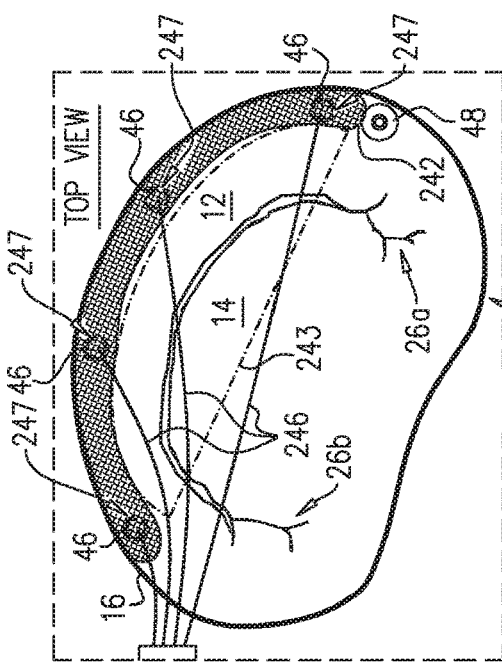
FIG. 12B
FIG. 12A

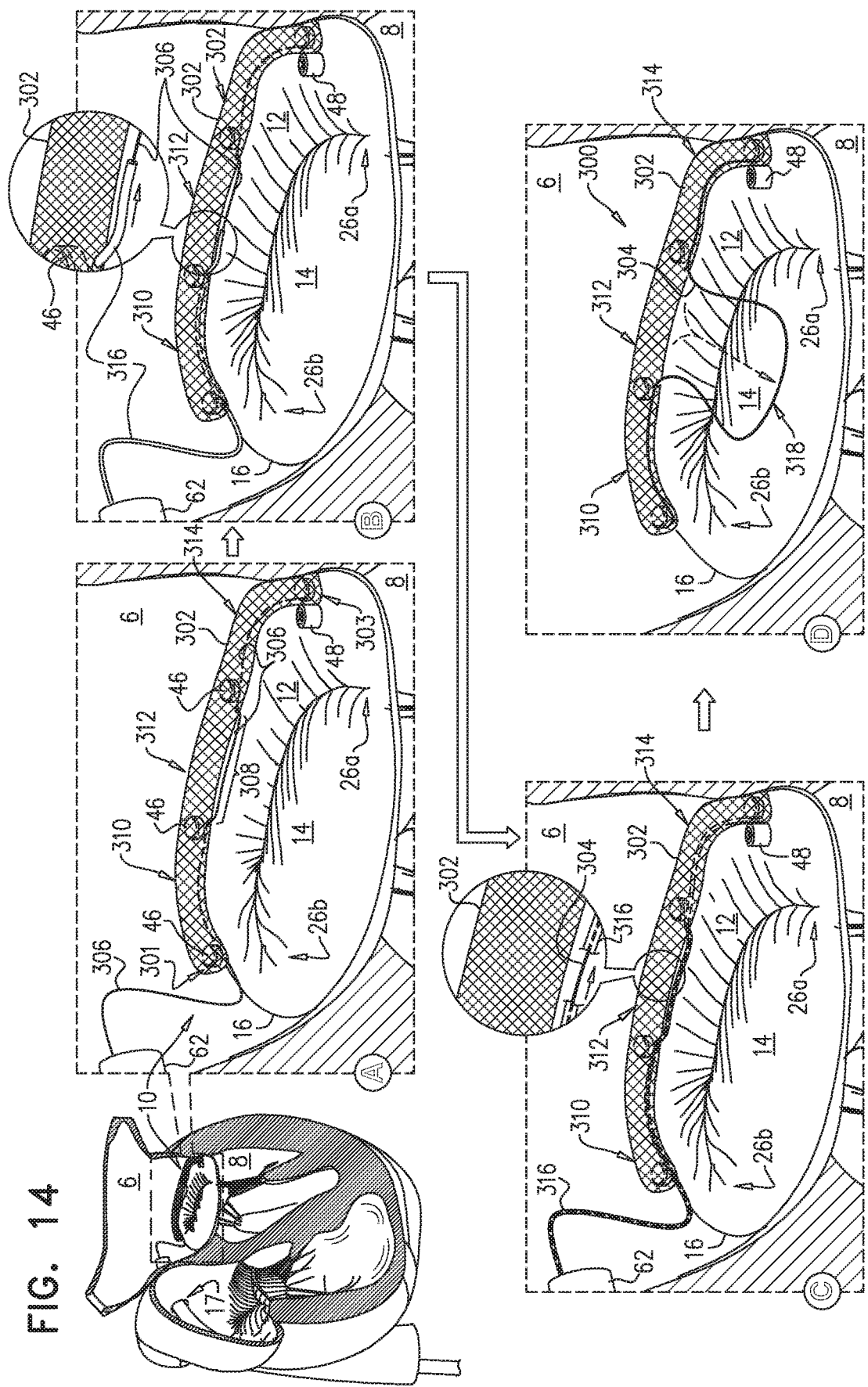

LEAFLET-RESTRAINING TECHNIQUES

CROSS-REFERENCES TO RELATED APPLICATIONS

The present application is a Continuation of U.S. Ser. No. 15/519,520 to Gross et al., filed on Apr. 14, 2017, and entitled "Leaflet-restraining techniques," which published as US 2017/0245993, and which is the US National Phase of PCT application IL2015/051027 to Gross et al, filed on Oct. 14, 2015, and entitled "Leaflet-restraining techniques," which published as WO 2016/059639, and which claims priority from U.S. provisional patent application 62/063,468 to Gross et al., filed on Oct. 14, 2014, and entitled "Leaflet-restraining techniques," which is incorporated herein by reference.

FIELD OF THE INVENTION

Some applications of the invention relate in general to the treatment of heart valves. Some applications of the invention relate more specifically to percutaneously-deliverable implants for the treatment of valve leaflet prolapse.

BACKGROUND

Prolapse of a heart valve leaflet is routinely treated by surgery. Devices have been described that are implanted at the native valve so as to inhibit movement of the leaflet into the atrium.

SUMMARY OF THE INVENTION

Percutaneously-implantable implants are provided to improve coaptation of native heart valve leaflets by inhibiting movement of a prolapsing leaflet into the atrium.

For some applications, an implant comprises a longitudinal member (e.g., a tubular member) that is implanted so as to define one or more valve-traversing portions which inhibit movement of at least one leaflet of the native valve. For some applications the longitudinal member is contractible subsequently to its implantation.

For some applications, a linking member links linking sites at respective portions of the longitudinal member. For some such applications the linking member links the valve-traversing portions, and may itself inhibit movement of the at least one leaflet. For some applications the linking member is tensionable. For some such applications the linking member configures the implant to serve as an annuloplasty device.

For some applications, the longitudinal member is implanted in a stepwise manner by advancing the longitudinal member distally through a catheter, and deploying and anchoring to heart tissue progressively proximal portions of the longitudinal member.

For some applications, an implant comprises a support structure and a leaflet-restraining frame. The support structure is couplable to the annulus of the native valve, and the leaflet-restraining frame is advanceable to the native valve independently of the frame, and couplable to the frame at the native valve. For some applications a leaflet-restraining portion of the frame is positioned upstream of the native valve (i.e., does not traverse the native valve). For some applications, the leaflet-restraining portion of the frame does traverse the native valve (i.e., passes between leaflets of the native valve).

There is therefore provided, in accordance with an application of the present invention, apparatus for use with a heart of a subject, the apparatus including:
a catheter, transluminally advanceable to the heart;
an implant, including
a flexible longitudinal member, and
a linking member that extends from a first linking site of the longitudinal member to a second linking site of the longitudinal member, the implant having:
a delivery state in which (1) the implant is slidable through at least part of the catheter, (2) the longitudinal member is coaxial with the catheter, and (3) at least a portion of the linking member is disposed alongside the longitudinal member, and
an implanted state in which (1) a first distance between the first linking site and the second linking site, measured along the longitudinal member, is greater than a second distance between the first linking site and the second linking site, measured along the linking member, (2) the linking member has a mid-portion disposed between the first linking site and the second linking site, and (3) the mid-portion is not in contact with the longitudinal member; and
a plurality of tissue anchors, slidable through the catheter and with respect to the longitudinal member, each tissue anchor of the plurality of tissue anchors configured to anchor a respective portion of the longitudinal member to a respective location of tissue of the heart.

In an application, in the implanted state, the mid-portion is disposed at least 10 mm from the longitudinal member.

In an application, the portion of the linking member includes the mid-portion of the linking member.

In an application, the linking member is elastic.

In an application, the longitudinal member includes:
a first portion anchorable to atrial tissue of the heart by a first tissue anchor of the plurality of tissue anchors;
a second portion anchorable to ventricular tissue of the heart by a second tissue anchor of the plurality of tissue anchors;
a third portion including the first linking site, disposed between the first portion and the second portion, and placeable against a leaflet of the heart;
a fourth portion anchorable to atrial tissue of the heart by a third tissue anchor of the plurality of tissue anchors; and
a fifth portion including the second linking site, disposed between the second portion and the fourth portion, and placeable against the leaflet of the heart.

In an application, the implant further includes a resilient strand disposed within at least a portion of the longitudinal member, and configured to bias the longitudinal member toward assuming a particular shape.

In an application, the resilient strand is aligned along the portion of the longitudinal member.

In an application, the portion of the longitudinal member includes the first linking site.

In an application, in the delivery state, the portion of the linking member that is disposed alongside the longitudinal member is disposed less than 1 mm from the linking member.

In an application, in the delivery state, the portion of the linking member that is disposed alongside the longitudinal member is in contact with the linking member.

In an application, the second distance is adjustable by the linking member being slidable with respect to the longitudinal member at at least one of the linking sites.

In an application, the implant further includes a locking mechanism, and the second distance is fixable by locking the locking mechanism to the linking member.

In an application, the locking mechanism includes a ratcheting mechanism.

In an application, the apparatus further includes at least one anchor driver, slidable within the catheter and with respect to the longitudinal member, and configured to anchor the respective portions of the longitudinal member to the respective locations of the tissue using the tissue anchors.

In an application:
the flexible longitudinal member is a flexible tubular member, including a wall that defines a lumen,
the linking member extends from the first linking site outside of the tubular member to the second linking site,
the plurality of tissue anchors are slidable within the lumen of the tubular member,
the anchor driver is slidable within the lumen of the tubular member, and is configured to anchor the respective portions by driving the tissue anchors from the lumen, through the wall and into the respective locations of tissue.

In an application, the wall includes a lateral wall that circumscribes the lumen and a distal wall that defines a distal end of the lumen, and the apparatus is configured such that (1) at least one tissue anchor of the plurality of tissue anchors is drivable by the anchor driver through the distal wall, and (2) another at least one tissue anchor of the plurality of tissue anchors is drivable by the anchor driver through the lateral wall.

There is further provided, in accordance with an application of the present invention, apparatus for use with a heart of a subject, the apparatus including:
a catheter, transluminally advanceable to the heart; an implant, including:
a flexible longitudinal member, and
a linking member that extends from a first linking site of the longitudinal member to a second linking site of the longitudinal member,
a plurality of tissue anchors including at least a first tissue anchor, a second tissue anchor and a third tissue anchor, each of the tissue anchors being slidable through the catheter, and configured to anchor a respective one of a plurality of portions of the longitudinal member to a respective one of a plurality of locations of tissue of the heart; and
at least one anchor driver, configured to anchor the plurality of portions of the longitudinal member to the plurality of locations using the plurality of tissue anchors; the anchor driver and the implant being slidable through the catheter and with respect to each other such that:
a distal portion of the plurality of portions is anchorable to a first location of tissue by the first tissue anchor while the first linking site is disposed within the catheter,
while (1) the distal portion is anchored to the first location, and (2) the second linking site is disposed within the catheter, a second portion of the plurality of portions is advanceable distally out of the catheter and anchorable to a second location of tissue by the second tissue anchor,
while the second portion is anchored to the second location, the second linking site and a third portion of the plurality of portions are advanceable distally out of the catheter, and
after the second linking site has been advanced out of the catheter, the third portion is anchorable to a third location of tissue by the third tissue anchor.

In an application:
the first location of tissue is a location of a first tissue selected from the group consisting of: atrial tissue and ventricular tissue,
the second location of tissue is a location of a second tissue (1) selected from the group consisting of: atrial tissue and ventricular tissue, and (2) not the first selected tissue, and
the distal portion of the longitudinal member is configured to be anchored by the first tissue anchor to the location of the first selected tissue, and the second portion of the longitudinal member is configured to be anchored by the second tissue anchor to the location of the second selected tissue.

In an application, the second portion is disposed 1-6 cm along the longitudinal member from the distal portion.

In an application, the second portion is disposed 1.5-3 cm along the longitudinal member from the distal portion.

In an application, the first linking site is disposed 0.5-4 cm along the longitudinal member from the distal portion, and 1-5 cm along the longitudinal member from the second portion.

In an application, the third portion is disposed 1-6 cm along the longitudinal member from the second portion.

In an application, the third portion is disposed 1.5-3 cm along the longitudinal member from the second portion.

In an application, the second linking site is disposed 0.5-4 cm along the longitudinal member from the second portion, and 1-5 cm along the longitudinal member from the third portion.

There is further provided, in accordance with an application of the present invention, apparatus for use with a heart of a subject, the apparatus including:
a catheter, transluminally advanceable to the heart;
an implant, including:
a flexible tubular member including a wall that defines a lumen, and
a linking member that extends, outside of the tubular member, from a first linking site of the tubular member to a second linking site of the tubular member, the implant having:
a delivery state in which (1) the implant is slidable through at least part of the catheter, (2) the flexible tubular member is coaxial with the catheter, and (3) at least a portion of the linking member is disposed alongside the tubular member, and
an implanted state in which (1) a first distance between the first linking site and the second linking site, measured along the tubular member, is greater than a second distance between the first linking site and the second linking site, measured along the linking member, (2) the linking member has a mid-portion disposed outside of the tubular member between the first linking site and the second linking site, and (3) the mid-portion is not in contact with the wall of the tubular member for at least 0.5 cm of the linking member;
a plurality of tissue anchors, slidable within the lumen; and
at least one anchor driver, slidable within the catheter and within the lumen, and configured to drive the tissue anchors through the wall and into tissue of the heart.

In an application, the portion of the linking member includes the mid-portion of the linking member.

In an application, the linking member is elastic.

In an application, in the implanted state, the mid-portion is disposed at least 10 mm from the wall of the tubular member.

In an application, the tubular member includes:

a first portion anchorable to atrial tissue of the heart by a first tissue anchor of the plurality of tissue anchors;

a second portion anchorable to ventricular tissue of the heart by a second tissue anchor of the plurality of tissue anchors;

a third portion including the first linking site, disposed between the first portion and the second portion, and placeable against a leaflet of the heart;

a fourth portion anchorable to atrial tissue of the heart by a third tissue anchor of the plurality of tissue anchors; and a fifth portion including the second linking site, disposed between the second portion and the fourth portion, and placeable against the leaflet of the heart.

In an application, in the delivery state, the portion of the linking member that is disposed alongside the tubular member is disposed less than 1 mm from the wall of the tubular member.

In an application, in the delivery state, the portion of the linking member that is disposed alongside the tubular member is in contact with the wall of the tubular member.

In an application, the second distance is adjustable by the linking member being slidable through the wall at at least one of the linking sites.

In an application, the implant further includes a locking mechanism, and the second distance is fixable by locking the locking mechanism to the linking member.

In an application, the locking mechanism includes a ratcheting mechanism.

In an application, a proximal end of the linking member is slidable within the lumen.

In an application, the wall includes a lateral wall that circumscribes the lumen and a distal wall that defines a distal end of the lumen.

In an application, the apparatus is configured such that at least one tissue anchor of the plurality of tissue anchors is drivable by the anchor driver through the distal wall, and another at least one tissue anchor of the plurality of tissue anchors is drivable by the anchor driver through the lateral wall.

There is further provided, in accordance with an application of the present invention, apparatus for use with a valve of a heart of a subject, the valve having an annulus that defines an orifice, and a plurality of leaflets, and the apparatus including:

a catheter, transluminally advanceable to the heart;

a support structure including a flexible tubular member including a wall that defines a lumen;

a plurality of tissue anchors;

at least one anchor driver, slidable within the catheter and within the lumen, and configured to anchor the support structure to the annulus by driving the tissue anchors from the lumen, through the wall and into the annulus;

at least one guide member, a distal end of the guide member couplable to the support structure such that, subsequently to the anchoring of the support structure, the guide member extends from the support structure; and a frame:

having a delivery state in which the frame is slidable within the catheter, being configured to be slid along the guide member and subsequently secured to the support structure, and having a working state in which, while the support structure is anchored to the annulus and the frame is secured to the support structure, a leaflet-restraining portion of the frame:

extends away from the support structure and at least partway across an atrial side of the orifice of the valve, inhibits atrially-directed movement of a leaflet of the valve, but not ventricularly-directed movement of the leaflet.

In an application:

the support structure has at least one coupling site at which the frame is securable to the support structure, and the distal end of the guide member is coupled to the support structure at the coupling site.

In an application, the lumen defines a longitudinal axis of the tubular member, and the guide member extends laterally from the tubular member.

In an application, the tubular member is configured to be advanced in a generally linear state through at least part of the catheter, and to be anchored by the tissue anchors to the annulus such that the tubular member assumes an arc defining an arc segment, and the frame is configured to be secured to the support structure such that the portion of the frame extends across at least part of the arc segment.

In an application, while the support structure is anchored to the annulus and the frame is secured to the support structure, the leaflet-restraining portion of the frame does not extend ventricularly more than 1 cm past the leaflets of the valve.

In an application, while the support structure is anchored to the annulus and the frame is secured to the support structure, the leaflet-restraining portion of the frame does not extend ventricularly past the valve.

In an application, the lumen defines a longitudinal axis of the tubular member, and the guide member extends longitudinally through at least part of the lumen and away from the tubular member.

In an application, the frame is advanceable, while in the delivery state, along the guide member and through the at least part of the lumen.

In an application, the frame is configured to be transitioned from the delivery state into the working state subsequently to the advancement of the frame through the at least part of the lumen.

In an application:

the guide member extends through the lumen of a first section of the tubular member, out through the wall, alongside a second section of the tubular member, and back in through the wall, and the frame is advanceable along the guide member such that:

the leaflet-restraining portion becomes disposed alongside the second section of the tubular member, and subsequent transitioning of the frame from the delivery state into the working state moves the leaflet-restraining portion away from the second section of the tubular member.

In an application:

the guide member is tubular and defines a channel therethrough, the frame is advanceable along the guide member by being advanced though the channel, and the frame is configured to automatically transition into the working state upon becoming exposed from a distal end of the guide member.

In an application:

the guide member is a secondary guide member, the apparatus further includes a primary guide member, more flexible than the secondary guide member, the support structure is configured to be advanced through the catheter while a distal end of the primary guide member is coupled to the support structure, and the secondary guide member is advanceable over the primary guide member and through the at least part of the lumen subsequent to the anchoring of the support structure.

In an application, support structure is configured to be advanced distally through the catheter while the primary guide member extends from a distal end of the tubular member, proximally between the tubular member and an inner surface of the catheter, and proximally away from the support structure.

In an application:

the frame has a force-distributing portion that is different from the leaflet-restraining portion, and in the working state, while the support structure is anchored to the annulus and the frame is secured to the support structure, the apparatus:

defines fulcrum sites, and is configured such that an atrially-directed force applied by the leaflet to the leaflet-restraining portion is transferred via the fulcrum sites to the force-distribution portion.

In an application, the apparatus is configured such that in response to the atrially-directed force, the force-distribution portion applies a pressing force to tissue of the heart.

In an application, the apparatus is configured such that in response to the atrially-directed force, the force-distribution portion applies a pulling force to tissue of the heart.

In an application, the apparatus is configured such that while the support structure is anchored to the annulus and the frame is secured to the support structure, the force-distribution portion is disposed against an atrial wall of the heart.

In an application, the apparatus is configured such that while the frame is secured to the support structure, the force-distribution portion extends away from the support structure in a direction that is generally opposite to a direction in which the leaflet-restraining portion extends away from the support structure.

In an application, the frame has one or more coupling sites at which the frame is securable to the support structure, and the coupling sites are disposed between the leaflet-restraining portion and the force-distributing portion of the frame.

In an application, while the support structure is anchored to the annulus and the frame is secured to the support structure, the support structure serves as a fulcrum via which the atrially-directed force is transferred to the force-distribution portion.

There is further provided, in accordance with an application of the present invention, apparatus for use with a valve of a heart of a subject, the valve having an annulus that defines an orifice, and at least one leaflet, and the apparatus including:

a catheter, transluminally advanceable to the heart;

a support structure, advanceable to the heart via the catheter;

a plurality of tissue anchors, advanceable to the heart via the catheter;

at least one anchor driver, slidable within the catheter and configured to anchor the support structure to the annulus using the tissue anchors;

a frame:

having a delivery state in which the frame is transluminally advanceable to the heart via the catheter independently of the support structure, having an expanded state in which the frame defines a leaflet-restraining portion and a force-distribution portion, and being configured to be intracorporeally secured to the support structure, the implant having a working state in which:

the support structure is anchored to the annulus, the frame is in the expanded state thereof and is secured to the support structure, the leaflet-restraining portion and the force-distribution portion of the frame extend away from the support structure, and the support structure serves as a fulcrum via which a force applied to the leaflet-restraining portion by atrially-directed movement of the leaflet is transferred to the force-distribution portion.

There is further provided, in accordance with an application of the present invention, apparatus for use with a heart of a subject, the apparatus including:

a steerable catheter, transluminally advanceable to inside of the heart;

a tubular member, slidable through the catheter, shaped to define a lumen, and having a distal end and a proximal end, and a length therebetween that is at least 13 cm;

a plurality of tissue anchors including at least a first tissue anchor and a second tissue anchor, configured to anchor respective portions of the tubular member to respective locations of tissue of the heart; and an anchor driver, slidable through the catheter and within the lumen, and configured to use the plurality of tissue anchors to anchor the respective portions of the tubular member to the respective locations.

In an application, the length of the tubular member is 13-25 cm.

In an application, the length of the tubular member is at least 14 cm.

In an application, the length of the tubular member is 14-25 cm.

In an application, the length of the tubular member is at least 15 cm.

In an application, the length of the tubular member is 15-25 cm.

In an application, the length of the tubular member is at least 18 cm.

In an application, the length of the tubular member is 18-25 cm.

There is further provided, in accordance with an application of the present invention, apparatus for use with a heart of a subject, the apparatus including:

a longitudinal member:

having a first anchor site, a second anchor site, and a third anchor site therebetween, having a first longitudinal portion extending between the first anchor site and the second anchor site, and a second longitudinal portion extending between the second anchor site and the third anchor site, the first and second longitudinal portions forming a V-shape, and shaped to define a lumen through the first and second longitudinal portions, that provides fluid communication between the first anchor site and the third anchor site; and a plurality of tissue anchors including at least a first tissue anchor anchored to the first portion, a second tissue anchor anchored to the second portion, and a third tissue anchor anchored to the third portion.

In an application, each tissue anchor of the plurality of tissue anchors includes an anchor head and a tissue-engaging element, the anchor head is disposed within the lumen, the tissue-engaging element is disposed outside of the lumen, and the lumen provides fluid communication between the anchor head of each tissue anchor of the plurality of tissue anchors.

In an application, the first longitudinal portion is disposed at an angle of between 10 and 150 degrees with respect to the second longitudinal portion.

In an application, the first longitudinal portion is disposed at an angle of between 30 and 110 degrees with respect to the second longitudinal portion.

In an application, the apparatus further includes a linking member that extends from a first linking site of the first longitudinal portion to a second linking site of the second longitudinal portion.

In an application, a first distance between the first linking site and the second linking site, measured along the longitudinal member, is greater than a second distance between the first linking site and the second linking site, measured along the linking member.

In an application, the second tissue anchor is disposed 1-6 cm from the first tissue anchor.

In an application, the third tissue anchor is disposed 1-6 cm from the second tissue anchor.

There is further provided, in accordance with an application of the present invention, apparatus, including a transluminally-deliverable tissue anchor, including:

a tissue-engaging element:
having a distal tip configured to be pushed into tissue of a heart of a subject, and
configured to anchor the tissue anchor to the tissue; and
a carabiner coupled to a proximal portion of the tissue-engaging element.

In an application, the carabiner includes a single loop that forms a hook portion and a spring-loaded gate portion.

There is further provided, in accordance with an application of the present invention, a method for use with a heart of a subject, including:

delivering to the heart a longitudinal flexible sleeve that includes a lateral wall that circumscribes and defines a lumen of the sleeve;

anchoring the sleeve to tissue of the heart by moving a tissue anchor through the lumen, and driving a tissue-engaging element of the tissue anchor through the lateral wall and into tissue of the heart; and facilitating narrowing of the lumen at at least a longitudinal portion of the sleeve.

In an application, facilitating narrowing of the lumen includes applying longitudinal tension to at least the longitudinal portion of the sleeve.

In an application, facilitating narrowing of the lumen includes placing at least the longitudinal portion of the sleeve between leaflets of a valve of the heart, such that the leaflets press against the lateral wall.

In an application, facilitating narrowing of the lumen includes facilitating contact between opposing sides of the lateral wall.

There is further provided, in accordance with an application of the present invention, a method for use with a native valve of a heart of a subject, the native valve having one or more leaflets, and the method including:

advancing, toward the valve of the subject, an implant including a flexible longitudinal member disposed within a catheter;

using a first tissue anchor, anchoring a distal portion of the longitudinal member to tissue of an atrium of the heart;

subsequently, (1) advancing out of the catheter a second portion of the longitudinal member, the second portion being proximal to the distal portion, and (2) using a second tissue anchor, anchoring the second portion of the longitudinal member to tissue of a ventricle of the heart such that a third portion of the longitudinal member, disposed between the first portion and the second portion, traverses the valve and inhibits movement of at least one of the one or more leaflets of the valve; and subsequently, (1) advancing out of the catheter a fourth portion of the longitudinal member, the fourth portion being proximal to the second portion, and (2) using a third tissue anchor, anchoring the fourth portion of the longitudinal member to tissue of the atrium such that a fifth portion of the longitudinal member, disposed between the second portion and the fourth portion, traverses the valve and inhibits movement of at least one of the one or more leaflets of the valve.

In an application, the method further includes positioning a resilient strand such that the resilient strand is within at least one portion of the longitudinal member selected from the group consisting of: the third portion and the fifth portion.

In an application, anchoring the second portion includes anchoring the second portion such that the third portion inhibits movement of a given leaflet of the one or more leaflets, and anchoring the fourth portion includes anchoring the fourth portion such that the fifth portion inhibits movement of the given leaflet.

In an application, anchoring the second portion includes anchoring the second portion such that the third portion inhibits movement of a first leaflet of the one or more leaflets, and anchoring the fourth portion includes anchoring the fourth portion such that the fifth portion inhibits movement of a second leaflet of the one or more leaflets.

In an application:
the longitudinal member is a flexible tubular member including a lateral wall that defines and circumscribes a lumen, the distal, second, third, fourth and fifth portions of the longitudinal member being distal, second, third, fourth and fifth portions of the tubular member, and anchoring the distal, second, and fourth portions of the longitudinal member includes anchoring the distal, second, and fourth portions of the tubular member, respectively.

In an application:
anchoring the distal portion using the first tissue anchor includes driving the first tissue anchor from within the lumen and through the lateral wall, anchoring the second portion using the second tissue anchor includes driving the second tissue anchor from within the lumen and through the lateral wall, and anchoring the fourth portion using the third tissue anchor includes driving the third tissue anchor from within the lumen and through the lateral wall.

There is further provided, in accordance with an application of the present invention, a method for use with a native valve of a heart of a subject, the method including:

advancing, toward the valve of the subject, an implant including a flexible longitudinal member disposed within a catheter, the longitudinal member having a first portion, a second portion, and a third portion, the second portion disposed along the longitudinal member between the first portion and the third portion;

anchoring the first portion of the longitudinal member to tissue of the heart;

anchoring the third portion of the longitudinal member to tissue of the heart; and subsequently to anchoring the first and third portions, coupling the second portion to a tissue anchor that is anchored to tissue of the heart.

In an application, coupling includes slidably coupling.

In an application, coupling includes hooking the second portion onto the tissue anchor.

In an application, coupling includes moving the second portion through a spring-loaded gate of the tissue anchor.

In an application, the method further includes anchoring the tissue anchor to tissue of the heart before the step of advancing the implant.

In an application, the method further includes anchoring the tissue anchor to tissue of the heart before introducing the implant into the subject.

There is further provided, in accordance with an application of the present invention, a method including:

advancing, toward a valve of a heart of a subject, an implant including a flexible tubular member including a sleeve that defines a lumen;

anchoring a first portion of the tubular member to tissue of an atrium of the heart by placing the first portion of the tubular member within the atrium and driving a first anchor from inside the tubular member through the sleeve and into the tissue of the atrium;

anchoring a second portion of the tubular member to tissue of a ventricle of the heart by placing the second portion of the tubular member within the ventricle and driving a second anchor from inside the tubular member through the sleeve and into the tissue of the ventricle; and placing a third portion of the tubular member, disposed between the first portion and the second portion, such that the third portion traverses the valve and inhibits movement of at least one leaflet of the valve.

In an application, advancing the implant includes advancing the implant transluminally.

In an application, restricting the movement of the at least one leaflet includes increasing coaptation of the at least one leaflet with at least another leaflet of the valve.

In an application, restricting the movement of the at least one leaflet includes restricting movement of the leaflet toward the atrium during ventricular systole.

In an application:

the implant further includes an adjusting mechanism, coupled to the tubular member, and a flexible longitudinal contracting member, coupled to the adjusting mechanism, at least part of the contracting member being disposed within the tubular member, and the method further includes, subsequently to anchoring the first portion and anchoring the second portion, adjusting a length of the tubular member between the first anchor and the second anchor by actuating the adjusting mechanism to adjust a length of the contracting member between the first anchor and the second anchor.

In an application:

advancing the implant includes advancing the implant through a catheter;

the method further includes progressively advancing, out of the catheter: (i) a distal end of the tubular member, (ii) thereafter the third portion of the tubular member, and (iii) thereafter a proximal end of the tubular member; and the method further includes advancing the adjusting mechanism out of the catheter prior to advancing the distal end of the tubular member out of the catheter.

In an application, the second portion of the tubular member includes the distal end of the tubular member, and anchoring the second portion of the tubular member includes anchoring the second portion of the tubular member such that the distal end of the tubular member is disposed in the ventricle of the subject.

In an application:

advancing the implant includes advancing the implant through a catheter;

the method further includes progressively advancing, out of the catheter: (i) a distal end of the tubular member, (ii) thereafter the third portion of the tubular member, and (iii) thereafter a proximal end of the tubular member; and the method further includes advancing the adjusting mechanism out of the catheter subsequently to advancing the proximal end of the tubular member out of the catheter.

In an application, the second portion of the tubular member includes the distal end of the tubular member, and anchoring the second portion of the tubular member includes anchoring the second portion of the tubular member such that the distal end of the tubular member is disposed in the ventricle of the subject.

In an application, the implant is a first implant, the recited steps are steps of implanting the first implant, and the method further includes implanting a second implant following the steps of implanting the first implant.

In an application, the first anchor has a tissue-engaging portion that has a first diameter and the second anchor has a tissue-engaging portion that has a second diameter that is greater than the first diameter, and driving the second anchor includes driving the tissue-engaging portion of the second anchor into the tissue of the ventricle.

In an application, the catheter is a first catheter, advancing the implant through the catheter includes advancing the implant through the first catheter while (i) the sleeve is disposed within a second catheter and (ii) the second anchor is disposed outside of the second catheter.

In an application, the method further includes anchoring a fourth portion of the tubular member to the tissue of the atrium (1) by driving a third anchor from inside the tubular member through the tubular member and into the tissue of the atrium, and (2) such that a fifth portion of the tubular member, disposed between the second portion and the fourth portion, traverses the valve and restricts a movement of the at least one leaflet.

In an application:

the implant includes a linking member that extends, outside of the tubular member, from a first linking site of the tubular member between the first portion and the second portion, to a second linking site of the tubular member between the second portion and the fourth portion, and advancing includes advancing the implant in a generally straight configuration in which at least part of the linking member is disposed alongside the tubular member.

In an application, the method further includes moving the implant into an A-shape having a first stem, a second stem, and a crossbar, the first stem defined by the third portion of the tubular member, the second stem defined by the fifth portion of the tubular member, and the crossbar defined by the linking member.

In an application, the method further includes adjusting a length of the linking member between the first linking site and the second linking site.

In an application, the implant includes a locking mechanism, and the method further includes fixing the length by locking the locking mechanism to the linking member.

In an application, adjusting the length includes sliding a portion of the linking member within the lumen.

There is further provided, in accordance with an application of the present invention, a method for use with a native valve of a heart of a subject, the method including:

advancing an implant into the heart; and coupling the implant to a carabiner of a tissue anchor that is coupled to tissue of the heart.

The present invention will be more fully understood from the following detailed description of applications thereof, taken together with the drawings, in which:

BRIEF DESCRIPTION OF THE DRAWINGS

FIGS. 1A-B are schematic illustrations of an implant comprising a flexible longitudinal member such as a flexible tubular member, having been implanted at a native mitral valve of a heart of a subject, in accordance with some applications of the invention;

FIGS. 2A-G are schematic illustrations of a system and technique for implanting an implant, in accordance with some applications of the invention;

FIG. 4 is a schematic illustration of an alternative implantation arrangement of an implant, in accordance with some applications of the invention;

FIGS. 5A-F are schematic illustrations of an implant, comprising a longitudinal member and a linking member that extends from a first linking site of the longitudinal member to a second linking site of the longitudinal member, in accordance with some applications of the invention;

FIGS. 6A-B are schematic illustrations of an implant, comprising a longitudinal member and a plurality of linking members, in accordance with some applications of the invention;

FIGS. 12A-C, 13A-B, 14, 15A-B, and 16 are schematic illustrations of implants each comprising a support structure and a leaflet-restraining frame, in accordance with some applications of the invention;

DETAILED DESCRIPTION OF EMBODIMENTS

Figure 2E:
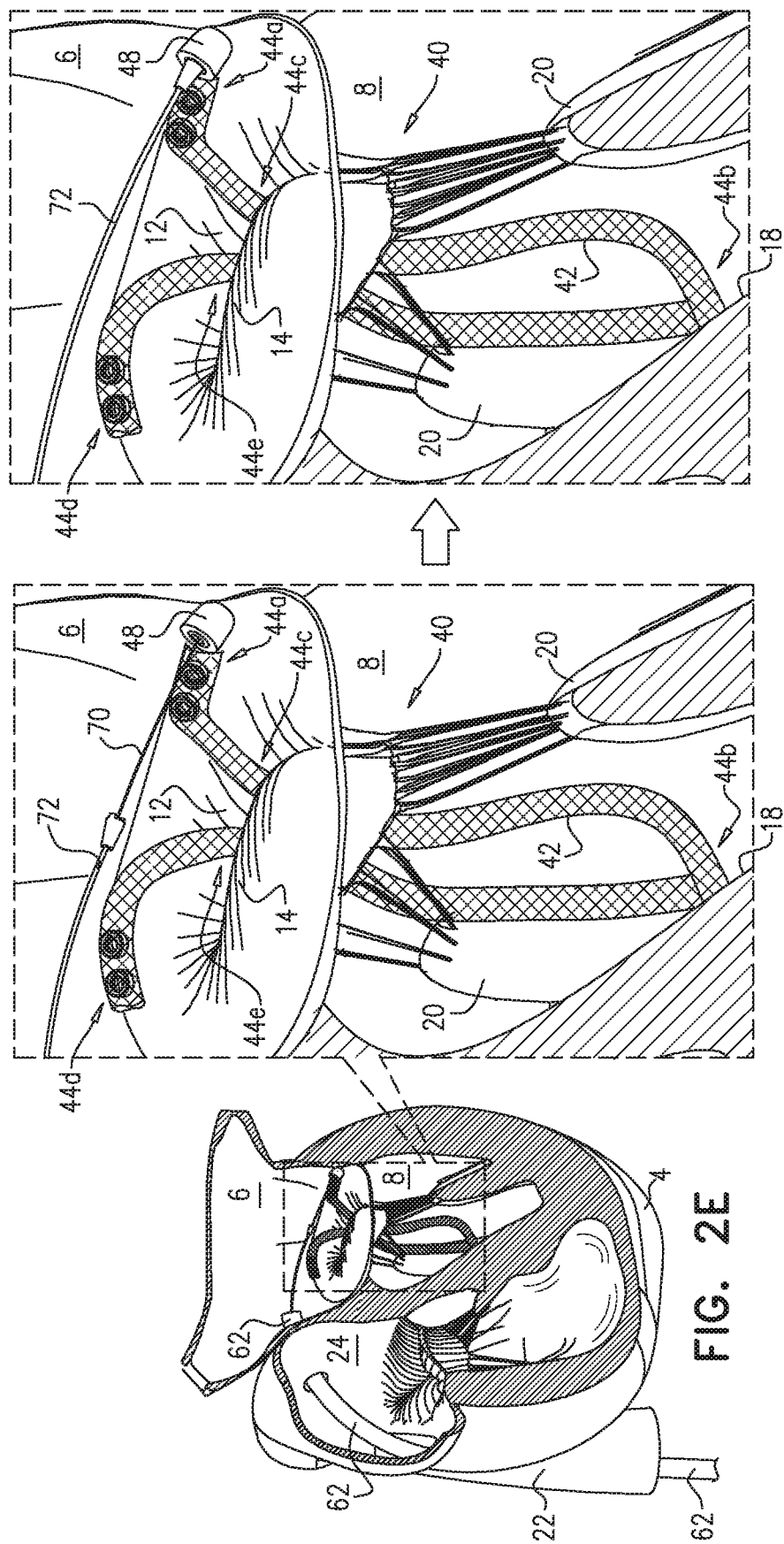

Reference is made to FIGS. 1A-B, which are schematic illustrations of an implant 40 comprising a flexible longitudinal member such as a flexible tubular member 42 (e.g., a sleeve), having been implanted at a native mitral valve 10 of a heart 4 of a subject, in accordance with some applications of the invention. FIG. 1A shows implant 40 being used to treat a prolapsing posterior leaflet 12 of valve 10, and FIG. 1B shows the implant being used to treat a prolapsing anterior leaflet 14 of the valve.

The longitudinal member (e.g., tubular member 42) of implant 40 extends from a site within left atrium 6 of the heart to a site within left ventricle 8 of the heart, such that it traverses valve 10 and inhibits movement of at least one leaflet of the valve (e.g., inhibits movement of the leaflet into atrium 6)—i.e., restrains the leaflet. That is, a first portion 44a of member 42 is anchored within atrium 6 (e.g., to mitral annulus 16, or to the wall of the atrium), a second portion 44b of member 42 is anchored within ventricle 8 (e.g., to a ventricular wall 18, or to a papillary muscle 20), and a third portion 44c of member 42, disposed between portions 44a and 44b, traverses valve 10 and inhibits movement of the at least one leaflet, e.g., posterior leaflet 12 (FIG. 1A) or anterior leaflet 14 (FIG. 1B).

Typically, the longitudinal member (e.g., tubular member 42) extends back from the ventricular site into the atrium, such that it traverses valve 10 again (e.g., at another site), further inhibiting movement of the at least one leaflet (e.g., movement of the leaflet into atrium 6). That is, a fourth portion 44d of member 42 is anchored within atrium 6 (e.g., to mitral annulus 16, or to the wall of the atrium), and a fifth portion 44e of member 42, disposed between portions 44c and 44d, traverses valve 10 and inhibits movement of the at least one leaflet.

Figure 18:
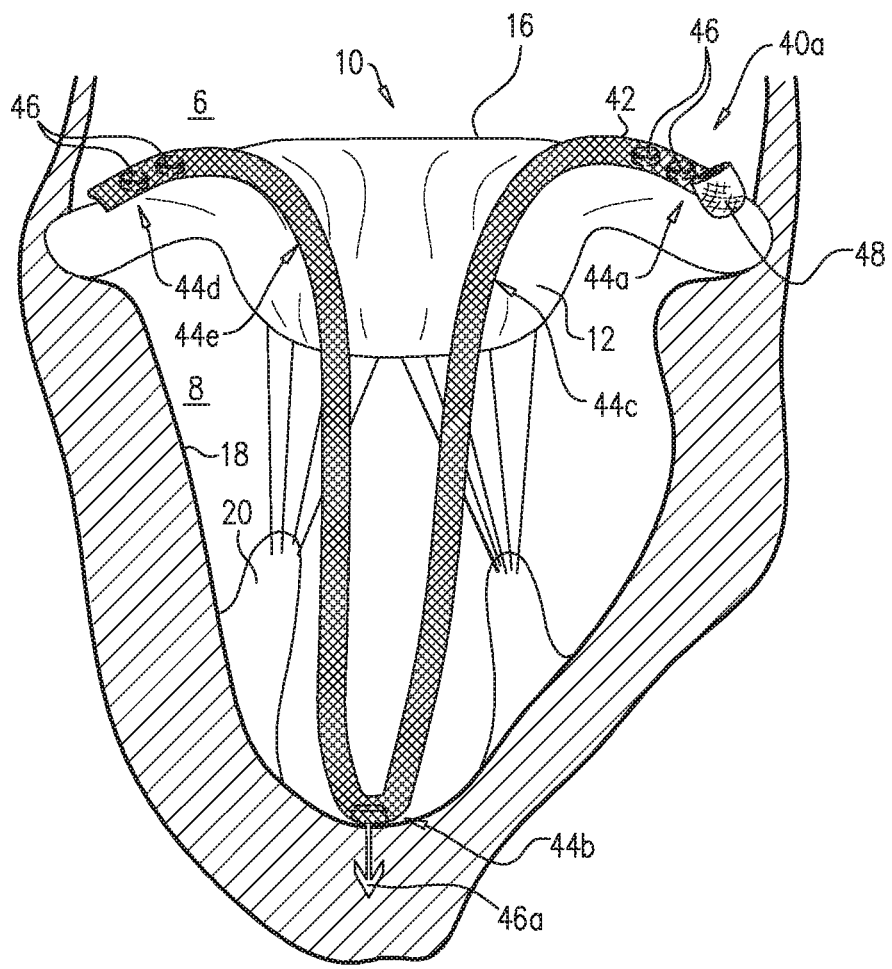
FIG. 18 is a schematic illustration of an implant comprising a flexible longitudinal member such as flexible tubular member, in accordance with some applications of the invention.

Each portion 44 that is anchored to tissue of the heart (e.g., portions 44a, 44b and 44d) is anchored using at least one tissue anchor 46. For example, as shown in FIGS. 1A and 1B, portions 44a and 44d may each be anchored using a respective plurality of tissue anchors, and portion 44b may be anchored using a single tissue anchor. However, other number of tissue anchors may be used as appropriate, including but not limited to, the number of tissue anchors shown in other figures of the present application, mutatis mutandis. Typically, and as shown, each tissue anchor 46 comprises an anchor head disposed within lumen 45, and a tissue-engaging element disposed outside of the lumen, and configured to penetrate and anchor to tissue of the heart. Tissue anchors 46 are shown as helical tissue anchors purely for illustrative purposes, and may comprise any suitable tissue anchor known in the art, such as dart-like tissue anchors or staples. For example, FIG. 18 shows implant 40 having been implanted at native valve 10 using dart-like tissue anchors 46a, in accordance with some applications of the invention.

Therefore, each portion 44 that is anchored to tissue of the heart (e.g., portions 44a, 44b and 44d) serves as an anchor site of the longitudinal member, and each portion 44 that extends between these anchor sites (e.g., portions 44c and 44e) serves as a longitudinal portion. For some applications, and as shown, the longitudinal portions form a V-shape, e.g., disposed with respect to each other at an angle of less than 150 degrees and/or greater than 10 degrees (e.g., between 110 and 30 degrees).

For applications in which the longitudinal member comprises tubular member 42, lumen 45 typically provides fluid communication between portions 44a, 44b, and 44d, and thereby also between the anchor heads of the tissue anchors 46 that anchor these portions of the longitudinal member to tissue.

Typically, a distance along the longitudinal member (e.g., along tubular member 42) between the tissue anchor 46 that anchors portion 44a and the tissue anchor that anchors portion 44b is greater than 1 cm and/or less than 6 cm (e.g., 1-6 cm, such as 1.5-3 cm). Typically, a distance along the longitudinal member (e.g., along tubular member 42) between the tissue anchor 46 that anchors portion 44b and the tissue anchor that anchors portion 44d is greater than 1 cm and/or less than 6 cm (e.g., 1-6 cm, such as 1.5-3 cm).

Reference is made to FIGS. 2A-G, which are schematic illustrations of a system and technique for implanting implant 40, in accordance with some applications of the invention. A first steerable catheter 62 is advanced transluminally (e.g., transfemorally, and via inferior vena cava 22) to heart 4, into right atrium 24 of the heart, and transseptally into left atrium 6. Septal puncture is typically performed as known in the art. For some applications, septal puncture is performed using a separate sheath (not shown) along which catheter 62 is advanced.

A second steerable catheter 64, slidable through catheter 62, extends from the distal end of catheter 62. For example, catheter 64 may be introduced via a proximal end of catheter 62 subsequent to transluminal advancement of catheter 62, or catheter 62 may be advanced with catheter 64 disposed therewithin.

Catheter 62 is steerable (e.g., bendable) in a first plane, and catheter 64 is steerable in a second plane, orthogonal to the first plane. Furthermore, catheter 64 is longitudinally slidable with respect to catheter 62, i.e., along a longitudinal axis of catheter 64. This configuration facilitates three-dimensional movement of the distal end of catheter 64, and thereby a third degree of movement of the placement of tissue anchor 46. For some applications, the third dimension of movement (along the longitudinal axis of catheter 64) is alternatively or additionally provided by longitudinal sliding of channel 68 (described hereinbelow) with respect to catheter 64.

For some applications, movement of catheter 64 with respect to catheter 62 is at least partly inhibited (e.g., movement is allowed up to but not further than a degree of movement). For some applications (such as but not limited to some applications in which the third dimension of movement is provided by sliding of channel 68), longitudinal sliding catheter 64 with respect to catheter 62 is at least partly inhibited. For some applications, rotation of catheter 64 with respect to catheter 62 is at least partly inhibited. For some applications the inhibition of movement of catheter 64 with respect to catheter 62 is provided by one or more locking mechanisms comprising couplings defined by one or both of the catheters and/or controllers (e.g., handles) of the catheters. For some applications, locking mechanisms and couplings described in one or more of the following references (all of which are incorporated herein by reference) provide the inhibition of movement, mutatis mutandis:

PCT publication WO/2013/069019 to Sheps et al.;

U.S. patent application Ser. No. 14/357,040 to Sheps et al., which published as US 2014/0309661;

PCT publication WO 2014/064694 to Sheps et al.

The distal end of catheter 64 is advanced to a first tissue site (FIG. 2A), typically in atrium 6 of the subject. Typically, member 42 is placed in contact with the tissue site. Tubular member 42 comprises a flexible wall 43 that defines a lumen 45 of the tubular member. The flexible wall comprises a lateral wall that circumscribes the lumen, and for some applications also comprises a distal wall that defines a distal end of the lumen. A distal portion (e.g., a distal end) of tubular member 42 is anchored to the tissue site by a tissue anchor 46, which is driven, by an anchor manipulator 66, through the wall of the tubular member and into the tissue site out of the distal end of catheter 64. For some applications, the first anchor is driven through the distal wall. Typically, a channel 68 is disposed within member 42, and anchor manipulator 66 advances anchor 46 through the channel Channel 68 is typically longitudinally slidable within catheter 64, and, as described hereinabove, may provide a third direction of movement for placement of tissue anchor 46 (and the portion of tubular member 42 that it is used to anchor).

For some applications, implant 40 comprises an adjusting mechanism 48, such as a spool, which is described in more detail hereinbelow. For some such applications, and as shown, implant 40 is advanced through catheter 64 with mechanism 48 at a distal end of member 42. For such applications, (1) mechanism 48 may be moved laterally prior to anchoring of the tubular member, and/or (2) a guide member 70 (described in more detail hereinbelow), may extend proximally from mechanism 48 and into catheter 64 (e.g., into a secondary lumen thereof). It is to be noted that although the implants described herein are generally shown with adjusting mechanism 48, the scope of the invention includes otherwise identical implants without the adjusting mechanism.

Subsequently to the anchoring, (1) channel 68 (and typically also catheter 64) is withdrawn proximally with respect to tubular member 42, thereby releasing (e.g., exposing) a portion of the tubular member, and (2) the distal end of the channel (and typically also the catheter) is moved toward another tissue site at which another tissue anchor 46 will be used to anchor the tubular member (FIG. 2B). For some applications, a reference-force tube (not shown), disposed within catheter 64 proximal to member 42 provides a reference force to the proximal end of member 42, thereby facilitating the release/exposure of member 42 from channel 68 and/or catheter 64.

For some applications, and as shown in FIG. 2B, more than one tissue anchor 46 is used to anchor member 42 in the atrium (e.g., to annulus 16), before moving the distal ends of catheter 64 and channel 68 into ventricle 8. The tubular member is progressively exposed from catheter 64 and channel 68, and anchors 46 are driven through the progressively proximal portions of tubular member 42 that become exposed. FIG. 2B shows first portion 44a of member 42 having been anchored in the atrium by two tissue anchors, and portion 44c having become exposed from catheter 64 as the distal end of the catheter is moved into ventricle 8.

FIG. 2C shows the distal end of catheter 64 and channel 68 having been moved to a tissue site within ventricle 8. Anchor manipulator 66 is used to anchor portion 44b to this ventricular tissue site. Subsequently, more of tubular member 42 is exposed as the distal ends of catheter 64 and channel 68 are moved back into atrium 6, and portion 44e is anchored to a tissue site within the atrium (e.g., to the annulus) (FIG. 2D).

Typically, the longitudinal member (e.g., tubular member 42) is anchored to the tissue sites such that a longitudinal member is generally slack (e.g., a distance along the longitudinal member between a tissue anchor in the atrium and a tissue anchor in the ventricle is greater than a shortest straight-line distance between those tissue anchors). It is hypothesized that the slack facilitates implantation of implant 40 while generally not deforming tissue and/or affecting hemodynamics (at least not during implantation), which is hypothesized to increase safety of the procedure.

For some applications, the longitudinal member is anchored with more slack than will be desired in a final state of the longitudinal member, and is subsequently contracted. For some such applications, and as shown, implant 40 comprises adjusting mechanism 48 (e.g., an actuatable adjusting mechanism), such as a spool, ratchet, or other adjusting mechanism. Adjusting mechanism 48 typically includes a locking element that locks the adjusting mechanism subsequently to adjustment. For some such applications, and as shown in FIG. 2D, guide member 70 remains coupled to mechanism 48 after anchoring of the longitudinal member (e.g., tubular member 42).

Figure 2F:
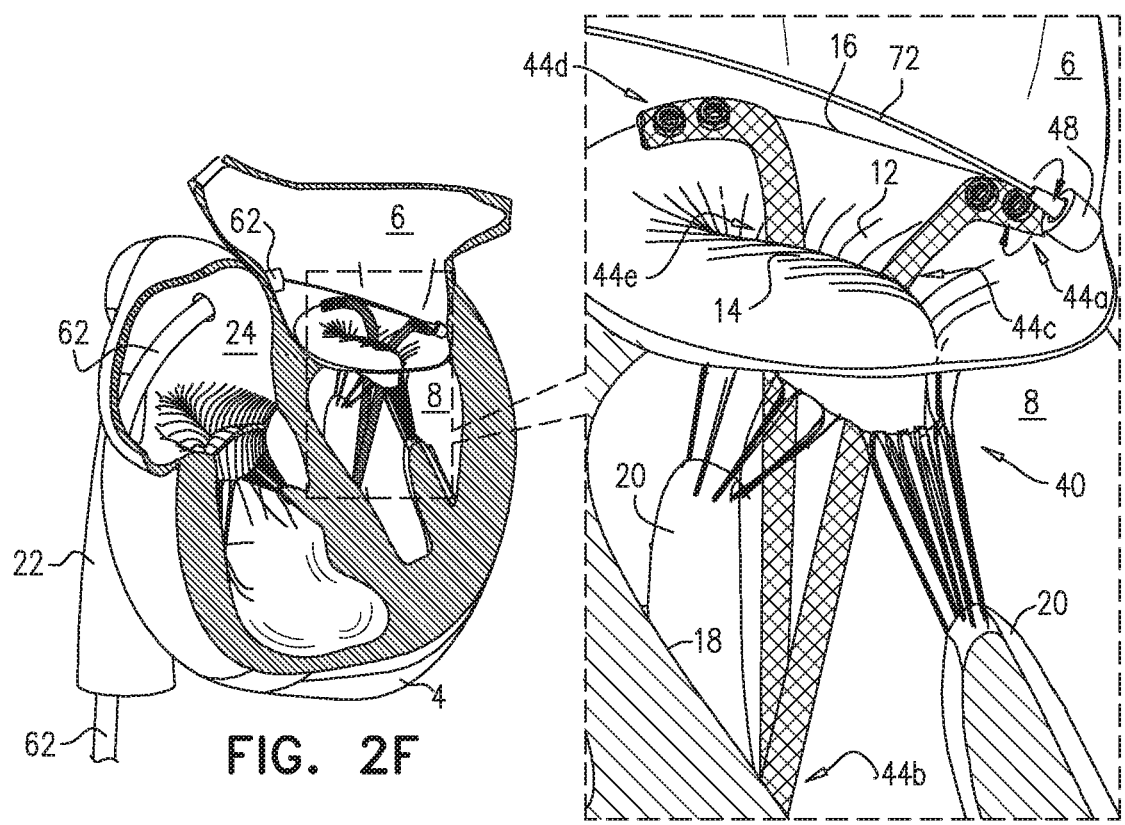

FIGS. 2E-F show an actuating tool 72 being advanced along guide member 70 to adjusting mechanism 48, and being used to actuate the adjusting mechanism so as to contract tubular member 42. For some applications, and as shown, catheter 64 is withdrawn before advancement of tool 72, leaving guide member 70 in place (e.g., the catheter is slid proximally along and off of a proximal end of the guide member), such that tool 72 is advanced through catheter 62 but not through catheter 64. Alternatively, tool 72 may be advanced through catheter 64.

For some applications, adjusting mechanism 48 is coupled to a contracting wire 49 (shown in FIG. 1A) that extends along (e.g., through) at least part of tubular member 42. For applications in which adjusting mechanism 48 comprises a spool, as shown, tool 72 rotates the adjusting mechanism, thereby contracting the tubular member by tensioning contracting wire 49 by wrapping the contracting wire onto the spool. As described hereinabove, subsequently to the adjustment, adjusting mechanism 48 is typically locked by a locking element of the adjusting mechanism.

For some applications, instead of implant 40 comprising an actuatable adjusting mechanism, tension on the contracting wire is adjusted by pulling on a portion of the wire disposed outside of the implant (e.g., outside the body of the subject), and the tension is fixed using a locking element (e.g., that is a component of the implant).

Figure 2G:
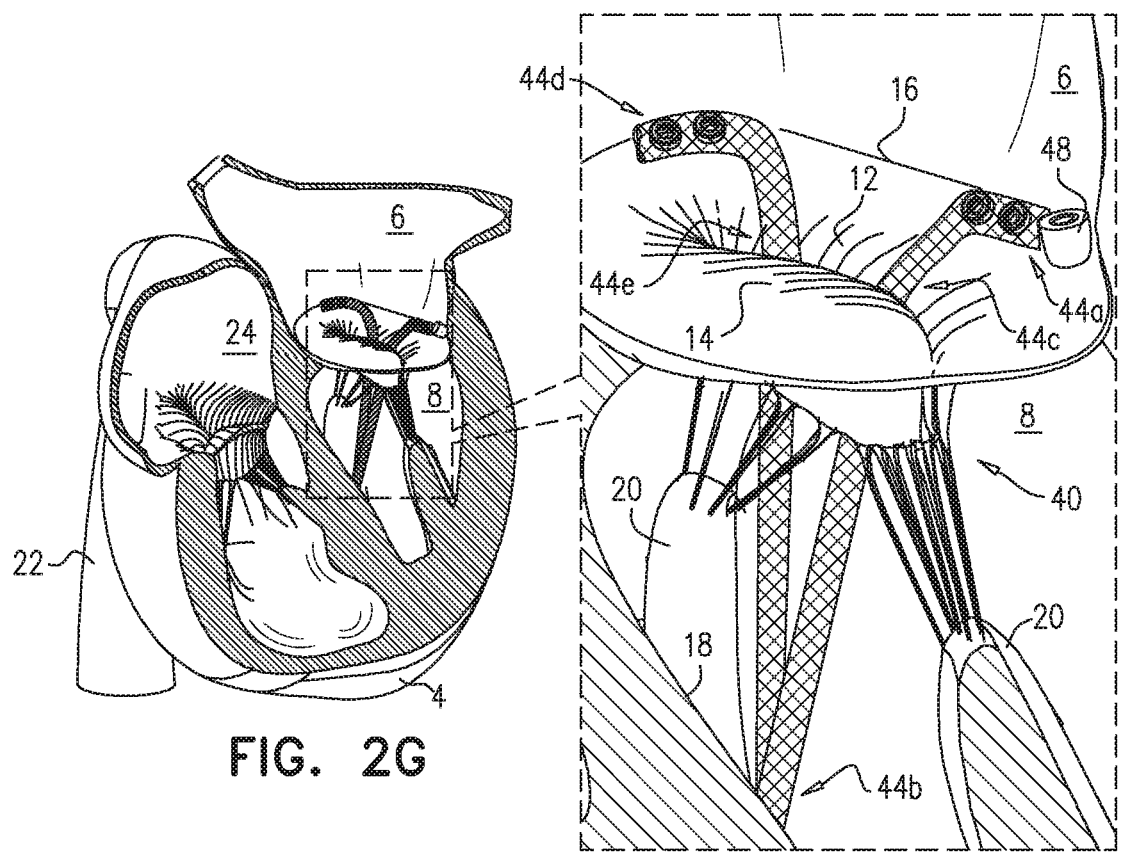

FIG. 2G shows a final state of implant 40. Actuating tool 72 has been withdrawn, and guide member 70 is typically also withdrawn. For some applications, mechanism 48 is locked, and guide member 70 is decoupled from mechanism 48, e.g., as described in PCT application publication WO/2012/176195 to Gross et al., and/or as described in US patent application publication 2014/0142695 to Gross et al., which are both incorporated herein by reference. The state of implant 40 shown in FIG. 2G corresponds to the state shown in FIG. 1A.

For some applications, apparatus and techniques described in the following references, which are incorporated herein by reference, may be used to facilitate, and/or be used in combination with, those described with reference to FIGS. 2A-F:

PCT patent application publication WO 2013/069019 to Sheps et al., entitled "Controlled steering functionality for implant-delivery tool"; and PCT patent application IL2013/050860 to Sheps et al., filed 23 Oct. 2013, entitled "Controlled steering functionality for implant-delivery tool", which published as WO/2014/064694.

For example:

Tubular member 42 of the present application may correspond to sleeve 26 of these incorporated references, mutatis mutandis.

Catheters 62 and 64 of the present application may correspond to catheters 12 and 14 of these incorporated references, and/or the apparatus and techniques for controlling the catheters of these incorporated references may be used to control the catheters of the present application, mutatis mutandis.

Channel 68 and the reference-force tube of the present application may correspond to channel 18 and reference-force tube 19 of these incorporated references, mutatis mutandis.

Adjusting mechanism 48 of the present application may correspond to adjusting mechanism 40 of these incorporated references, mutatis mutandis.

For some applications, apparatus and techniques described in US Patent Application Publication 2012/0078355 to Zipory et al., entitled "Deployment techniques for annuloplasty ring and over-wire rotation tool", which is incorporated herein by reference, may be used to facilitate, and/or be used in combination with, those described with reference to FIGS. 2A-G. mutatis mutandis. For example, adjusting mechanism 48, guide member 70, and/or actuating tool 72 of the present application may be identical respectively to adjusting mechanism 40, longitudinal member 86, and/or rotation tool 80 of US 2012/0078355 to Zipory et al., mutatis mutandis. Alternatively or additionally, the apparatus and techniques described in US 2012/0078355 to Zipory et al. for use with these elements may be used with the corresponding elements of the present application.

Figure 3:
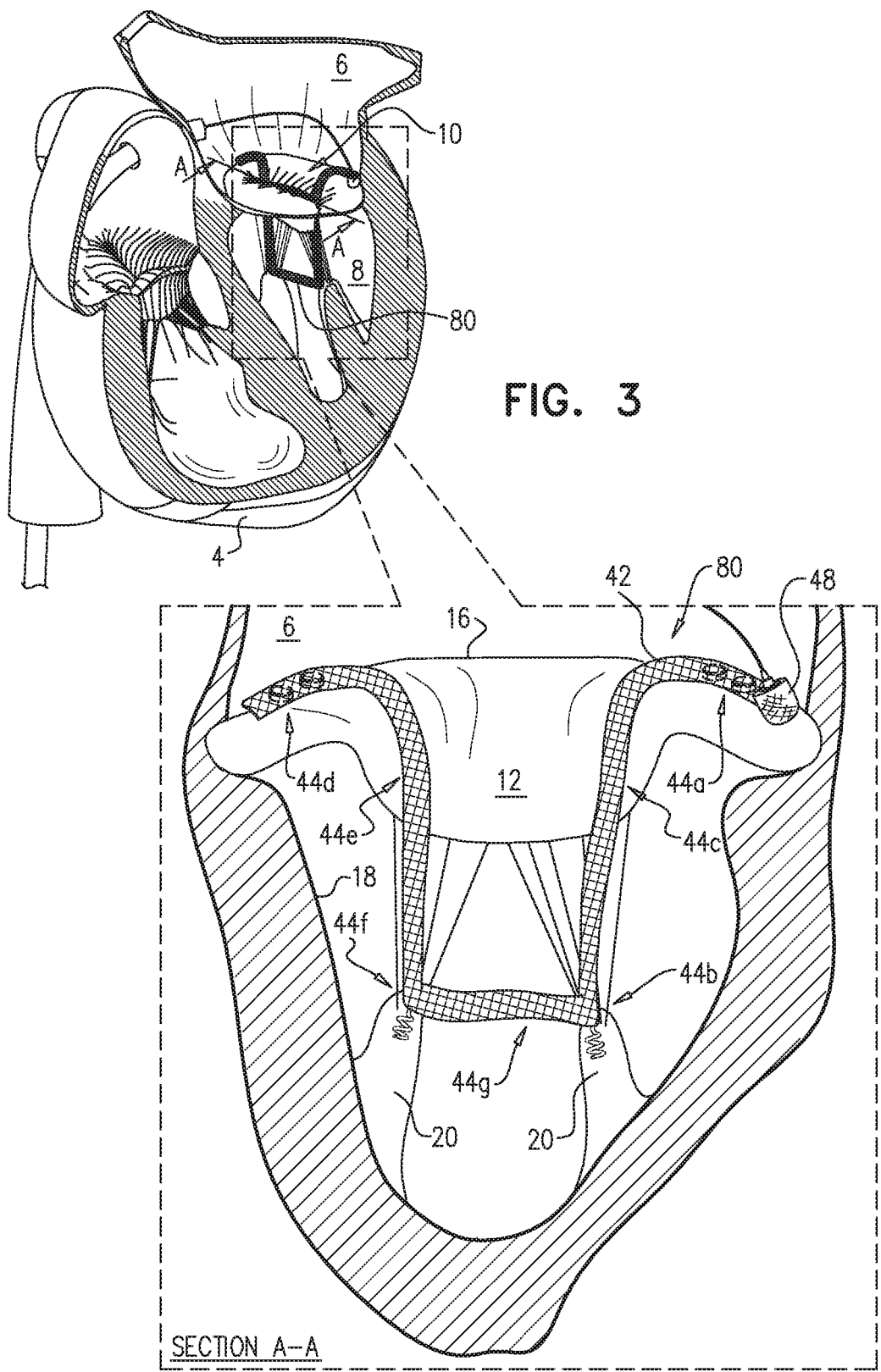
FIG. 3 is a schematic illustration of an implant having been implanted at a native valve, in accordance with some applications of the invention.

Reference is made to FIG. 3, which is a schematic illustration of an implant 80 having been implanted at valve 10, in accordance with some applications of the invention. Typically, implant 80 is identical to implant 40, although length of tubular member 42 may be different. For example, tubular member 42 of implant 80 may be longer than that of implant 40.

As shown in FIG. 3, for some applications, tubular member 42 may be anchored at more than one tissue site within ventricle 8. For example, a portion 44f of member 42 may be implanted at a second tissue with within ventricle 8, such that a portion 44g, disposed between portions 44b and 44f, extends between the two ventricular tissue sites. It is to be noted that for some applications such an implantation arrangement is distinct from an implantation arrangement in which two or more tissue anchors are used to anchor a portion of member 42 to a single ventricular site. For example, in the implantation arrangement shown in FIG. 3, portion 44g is generally not in contact with tissue of ventricle 8, whereas when two tissue anchors are used to anchor a portion of member 42 to a single ventricular site, the portion of member 42 disposed between the two tissue anchors is typically in contact with the ventricular tissue. For some applications, portions 44b and 44f of implant 80 are anchored to respective papillary muscles 20 of the subject (as shown). Alternatively, one or both of portions 44b and 44f may be anchored to wall 18 of ventricle 8.

For some applications in which portions 44b and 44f are anchored to respective papillary muscles 20, member 42 is configured to facilitate reduction of a distance between the papillary muscles, e.g., via contraction of portion 44g. For some such applications, portion 44g is contracted using adjusting mechanism 48, or a separate adjusting mechanism. For some such applications, member 42 is differentially contractible (e.g., as described hereinbelow with reference to FIG. 8, mutatis mutandis), such that portion 44g is more or less contractible than portions 44c and 44e.

It is to be noted that the locations at which portions 44c and 44e of implant 80 contact leaflet 12 are different to those at which the same portion of implant 40 contact the leaflet. Typically, these locations are spaced further apart for implant 80 due to the spacing between portions 44b and 44f. It is hypothesized that for some applications (e.g., for some subjects) this may advantageously more effectively improve coaptation of leaflet 12 with leaflet 14, such as by more effectively inhibiting atrially-directed movement of leaflet 12.

Thus, implant 80 is hypothesized to adjust functionality of the native valve by (1) restraint of a leaflet of the native valve, and/or (2) adjustment of the distance between papillary muscles.

Reference is made to FIG. 4, which is a schematic illustration of an alternative implantation arrangement of implant 80, in accordance with some applications of the invention. In the implantation arrangement shown in FIG. 4, portions 44c and 44e of tubular member 42 intercross. For such an arrangement, portion 44b is typically anchored at a ventricular site that is closer to (a) the atrial site at which portion 44d is anchored, than to (b) the atrial site at which portion 44a is anchored. For some applications, implant 80 is implanted such that a point 82 at which portions 44c and 44e intercross is disposed in front of leaflet 12, e.g., such that the point will contact the leaflet. It is hypothesized that for some applications (e.g., for some subjects) this may advantageously more effectively improve coaptation of leaflet 12 with leaflet 14, such as by more effectively inhibiting atrially-directed movement of leaflet 12 (e.g., by providing a greater area of member 42 that leaflet 12 may contact).

Reference is made to FIGS. 5A-F, which are schematic illustrations of an implant 100, comprising a longitudinal member such as a tubular member 102, and a linking member 104 that extends from a first linking site 106a of the longitudinal member to a second linking site 106b of the longitudinal member, in accordance with some applications of the invention. Typically, tubular member 102 is identical to tubular member 42, except where described otherwise. Further typically, implant 100 and its method of implantation are typically identical, except where described otherwise, to implant 40 and its method of implantation. Thus, some terms and reference numerals (such as portion 44a, portion 44b, portion 44c, portion 44d and portion 44e) used hereinabove with respect to tubular member 42, are also used with respect to tubular member 102.

FIG. 5A shows implant 100 in an implanted state at native valve 10. For some applications, and as shown, linking site 106a is located close to (e.g., within) portion 44c of member 102, and linking site 106b is located close to (e.g., within) portion 44e of member 102. For some applications, linking sites 106a and 106b are located such that, when implant 100 is implanted, linking member 104 is located in front of leaflet 12, e.g., such that the leaflet contacts the linking member. It is hypothesized that for some applications, linking member 104 facilitates restraining of leaflet 12 (i.e., inhibition of movement of the leaflet into atrium 6) by inhibiting movement of the leaflet between portions 44c and 44e, such as by inhibiting movement of portions 44c and 44e away from each other, and/or directly obstructing the leaflet.

For some applications, linking member 104 is configured (e.g., coated) to inhibit tissue growth thereon. For some applications, linking member 104 is configured (e.g., coated) to promote tissue growth thereon.

In the implanted state, a distance d1 between linking sites 106a and 106b, measured along the longitudinal member (e.g., tubular member 102) is greater than a distance d2 between the linking sites, measured along the linking member. For example, distance d1 may be more than 20 percent greater (e.g., more than 50 percent greater) than distance d2. In the implanted state, a mid-portion 108 of linking member 104 is disposed outside of, and not in contact with, tubular member 102. For example, mid-portion 108 of linking member 104 may be more than 10 mm, such as more than 15 mm away from tubular member 102. In the implanted state, typically at least 0.5 cm (e.g., 0.5-4 cm) of linking member 104 are disposed outside of, and not in contact with, tubular member 102.

Figure 5B:
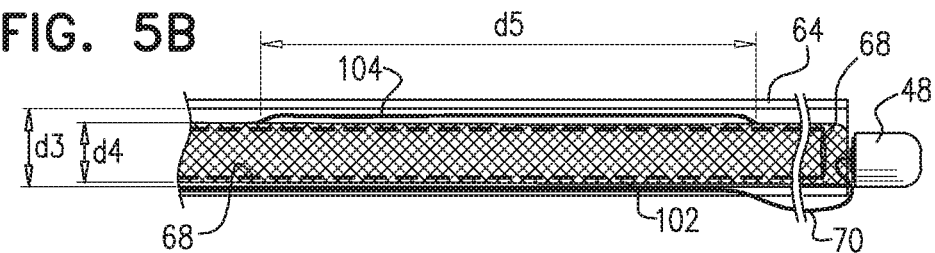

FIG. 5B shows implant 100, in a delivery state thereof, within catheter 64. In the delivery state, the longitudinal member (e.g., tubular member 102) is coaxial with catheter 64, and at least a portion of linking member 104 is disposed alongside the longitudinal member (e.g., generally parallel with the longitudinal member, such as along the outside of tubular member 102). Typically, therefore, a distance d5 between linking sites 106a and 106b, measured along linking member 104, is no smaller than a distance between the linking sites measured along the longitudinal member (e.g., distance d1). For some applications, distance d5 is less than 20 percent different (e.g., less than 10% different, such as less than 5 percent different) from distance d1. That is, for some applications the portion of linking member 104 that is disposed outside of tubular member 102 has a length d5 that is less than 20 percent different (e.g., less than 10% different, such as less than 5 percent different) to the length of the tubular member between the linking sites. For example, length d5 may be generally equal to (e.g., within 10 mm of) length d1.

For some applications, distance d5 is greater than distance d1 (e.g., linking member 104 may be meander back and forth alongside and/or around a portion of tubular member 102). For some such applications, distance d5 may be more than 20 percent greater than distance d1.

For some applications, the portion of linking member 104 that is disposed alongside the longitudinal member is generally within 2 mm (e.g., within 1 mm, such as within 0.5 mm) of the longitudinal member, such as being generally in contact with the longitudinal member.

Figure 5C:
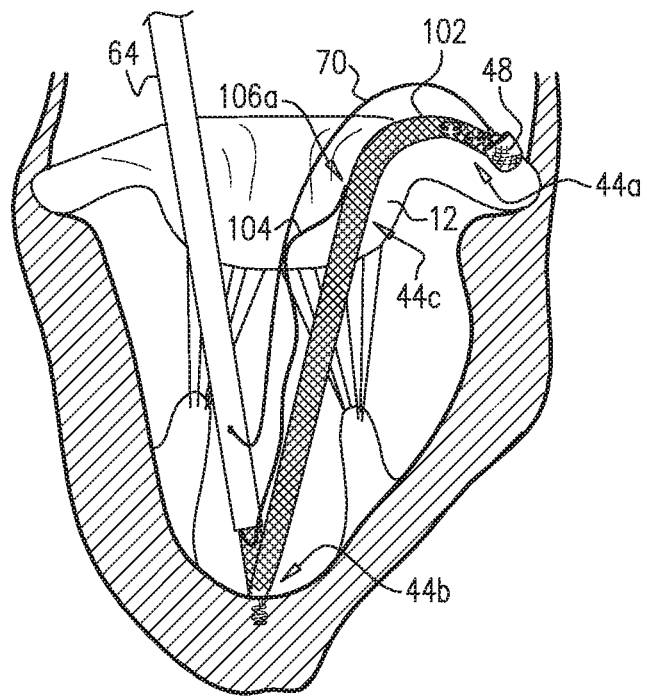
Figure 5D:
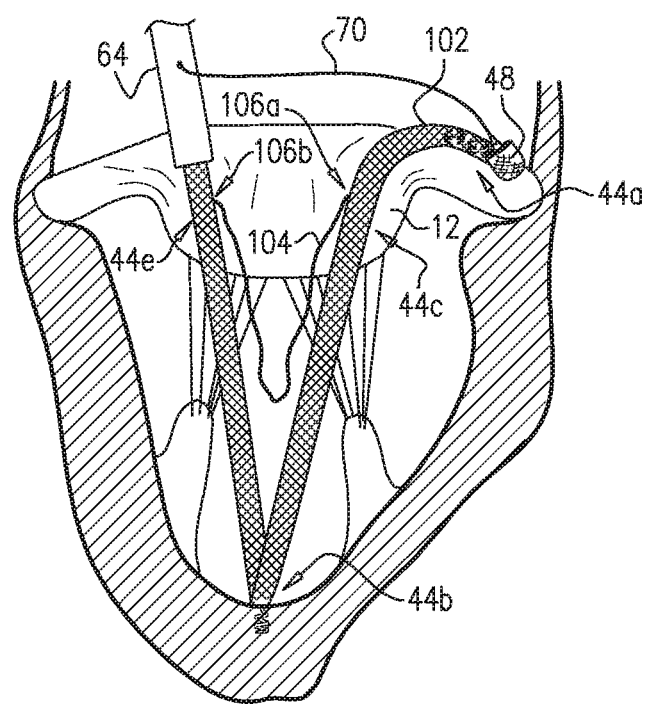
Figure 5E:
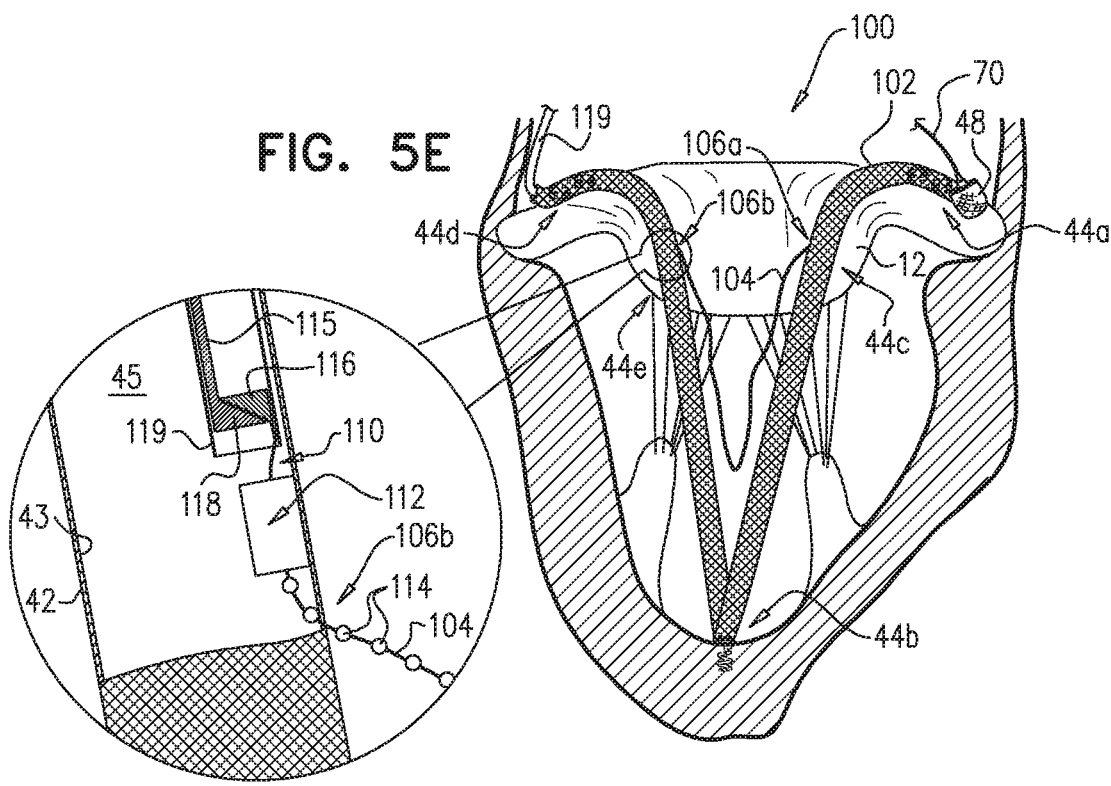

FIGS. 5C-E show steps in the implantation of implant 100. Portion 44a (i.e., a distal portion) of tubular member 102 is anchored to a first tissue site (e.g., an atrial tissue site, such as described hereinabove for tubular member 42, mutatis mutandis) while almost all, if not all, of tubular member 102 is disposed within catheter 64. Therefore, portion 44a is anchored while both linking site 106a and linking site 106b are disposed within catheter 64.

Subsequently, tubular member 102 is advanced out of catheter 64 (thereby exposing portion 44c and linking site 106a), the distal end of catheter 64 is moved to a second tissue site (e.g., a ventricular tissue site), and portion 44b is anchored to the second tissue site (FIG. 2C). During the anchoring of portion 44b, linking site 106a is typically disposed outside of catheter 64, and linking site 106b is typically disposed within the catheter.

Subsequently, tubular member 102 is advanced further out of catheter 64, thereby exposing portion 44e and linking site 106b (FIG. 5D). Portion 44d is subsequently anchored to a third tissue site (e.g., an atrial tissue site) (FIG. 5E). During the anchoring of portion 44d, both linking site 106a and linking site 106b are typically disposed outside of catheter 64.

Figure 5F:
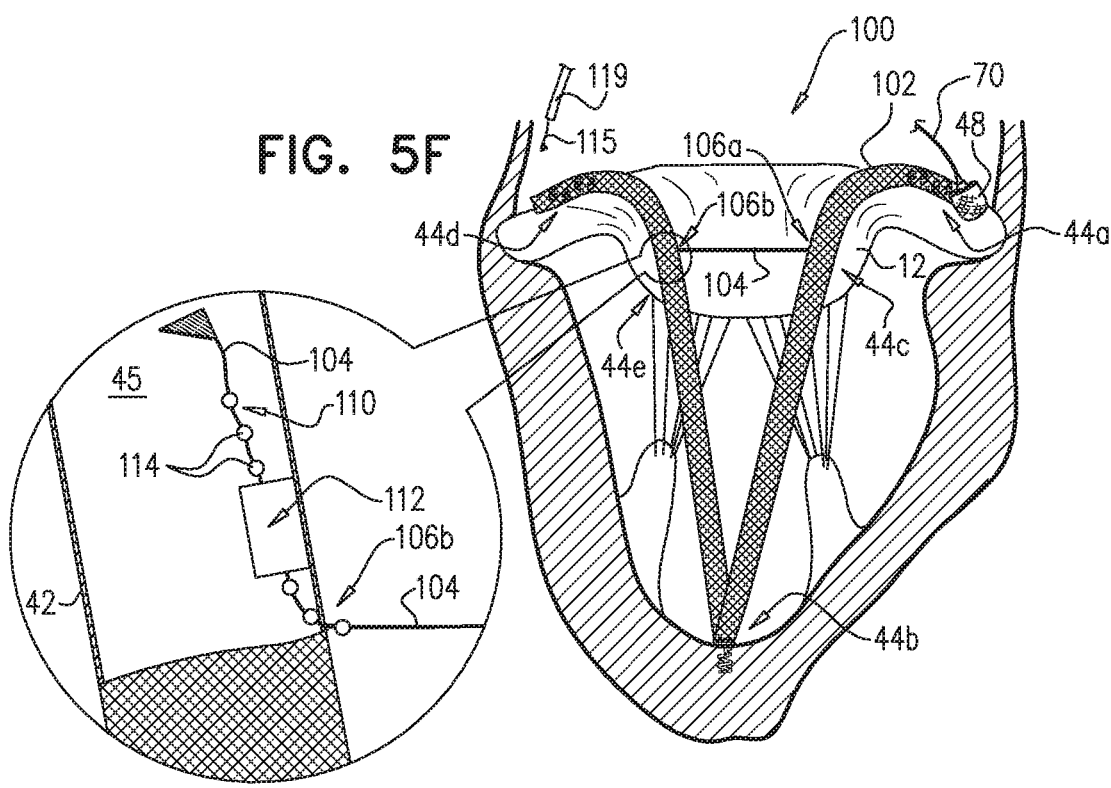

For some applications, and as shown in FIG. 5E, the length of the portion of linking member 104 that is disposed outside of tubular member 102 (i.e., the distance between the linking sites, measured along the linking member) remains generally the same after anchoring of the tubular member, and is subsequently (e.g., manually) reduced. FIGS. 5E-F shows an exemplary technique by which this length is reduced. A proximal portion 110 of linking member 104 is slidable with respect to the longitudinal member (e.g., tubular member 102) at linking site 106b, such as by being slidable through wall 43 of the tubular member and into lumen 45. The length is reduced by pulling portion 110 of linking member 104, e.g., until the length becomes length d2.

Typically, a locking mechanism 112 inhibits linking member 104 from sliding back in the opposite direction (and thus increasing its length between the linking sites). For some applications, locking mechanism 112 is manually locked to linking member 104 (e.g., by crimping). For some applications, locking mechanism 112 comprises a ratcheting mechanism, and linking member 104 is coupled to or defines one or more protrusions 114 which are configured to pass through the locking mechanism in one direction, but which are inhibited by the locking mechanism from passing in the opposite direction.

For some applications, proximal portion 110 is reversibly coupled to a pull-wire 115, which extends proximally (e.g., out of the body of the subject) such that an operating physician may reduce the length of the portion of linking member 104 that is disposed outside of tubular member 102 by pulling on the pull-wire. For example, pull wire 115 and proximal portion 110 may define respective mating surfaces 116 and 118, which are held together by an overtube 119. Once reduction of the length is complete, overtube 119 is withdrawn proximally such that surfaces 116 and 118 may decouple, and the overtube and the pull-wire are withdrawn (FIG. 5F).

For some applications, the length of the portion of linking member 104 that is disposed outside of tubular member 102 (i.e., the distance between the linking sites, measured along the linking member) reduces automatically during implantation. For example, linking member 104 may be elastic, and configured to automatically contract as the direct distance between linking sites 106a and 106b is reduced during implantation. Alternatively or additionally, proximal portion 110 may be reversibly coupled to channel 68, and is progressively pulled as the channel is progressively withdrawn during implantation (e.g., as each anchor is anchored).

For some applications, a distal portion of linking member 104 is slidable with respect to the longitudinal member (e.g., tubular member 102) at linking site 106a, such as by being slidable through wall 43 of the tubular member and into lumen 45. For some such applications, the length of the portion of linking member 104 between sites 106a and 106b is reduced using techniques described hereinabove with respect to FIGS. 5E-F. For some applications, linking member 104 is coupled to adjusting mechanism 48, and the length is automatically reduced when the adjusting mechanism is used to contract the longitudinal member (e.g., tubular member 102). Alternatively, a separate adjusting mechanism may be provided for reducing the length of the portion of linking member 104 between the linking sites. Therefore, for some applications, the implant has two (or more) adjustment points, adjustment-locking points, and/or adjustment mechanisms.

For some applications, the reduction of the length of the portion of linking member 104 between the linking sites does not significantly tension the linking member (e.g., the reduction of the length does not significantly move linking sites 106a and 106b closer to each other, and/or does not directly apply a pulling force to tubular member 102). For some such applications, distance d2 is greater (e.g., a little greater) than a direct distance between the linking sites (i.e., linking member 104 has some slack).

For some applications, the reduction of the length of the portion of linking member 104 between the linking sites does tension the linking member (e.g., moving linking sites 106a and 106b closer to each other, and/or applying a pulling force to tubular member 102). For such applications, distance d2 is typically equal to the direct distance between the linking sites. Movement of linking sites 106a and 106b closer to each other may be extracorporeally detected using imaging techniques. For example, a radiopaque marker may be disposed at each of the linking sites, and detected using fluoroscopy.

For some applications implantation of implant 100 comprises moving the implant into an A-shape (shown as an inverted A-shape in FIG. 5F) having a first stem (e.g., defined by portion 44c), a second stem (e.g., defined by portion 44e), and a crossbar (e.g., defined by linking member 104). It is to be noted that, although contraction of tubular member 102 is not shown in FIGS. 5A-F, such contraction may be performed before or after the reduction of the length of the portion of linking member 104 between the linking sites.

For some applications, a distance along the longitudinal member (e.g., along tubular member 102) between portion 44a and portion 44b is greater than 1 cm and/or less than 6 cm (e.g., 1-6 cm, such as 1.5-3 cm). For some applications, linking site 106a is disposed greater than 0.5 cm and/or less than 4 cm (e.g., 1-3 cm) along the longitudinal member (e.g., along tubular member 102) from portion 44a. For some applications, linking site 106a is disposed greater than 1 cm and/or less than 5 cm (e.g., 2-4 cm) along the longitudinal member from portion 44b.

For some applications, a distance along the longitudinal member (e.g., along tubular member 102) between portion 44b and portion 44d is greater than 1 cm and/or less than 6 cm (e.g., 1-6 cm, such as 1.5-3 cm). For some applications, linking site 106b is disposed greater than 0.5 cm and/or less than 4 cm (e.g., 1-3 cm) along the longitudinal member (e.g., along tubular member 102) from portion 44d. For some applications, linking site 106*b* is disposed greater than 1 cm and/or less than 5 cm (e.g., 2-4 cm) along the longitudinal member from portion 44*b*.

Reference is made to FIGS. 6A-B, which are schematic illustrations of an implant 120, comprising a longitudinal member such as a tubular member 122, and a plurality of linking members 124, in accordance with some applications of the invention. Each linking member 124 extends from a respective first linking site 126*a* of the longitudinal member to a respective second linking site 126*b* of the longitudinal member, in accordance with some applications of the invention. FIGS. 6A-B show implant 120 comprising a first linking member 124*a* and a second linking member 124*b*. Linking member 124*a* extends from a first linking site 126*a*' to a second linking site 126*b*', and linking member 124*b* extends from a first linking site 126*a*" to a second linking site 126*b*".

Typically, tubular member 122 is identical to tubular member 42 and/or tubular member 102, except where described otherwise. For example, tubular member 122 may be longer than, but otherwise identical to, tubular member 42 and/or tubular member 102. Further typically, implant 120 and its method of implantation are typically identical, except where described otherwise, to implant 40 and its method of implantation, and/or implant 100 and its method of implantation, mutatis mutandis. Thus, some terms and reference numerals (such as portion 44*a*, portion 44*b*, portion 44*c*, portion 44*d* and portion 44*e*) used hereinabove with respect to tubular member 42 and/or tubular member 102, are also used with respect to tubular member 122.

Portions 44*a*, 44*b*, and 44*d* of tubular member 122 are typically anchored in the manner described hereinabove for the corresponding portions of tubular member 42 and/or tubular member 102, mutatis mutandis, such that portions 44*c* and 44*e* traverse native valve 10. Subsequently, a portion 44*h* is anchored within ventricle 8 (e.g., to wall 18, or to papillary muscle 20), such that a portion 44*i* traverses valve 10. Further subsequently, a portion 44*j* is anchored within atrium 6 (e.g., to mitral annulus 16, or to the wall of the atrium), such that a portion 44*k* traverses valve 10.

As portions 44*i*, 44*h*, 44*k*, and 44*j* are progressively advanced out of catheter 64, linking member 124*b* is also progressively advanced out of the catheter, as described hereinabove with respect to linking member 104 of implant 100. For example, during the anchoring of portion 44*h* linking site 126*a*" is typically disposed outside of catheter 64, and linking site 106*b*" is typically disposed within the catheter, and during the anchoring of portion 44*j* both of these linking sites are typically disposed outside of the catheter.

FIG. 6A shows implant 120 following anchoring of portions 44*a*, 44*b*, 44*d*, 44*h*, and 44*j*. For some applications, and as shown in FIG. 6B, the length of linking members 124*a* and 124*b* disposed between their respective linking sites is subsequently reduced, e.g., as described hereinabove for linking member 104 of implant 100. For some applications, these portions of linking members 124*a* and 124*b* are shortened simultaneously. For some such applications, linking members 124*a* and 124*b* are defined by a continuous cord (e.g., that passes within tubular member 122 between linking sites 126*b*' and 126*a*"). For some applications, these portions of the linking members are shortened independently of each other. For some applications, these portions of the linking members are shortened using techniques described hereinabove with respect to linking member 104, mutatis mutandis, such as by using a locking mechanism, adjusting mechanism 48, and/or at least one separate adjusting mechanism.

Therefore, for some applications implants described herein are adjustable (i) by contracting its tubular member, and (ii) by tensioning its contracting member(s). For some applications, one or more (e.g., both) of these adjustments are performed using a respective adjusting mechanism such as (or similar to) adjusting mechanism 48. For some applications, both of these adjustments are performed using a common adjusting mechanism that provides separate control over contracting wire 49 and the linking member(s). For example, the adjusting mechanism may comprise separate spools that share common features such as a common housing and/or a common guide member 70. For some applications, the contraction wire and/or linking member are manually tensioned (e.g., using a pull-wire reversibly coupled thereto), and locked to maintain the tension.

It is to be noted that although adjusting mechanism 48 is described as comprising a spool, the scope of the invention includes the use of other adjusting mechanisms, such as a ratchet.

Typically, the reduction of the length of the portions of the respective linking members between the respective linking sites applies tension to the linking member (e.g., thereby moving linking sites 126*a*' and 126*a*" closer to linking sites 126*b*' and 126*b*", respectively, and/or moving portions 44*a* and 44*j* closer to portion 44*d*, as indicated by the arrows).

For some applications, and as shown in FIGS. 6A-B, linking site 126*a*' is disposed close to (e.g., within) portion 44*a* of member 102, linking sites 126*b*' and 126*a*" are disposed close to (e.g., within) portion 44*d*, and linking site 126*b*" is disposed close to (e.g., within) portion 44*j*. For some applications, and as shown, the linking sites are located such that, when implant 120 is implanted, linking members 124*a* and 124*b* are located upstream and/or superior to leaflet 12, such as close to (e.g., against) annulus 16. For some such applications, tensioning of the linking members thereby draws portions 44*a*, 44*d* and 44*j*, and the tissue sites to which they are anchored, closer to each other (FIG. 6B). (It is to be noted that the anchors 46 that anchor these portions to their respective tissue sites are also drawn closer to each other.) Thus, for some applications, implant 120 serves as an annuloplasty device.

Although the longitudinal member (e.g., tubular member 122) of implant 120 is shown having four portions that traverse the native valve (portions 44*c*, 44*e*, 44*i*, and 44*k*), it is to be noted that the longitudinal member may have more or fewer such valve-traversing portions. For example, the longitudinal member may have two such portions, and implant 120 may resemble implant 100, with the linking member positioned differently. Alternatively, the longitudinal member may have more than four valve-traversing portions (e.g., six or more, e.g., eight or more, and/or between six and twelve) valve-traversing portions.

For some applications, and as shown in FIGS. 6A-B, a respective linking member 124 extends between every atrially-anchored portion of the longitudinal member and all of its neighboring (i.e., adjacent) atrially-anchored portions (i.e., to its only neighboring atrially-anchored portion, or to both of its neighboring atrially-anchored portions). For some applications, some of these linking members are absent, i.e., not every atrially-anchored portion is linked to all of its neighbors via a linking member.

Figure 7:
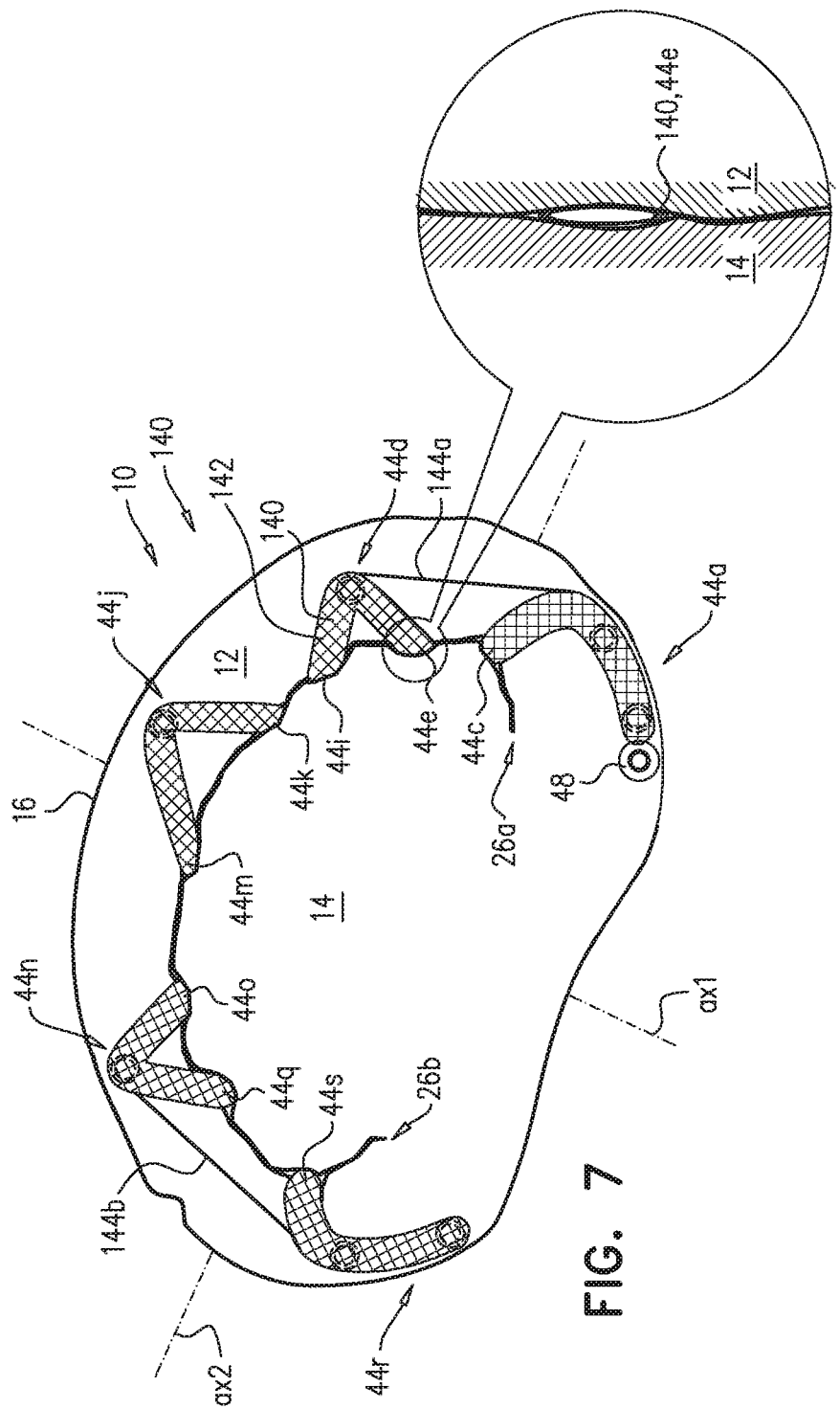
FIG. 7 is a schematic illustration of an implant, comprising a longitudinal member and one or more linking members, in accordance with some applications of the invention.

Reference is now made to FIG. 7, which is a schematic illustration of an implant 140, comprising a longitudinal member such as a tubular member 142, and one or more linking members 144, in accordance with some applications of the invention.

As described hereinabove with reference to FIGS. 6A-B, for some applications, the longitudinal member (e.g., the tubular member) of the implant has more than four valve-traversing portions, and for some applications, not every atrially-anchored portion of the longitudinal member is linked to all of its neighbors via a linking member. The longitudinal member (e.g., tubular member 142) of implant 140 has five atrially-anchored portions (portions 44a, 44d, 44j, 44n, and 44r), and eight valve-traversing portions (portions 44c, 44e, 44i, 44k, 44m, 44o, 44q, and 44s).

A first linking member 144a links atrially-anchored portions 44a and 44d, and a second linking member 144b links atrially-anchored portions 44n and 44r. Portion 44j is not linked via a linking member to either of its neighbors (portions 44d and 44n), and each of portions 44d and 44n is thereby linked via a linking member to only one of its neighbors. It is hypothesized that, for some applications, drawing portion 44a toward portion 44d, and drawing portion 44r toward portion 44n advantageously reshapes native valve 10 such that coaptation of leaflets 12 and 14 is improved and/or regurgitation is reduced. For example, it is hypothesized that, for some applications, reduction of a dimension of native valve 10 along an anterior-posterior (e.g., septo-lateral) axis ax1 of the valve is more effective in improving coaptation and/or reducing regurgitation, than is reduction of a dimension of the valve along an intercommissural axis ax2 of the valve.

In the cutaway of FIG. 7, at least a portion of tubular member 142 is shown as flattened. That is, although the tubular member defines a lumen (and may have a circular cross-section) during advancement of anchors therethrough, implantation of the tubular member may cause or allow at least a portion of the tubular member to become somewhat flattened, thereby narrowing the lumen. For some applications the lumen becomes non-circular. For some applications, contact is made between opposing sides of the sleeve (i.e., of the lateral wall of the sleeve that defines and circumscribes the lumen of the sleeve). For some applications, the flattening occurs due to tissue pressing against the sleeve. For example, the sleeve passes between leaflets 12 and 14 of the valve, and the leaflets press against the sleeve (e.g., during ventricular systole). For some applications, the flattening occurs because of longitudinal tension applied to the sleeve (e.g., during anchoring, or subsequently). For some applications, the sleeve is pre-shaped (e.g., ironed) to assume a flattened state in the absence of channel 68 therewithin.

Figure 8:
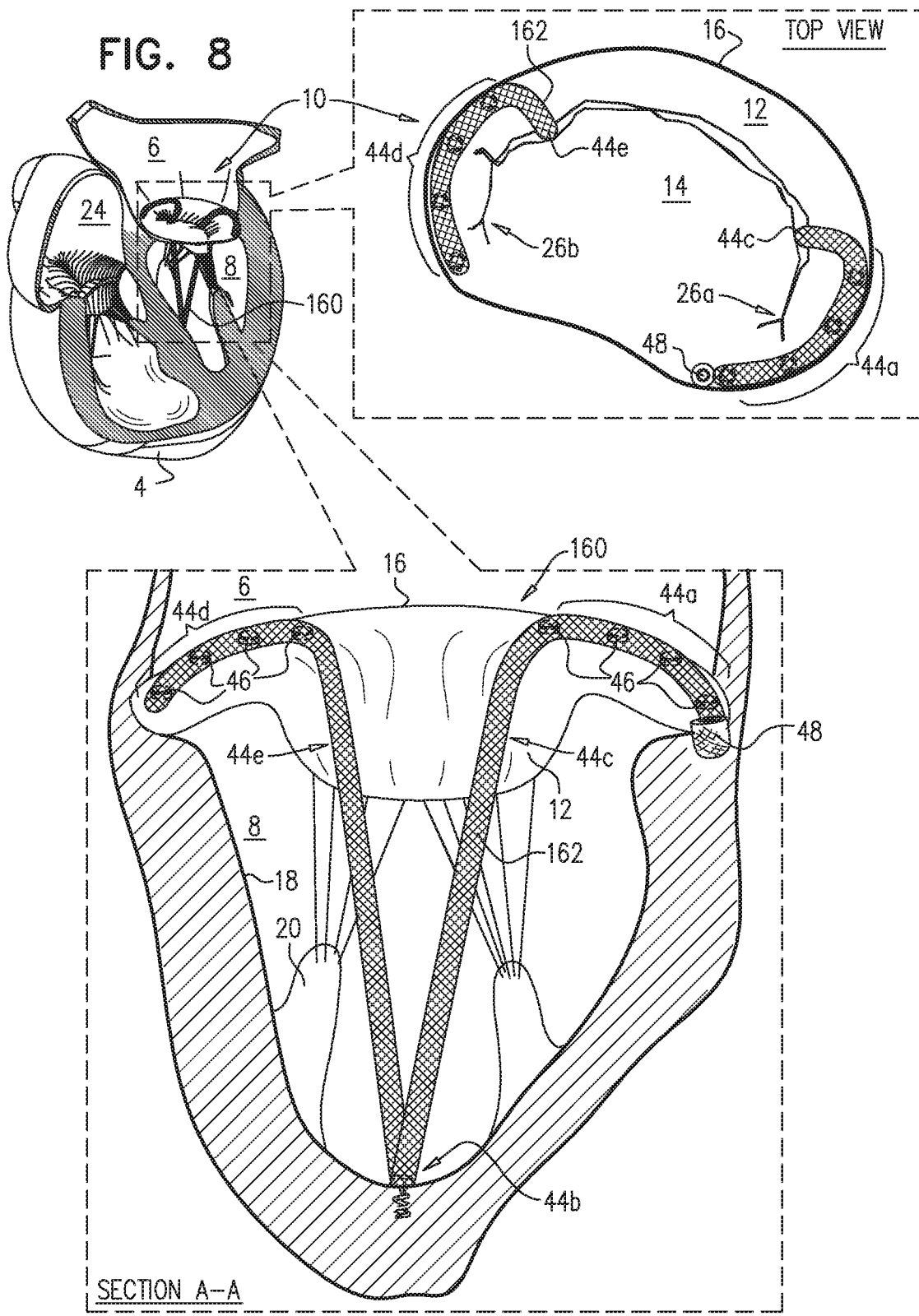
FIG. 8 is a schematic illustration of an implant comprising a flexible longitudinal member, having been implanted at the native valve, in accordance with some applications of the invention.

Reference is made to FIG. 8, which is a schematic illustration of an implant 160 comprising a flexible longitudinal member such as a flexible tubular member 162, having been implanted at native valve 10, in accordance with some applications of the invention. For some applications, implant 160 is identical to implant 40, except that tubular member 162 is longer than tubular member 42. Typically, implant 160 is implanted in the same way that implant 40 is implanted, mutatis mutandis.

Portions 44a and 44d of tubular member 162 is anchored to atrial tissue (e.g., to annulus 16) such that each of the portions extends from an anterior portion of the atrium (e.g., an anterior portion of annulus 16) past (e.g., around) a respective commissure 26, and to a posterior portion of the atrium (e.g., a posterior portion of the annulus). Typically, more anchors 46 are used to anchor portions 44a and 44d of implant 160, than are used to anchor the same portions of implant 40.

As described with reference to FIG. 7, it is hypothesized that, for some applications, reduction of a dimension of native valve 10 along anterior-posterior axis ax1 of the valve is particularly effective in improving coaptation and/or reducing regurgitation. Implant 160 is implanted such that contraction of portions 44a and 44d of the longitudinal member (e.g., tubular member 162) reduces the dimension of the valve along axis ax1 by contracting portions of the valve in the vicinity of commissures 26.

Such contraction of the longitudinal member may be facilitated by adjusting mechanism 48, e.g., as described with reference to FIGS. 2E-F, mutatis mutandis. For some applications, such contraction contracts the entire longitudinal member, thereby also (e.g., automatically and/or simultaneously) reducing slack in portions 44c and 44e, such as described with reference to FIGS. 2E-F, mutatis mutandis.

For some applications, the contraction of portions 44a and 44d is at least partly distinct and/or independent from contraction of other portions of the longitudinal member. For example, one or more separate adjusting mechanisms may be used to contract portions 44a and 44d. Alternatively or additionally, the longitudinal member itself may be differentially contractible, such as by comprising a contraction-inhibition element, such as a coiled element, disposed at one or more portions of the longitudinal member. For some applications, apparatus and techniques described in US Patent Application Publication 2012/0022644 to Reich et al., entitled "Partially-adjustable annuloplasty structure", which is incorporated herein by reference, may be used to provide such differential contractility.

Figures 9, 10:
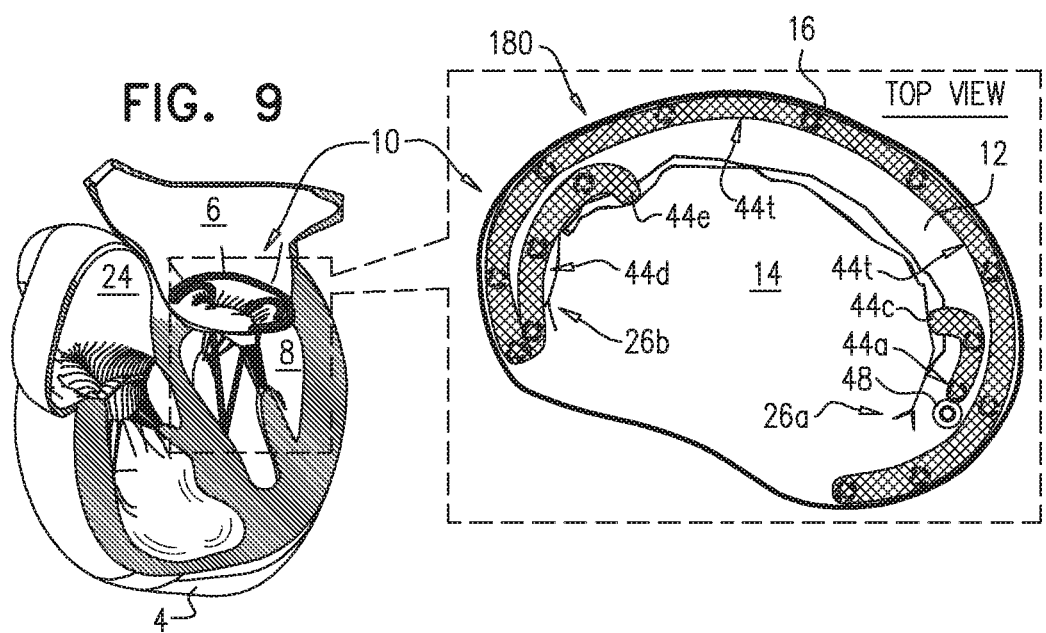
FIG. 9 is a schematic illustration of an implant comprising a flexible longitudinal member, having been implanted at the native valve, in accordance with some applications of the invention.
FIG. 10 is a schematic illustration of an implant comprising a flexible longitudinal member and a plurality of linking members, in accordance with some applications of the invention.

Reference is now made to FIG. 9, which is a schematic illustration of an implant 180 comprising a flexible longitudinal member such as a flexible tubular member 182, having been implanted at native valve 10, in accordance with some applications of the invention. For some applications, implant 180 is identical to implant 40 and/or implant 160, except that tubular member 182 is longer than tubular members 42 and 162. Typically, implant 180 is implanted in the same way that implant 40 is implanted, mutatis mutandis.

Subsequent to anchoring of portions 44a, 44b (not shown in FIGS. 9) and 44d, subsequent portions of tubular member 182 are advanced out of catheter 64 and anchored to annulus 16. For example, as shown in FIG. 9, a portion 44t of member 182 may extend around the posterior side of annulus 16 toward portion 44a. For some such applications, portion 44t defines an annuloplasty portion of member 182.

It is to be noted that for some applications portions of implant 180 are anchored in a different order. For example, portion 44t may be deployed from catheter 64 anchored first.

Reference is made to FIG. 10, which is a schematic illustration of an implant 200 comprising a flexible longitudinal member such as a flexible tubular member 202, and a plurality of linking members 204, in accordance with some applications of the invention. Each linking member 204 extends from a respective first linking site 206a of the longitudinal member to a respective second linking site 206b of the longitudinal member, in accordance with some applications of the invention. FIG. 10 shows implant 200 comprising a first linking member 204a and a second linking member 204b. Linking member 204a extends from a first linking site 206a' to a second linking site 206b', and linking member 204b extends from a first linking site 206a" to a second linking site 206b".

For some applications, linking sites 206 are located such that, when implant 200 is implanted, linking members 204 are located in front of leaflet 12, e.g., such that the leaflet contacts the linking members. It is hypothesized that for some applications, linking members 204 facilitate restraining of leaflet 12 (i.e., inhibition of movement of the leaflet into atrium 6) by inhibiting movement of the leaflet between portions 44c and 44e, such as by inhibiting movement of portions 44c and 44e away from each other, and/or directly obstructing the leaflet.

Typically, implant 200 and techniques for implantation thereof are identical to implant 100 and techniques for implantation thereof, mutatis mutandis, except where noted. For example, (1) in the implanted state (shown in FIG. 10), the distance between each pair of linking sites 206a and 206b, measured along the respective linking member, is smaller than the distance between the linking sites, measured along the longitudinal member (e.g., tubular member 202), e.g., as described with respect to implant 100, mutatis mutandis, whereas (2) in a delivery state, the two distances are typically generally the same.

Figure 11A:
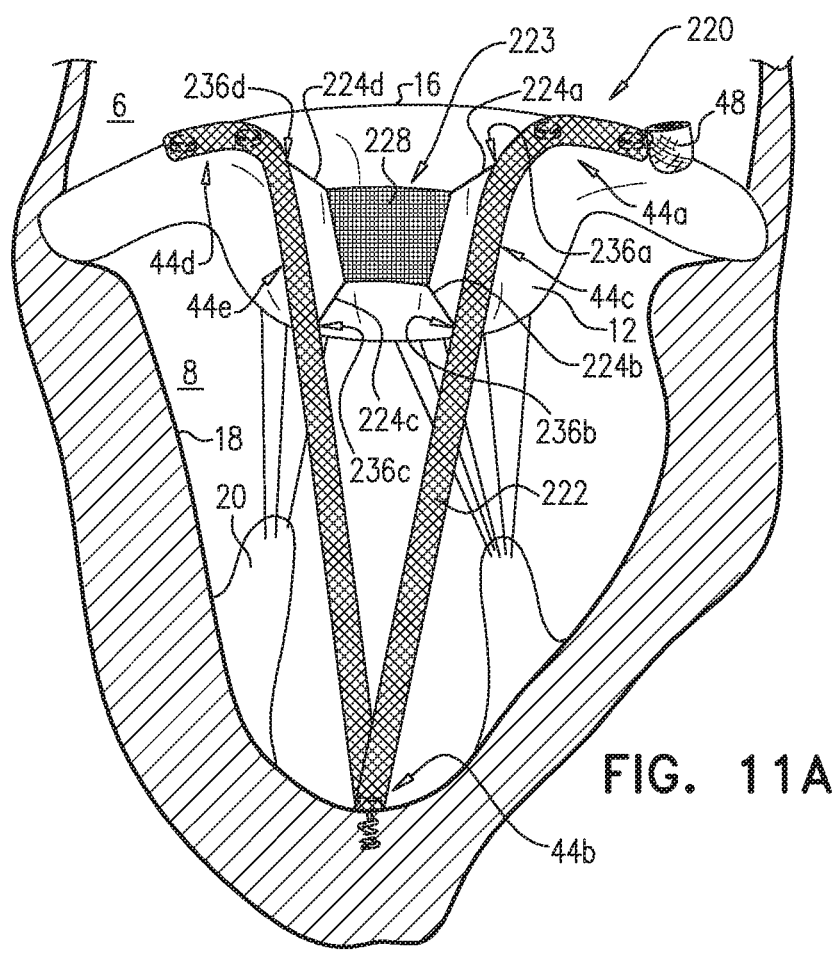
FIGS. 11A-B are schematic illustrations of an implant, comprising a longitudinal member and a harness, in accordance with some applications of the invention.
Figure 11B:
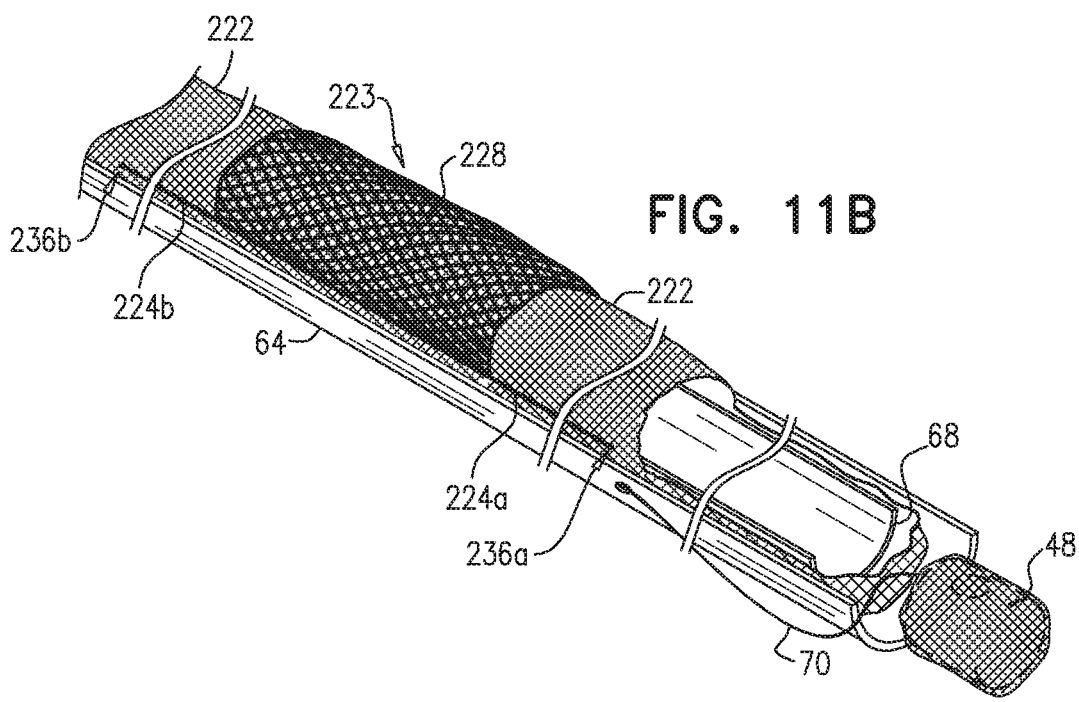

Reference is made to FIGS. 11A-B, which are schematic illustrations of an implant 220, comprising a longitudinal member such as a tubular member 222, and a harness 223, in accordance with some applications of the invention. Harness 223 comprises one or more linking members 224 (e.g., linking members 224a, 224b, 224c, and 224d) and a sheet 228. Linking members 224 extend from respective linking sites 226 (e.g., linking sites 226a, 226b, 226c, and 226d) to sheet 228, and couple the sheet to tubular member 222.

FIG. 11A shows implant 220 in an implanted state. Typically, linking sites 226 are located such that, when implant 220 is implanted, sheet 228 is located in front of leaflet 12, e.g., such that the leaflet contacts the linking members. It is hypothesized that for some applications, harness 223 facilitates restraining of leaflet 12 (i.e., inhibition of movement of the leaflet into atrium 6) by inhibiting movement of the leaflet between portions 44c and 44e, such as by inhibiting movement of portions 44c and 44e away from each other, and/or directly obstructing the leaflet. Sheet 228 provides a larger leaflet-contacting surface compared to linking members alone, and it is hypothesized that for some applications, this advantageously reduces a likelihood of damaging the leaflet being restrained. For some applications, it is hypothesized that sheet 228 may serve as a partial prosthetic valve leaflet.

FIG. 11B shows implant 220 in a delivery state within catheter 64. Typically, sheet 228 is disposed between tubular member 222 and the inner surface of catheter 64, further typically within 2 mm (e.g., within 1 mm) of the tubular member (e.g., in contact with the tubular member). For some applications, sheet 228 is wrapped at least partway around tubular member 222. As described hereinabove for other implants, for one or more of the linking members, the length of the linking member disposed outside of the tubular member is reduced subsequently to deployment from catheter 64.

Reference is now made to FIGS. 12A-C, 13A-B, 14, 15A-B, and 16, which are schematic illustrations of implants each comprising a support structure and a leaflet-restraining frame, in accordance with some applications of the invention.

Figure 12C:
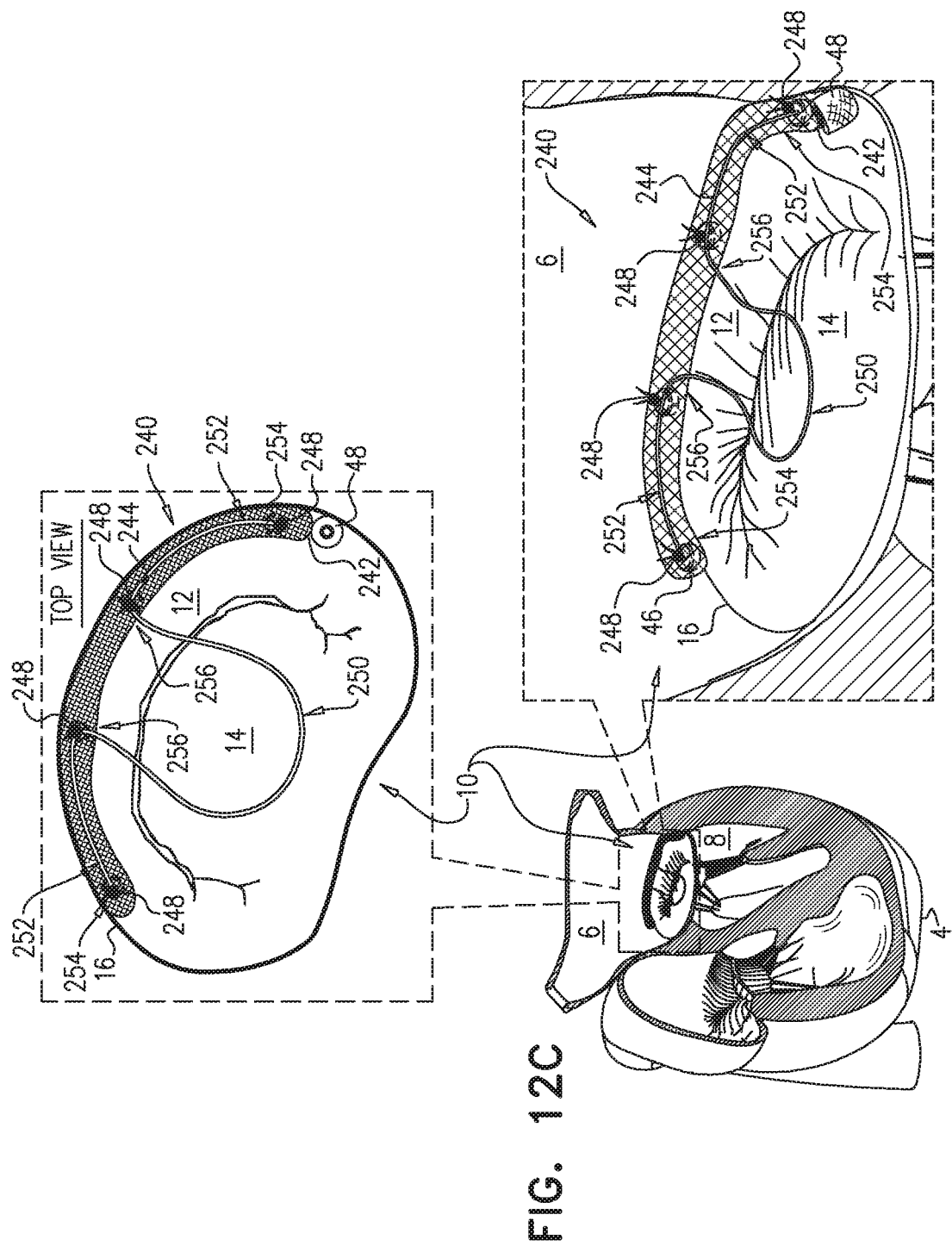

FIGS. 12A-C are schematic illustrations of an implant 240 comprising a support structure 242 and a leaflet-restraining frame 244, in accordance with some applications of the invention. Typically, support structure 242 is (or comprises) a tubular member, e.g., similar to one or more of the tubular members described hereinabove, mutatis mutandis. Support structure 242 is typically anchored to annulus 16 of the valve such that the support structure assumes an arc defining an arc segment 243 disposed at least partway over the orifice and leaflets of the valve. For some applications, support structure 242 is anchored to annulus 16 as described for the tubular members described hereinabove, mutatis mutandis. For some applications, support structure 242 serves as an annuloplasty band, and for some such applications the support structure is adjustable (e.g., comprises adjusting mechanism 48), as described hereinabove, mutatis mutandis.

FIG. 12A shows support structure 242 having been anchored to annulus 16 of native valve 10. The distal end of one or more guide members 246 is coupled, at a respective one or more coupling sites 247, to support structure 242, and remains coupled to the support structure after the anchoring of the support. Guide members 246 extend proximally from the support structure (e.g., into catheter 64, and typically out of the body of the subject). The lumen of the tubular member of support structure defines a longitudinal axis of the tubular member, and as shown in FIGS. 12A-B, guide members 246 typically extend laterally from the tubular member. Guide members 246 may be coupled to support structure 242 itself (e.g., to the tubular member) and/or directly to anchors 46 that anchor the support structure. For applications in which guide members 246 are coupled to support structure 242 itself (as opposed to being coupled directly to anchors 46), the guide members may be coupled to the support structure more than 0.2 cm (e.g., more than 0.5 cm, such as more than 1 cm) and/or less than 10 cm (e.g., less than 5 cm, such as less than 2 cm), e.g., 0.2-10 cm (such as 0.5-5 cm) from the closest anchor 46.

Guide members 246 provide guidance for leaflet-restraining frame 244, which is subsequently advanced along the guide members to the support structure (FIG. 12B). That is, frame 244 is slidably coupled to guide members 246, e.g., via eyelets defined by the frame. Leaflet-restraining frame 244 is typically transluminally advanced while in a delivery state (e.g., a constrained and/or generally straight state), and transitions (e.g., automatically) into a working state (e.g., an expanded state) upon deployment from catheter 64 into atrium 6. To facilitate this, frame 244 is typically resilient, e.g., comprising a shape-memory material.

Subsequently, leaflet-restraining frame 244 is secured to support structure 242, and typically guide members 246 are decoupled from the support structure and removed from the subject (FIG. 12C). For some applications, a locking element 248 is advanced over each guide member, and locked to a distal portion of the guide member before a proximal portion of the guide member (e.g., most of the guide member) is decoupled and removed from the subject. For some such applications, frame 244 is secured to support structure 242 at coupling sites 247.

After implantation (i.e., while support structure 242 is anchored to the annulus and frame 244 is secured to the support structure), leaflet-restraining frame 244 defines a leaflet-restraining portion 250 that extends away from support structure 242 and at least partway across the atrial side of the orifice of the valve (e.g., over one or more of the valve leaflets). Portion 250 inhibits atrially-directed movement of the one or more leaflets (i.e., movement into atrium 6) (e.g., during ventricular systole), thereby treating leaflet prolapse.

Portion 250 typically does not inhibit ventricularly-directed movement of the one or more leaflets (e.g., during ventricular diastole). Typically, and as shown, portion 250 does not extend ventricularly past the valve (i.e., past the leaflets and into ventricle 8).

Portion 250 thereby experiences an atrially-directed force during ventricular systole, as the leaflets are pushed atrially. Resistance to this atrially-directed force is typically provided by force-distribution portions 252 of frame 244, portions 254 of support structure 242 to which portions 252 are coupled, and the tissue anchors that anchor portions 252 and 254 to annulus 16.

For some applications, the coupling of frame 244 to the annulus via structure 242 and anchors 46 is such that, when the native leaflets apply the atrially-directed force to portion 250, portions 254 also experience the force, which is transferred via fulcrum sites 256 at which the leaflet-restraining frame meets support structure 242. For example, support structure 242 may serve as a fulcrum via which force applied to leaflet-restraining portion 270 by atrially-directed movement of leaflet 12 and/or 14 is transferred into a pulling force applied to tissue of the native valve (e.g., annulus 16) by portions 252 and/or 254, via anchors 46. It is hypothesized that such a configuration advantageously distributes load over implant 240 and the tissue to which it is coupled.

For some applications, and as shown, portion 250 generally defines an arc that extends away from and back to support structure 242, e.g., oriented in the opposite direction to the arc defined by the support structure. For some applications portion 250 (e.g., the arc defined thereby) defines a perimeter of more than 2 cm and/or less than 15 cm (e.g., 2-15 cm, e.g., 3-10 cm, such as 4-6 cm). For some applications, and as shown, frame 244 as a whole is serpentine, e.g., curving in a first direction to form a first force-distribution portion 252, curving in a second, opposite, direction to form leaflet-restraining portion 250, and curving back in the first direction to form a second force-distributing portion 252.

Figure 13A:
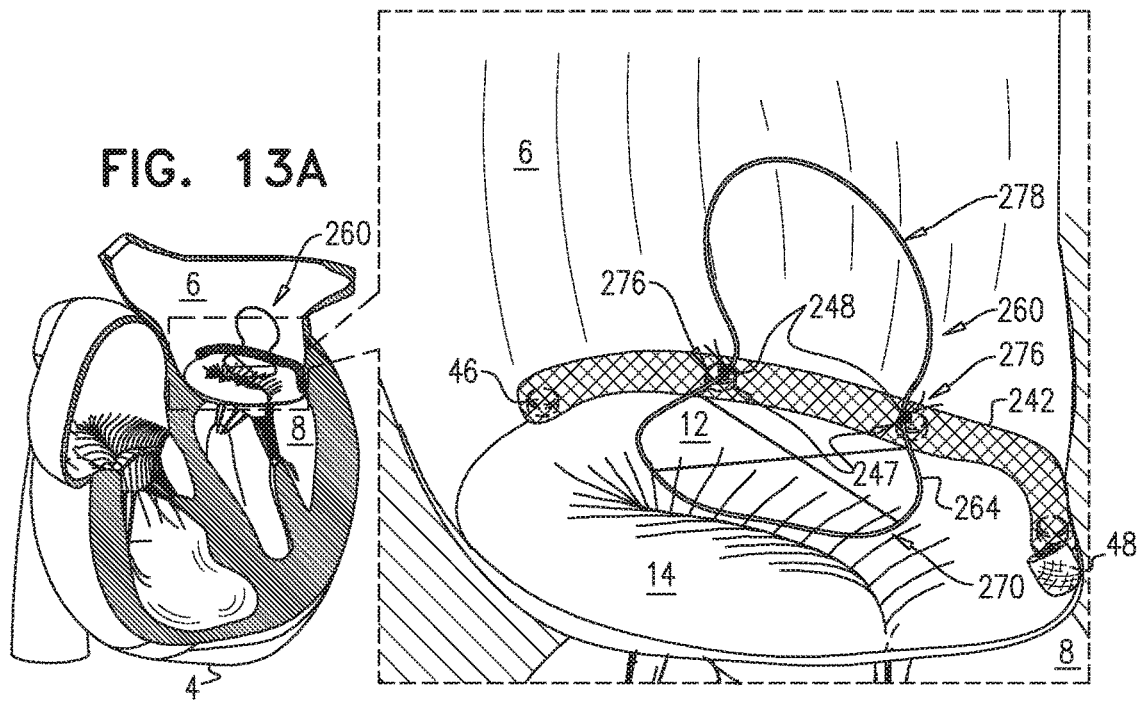

FIGS. 13A is a schematic illustration of an implant 260 comprising support structure 242 and a leaflet-restraining frame 264, in accordance with some applications of the invention. Implant 260 is typically implanted in the same manner as implant 240, mutatis mutandis. In addition to a leaflet-restraining portion 270, which is typically identical to portion 250 of implant 240, leaflet-restraining frame 264 further comprises a force-distributing portion 278 that extends away from support structure 242 and from portion 270 (e.g., extending away from structure 242 in the opposite direction to portion 270). Portion 278 typically contacts tissue of atrium 6, such as the atrial wall. The atrially-directed force experienced by portion 270 presses portion 278 against the tissue, and portion 278 thereby provides resistance to the atrially-directed force. The atrially-directed force is typically transferred via fulcrum sites 276 at which frame 264 is coupled to structure 242. Thus, support structure 242 may serve as a fulcrum via which force applied to leaflet-restraining portion 270 by atrially-directed movement of leaflet 12 and/or 14 is transferred into a pressing force of force-distribution portion 278 against the atrial wall. Typically, coupling sites 247 are disposed between portions 270 and 278, and fulcrum sites 276 generally coincide with the coupling sites.

For some applications, and as shown, portion 278 generally defines an arc that extends away from and back to support structure 242. For some applications portion 278 (e.g., the arc defined thereby) defines a perimeter of more than 2 cm and/or less than 20 cm (e.g., 2-20 cm, e.g., 4-15 cm, such as 5-10 cm).

Figure 13B:
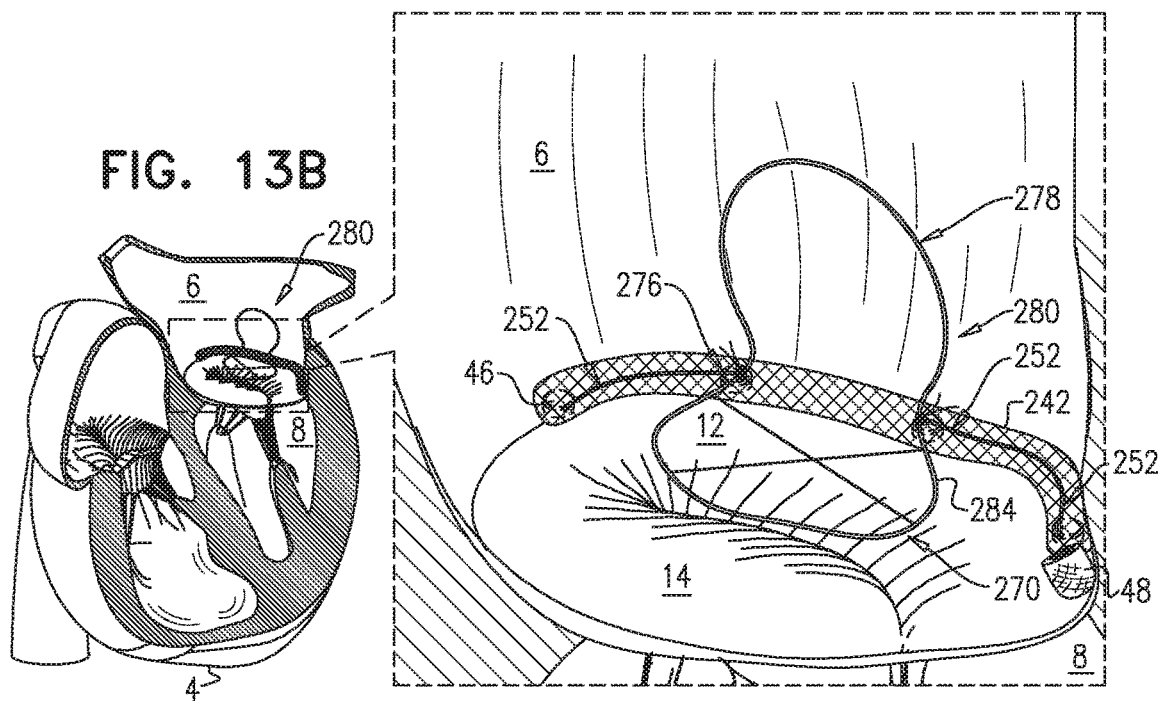

FIG. 13B is a schematic illustration of an implant 280 comprising support structure 242 and a leaflet-restraining frame 284, in accordance with some applications of the invention. Leaflet-restraining frame 284 comprises leaflet-restraining portion 270, force-distribution portion 278, and force-distribution portions 252. For some applications, implant 280 is a combination of implants 240 and 260.

FIG. 14 shows an implant 300 comprising support structure 302 and a leaflet-restraining frame 304, in accordance with some applications of the invention. Typically, support structure 302 is (or comprises) a tubular member, e.g., similar to one or more of the tubular members described hereinabove, mutatis mutandis. Support structure 302 is typically anchored to annulus 16 in the same way as support structure 242, mutatis mutandis. For some applications, support structure 302 serves as an annuloplasty band, and for some such applications the support structure is adjustable (e.g., comprises adjusting mechanism 48), as described hereinabove, mutatis mutandis.

Box A of FIG. 14 shows support structure 302 having been anchored to annulus 16. A guide member 306 extends longitudinally through at least part of the lumen of the tubular member and away from the tubular member. For example, and as shown in FIG. 14, a distal end of member 306 may be disposed within the lumen of the tubular member (e.g., coupled therein) and extend out of a proximal end 301 of the tubular member, and into catheter 62. For some applications, the distal end of member 306 is coupled to the tubular member (e.g., inside the tubular member) at a distal end 303 thereof. (The distal and proximal ends of the tubular member are defined by the direction in which support structure 302 is transluminally advanced; distal end 303 is disposed distally to proximal end 301 during distal advancement of the support structure.)

Guide member 306 extends distally from through the lumen of a first section 310 of the tubular member, out through the wall of the tubular member, alongside a second portion 312 of the tubular member, and back in through the wall. Thereby a portion 308 of guide member 306 is disposed outside and alongside the tubular member. Guide member 306 typically extends further distally through the lumen of a third section 314 of the tubular member.

Typically, guide member 306 is a primary guide member, and a secondary guide member 316, which is tubular, is advanced distally over guide member 306, thereby following the path of guide member 306 (box B of FIG. 14). Subsequently, frame 304 is advanced, in a generally linear delivery state, through a channel defined by guide member 316, typically such that frame 304 follows the same path as guide member 316 (box C of FIG. 14). Typically, (1) the earlier advancement of guide member 316 along guide member 306 is performed such that guide member 306 becomes disposed within the channel defined by guide member 316, and (2) guide member 306 is withdrawn proximally from within the channel prior to advancement of frame 304 through the channel For some applications, guide member 316 defines more than one channel and guide member 306 is not necessarily removed before advancement of frame 304.

For some applications, frame 304 is itself tubular. For some such applications, frame 304 is advanced over guide member 316 subsequently to the advancement of guide member 316 along guide member 306. For some such applications, frame 304 and guide member 316 are advanced over guide member 306 simultaneously while disposed coaxially with respect to each other (e.g., guide member 316 disposed within frame 304, or vice versa).

Subsequently to the advancement of frame 304 through at least part of the lumen of the tubular member of support structure 302, guide member 316 is withdrawn proximally. Frame 304 comprises an elastic material (e.g., a shape-memory material such as, but not limited to, Nitinol or stainless steel), and automatically transitions into its working state upon withdrawal of guide member 316. That is, guide member 316 serves as a retainer that retains frame 304 in its delivery state until the guide member is withdrawn. When frame 304 transitions into its working state, a leaflet-restraining portion 318 of the frame moves away from portion 312 of the tubular member, typically assuming a position with respect to the tubular member and the native valve as described hereinabove with respect to leaflet-restraining portion 250 of leaflet-restraining frame 244 described hereinabove, mutatis mutandis. Typically, frame 304 functions as described with respect to frame 244, mutatis mutandis.

Figure 15A:
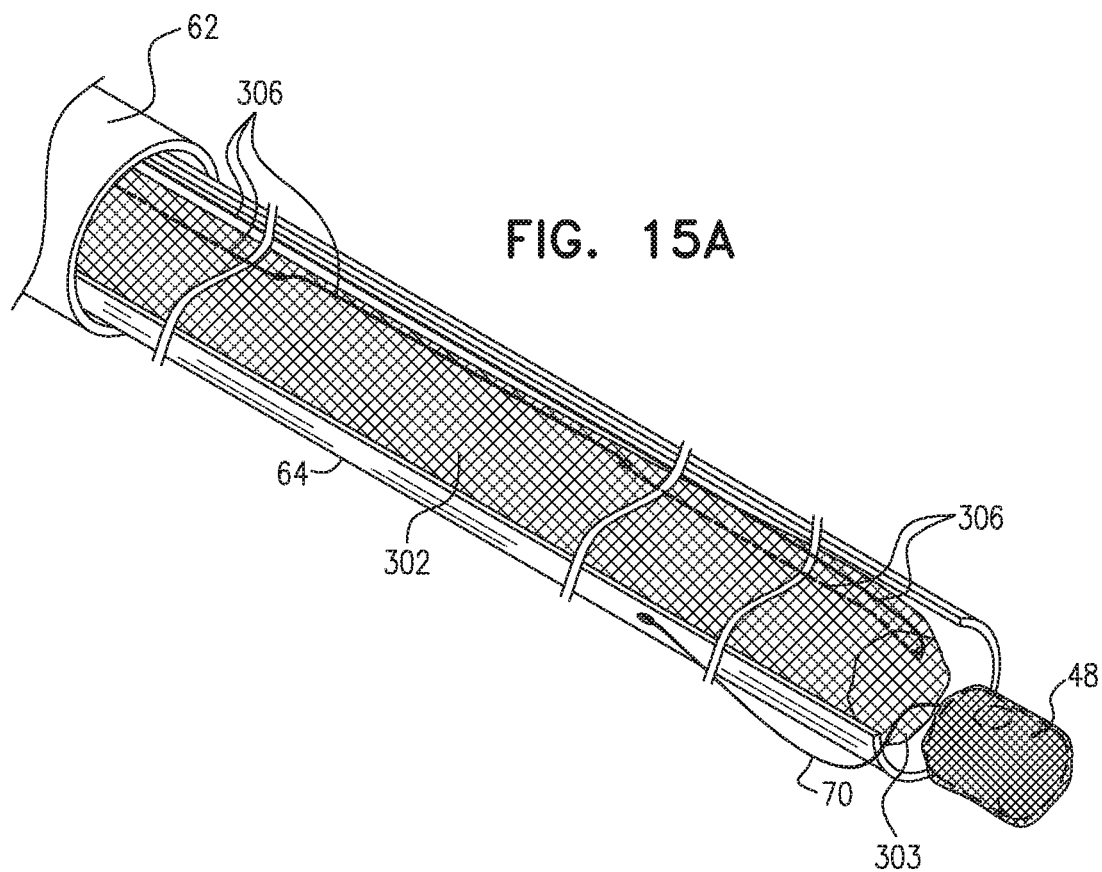
Figure 15B:
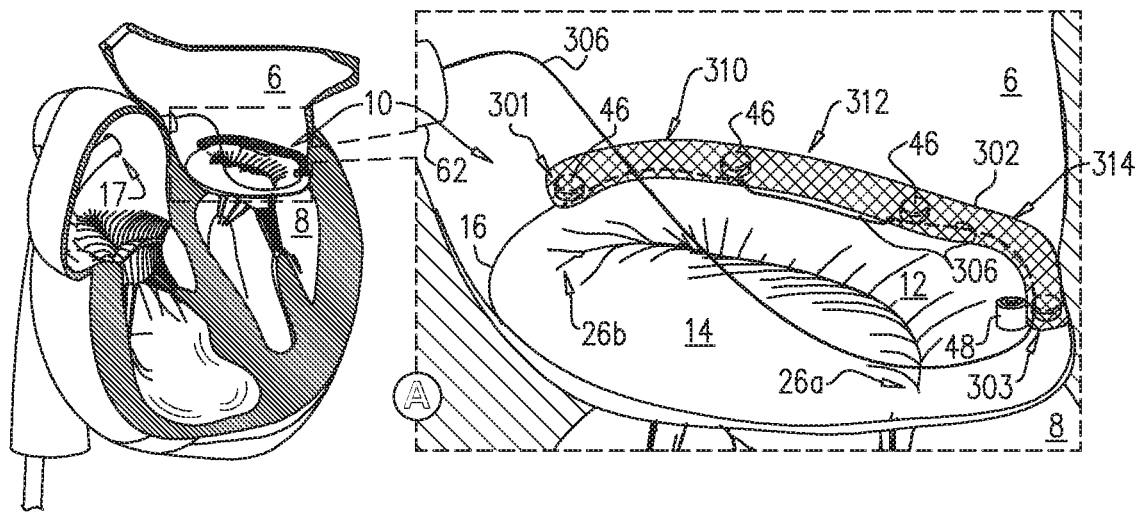

FIGS. 15A-B show implantation of support structure 302 of implant 300, according to some (e.g., some different) applications of the invention. As described hereinabove with reference to FIG. 14, guide member 306 extends longitudinally through at least part of the lumen of the tubular member of support structure 302, and away from the tubular member. For example, and as shown in FIG. 15B, a distal end of member 306 may be disposed within the lumen of the tubular member (e.g., coupled therein) and extend out of distal end 303 of the tubular member, and into catheter 62. For some applications, the distal end of member 306 is coupled to the tubular member (e.g., inside the tubular member) at proximal end 301 thereof.

As explained hereinabove, the distal and proximal ends of the tubular member are defined by the direction in which support structure 302 is transluminally advanced; distal end 303 is disposed distally to proximal end 301 during distal advancement of the support structure. FIG. 15A shows support structure 302 in a delivery state within catheter 64, in accordance with some applications of the invention. As shown in FIG. 15A, for applications in which guide member 306 extends out of distal end 303, support structure 302 is typically configured to be advanced distally through catheter 64 while guide member 306 (1) extends from distal end 303, (2) doubles-back to extend proximally between the tubular member of the support structure and an inner surface of the catheter, and (3) extends proximally away from the support structure.

Distal end 303 is the first part of support structure 302 to be anchored to the valve annulus, and is typically anchored to a portion of the annulus in the vicinity of anterior commissure 26a, as shown. It is hypothesized that this portion of the annulus is more accessible from fossa ovalis 17, e.g., due to the angle at which catheter 62 typically passes the fossa ovalis. It is similarly hypothesized that guide member 306 extending from distal end 303 facilitates advancement of guide member 316 and frame 304 (which are more rigid than guide member 306) by allowing them to be advanced at such an advantageous angle along guide member 306 and into the tubular member of support structure 302.

For some applications, an implantation state similar to that shown in FIG. 15B is achieved by anchoring distal end 303 at a portion of the annulus in the vicinity of anterior commissure 26a, and subsequently anchoring proximal end 301 in the vicinity of posterior commissure 26b. For some such applications, support structure 302 does not comprise adjusting mechanism 48.

Figure 16:
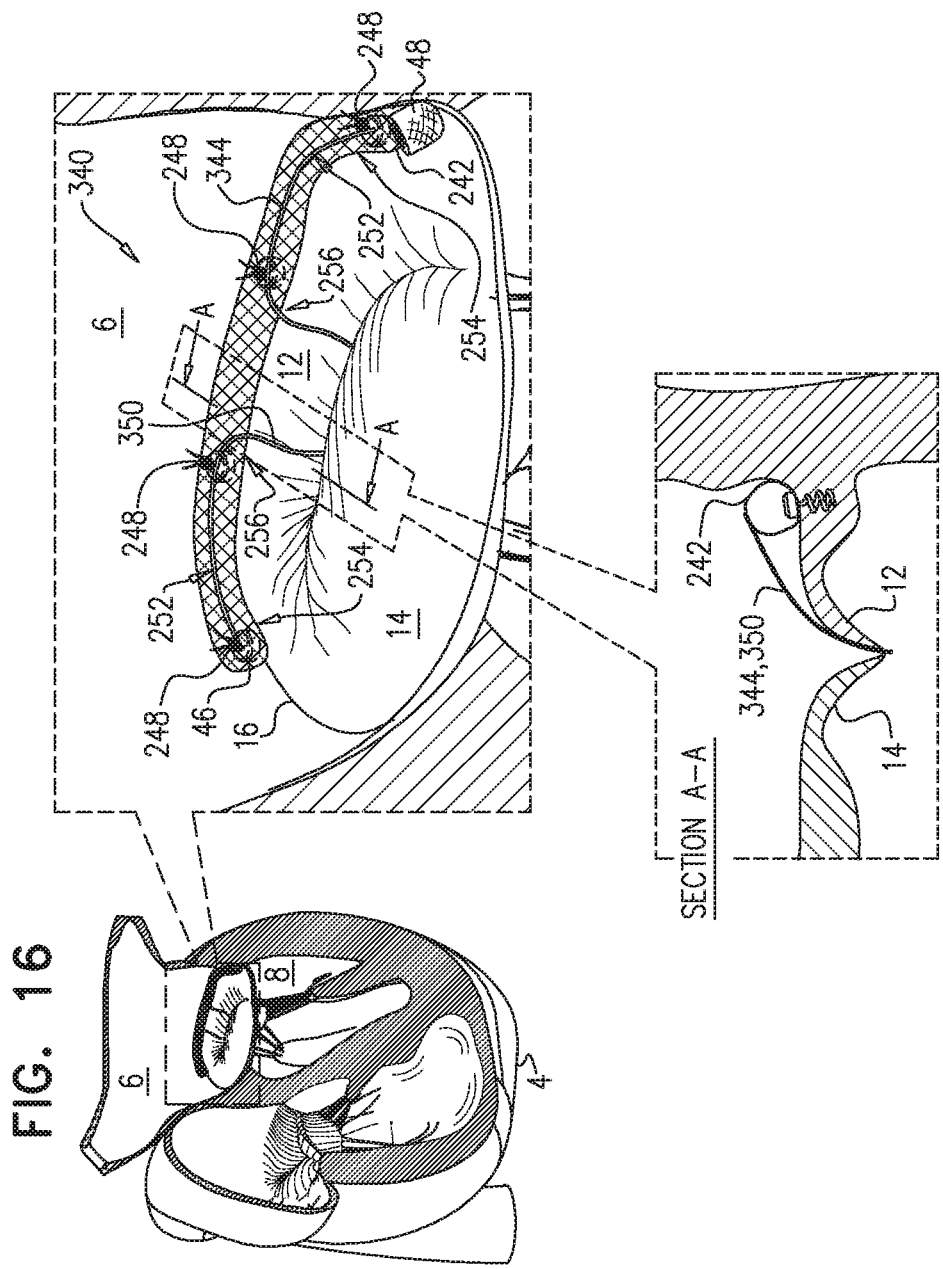

FIG. 16 is a schematic illustration of an implant 340 comprising support structure 242 and a leaflet-restraining frame 344, in accordance with some applications of the invention. Typically implant 340 and components thereof are identical to implant 240 and components thereof, mutatis mutandis, except where noted. Support structure 242 may be replaced with support structure 302, as described with reference to FIGS. 14-15B, mutatis mutandis, and/or implant 340 may be implanted using techniques described with reference to FIGS. 14-15B, mutatis mutandis.

Whereas, after implantation of implant 240, leaflet-restraining portion 250 of leaflet-restraining frame 244 typically does not extend ventricularly past the native valve, after implantation of implant 340, a leaflet-restraining portion 350 of leaflet-restraining frame 344 does extend ventricularly at least a little, such that at least part of portion 350 is disposed between leaflets 12 and 14, e.g., such that during ventricular systole the leaflets sandwich that part of portion 350. Thus, portion 350 defines two coaptation surfaces; one on each side of the portion for a respective leaflet. Typically frame 344 is dimensioned such that portion 350 does not extend deep into ventricle 8. For example, portion 350 may extend less than 1 cm (e.g., 1-10 mm) past the lip of leaflet 12 and/or leaflet 14. It is to be noted that frame 344 is not anchored in the ventricle.

For some applications, portion 350 may be covered in a sheet (e.g., comprising pericardium), e.g., such that portion 350 serves as a partial prosthetic valve leaflet.

Reference is again made to FIGS. 12A-16. It is to be noted that, although implants 240, 260, 280, 300, and 340 are shown being anchored to the posterior side of annulus 16 (i.e., the portion of the annulus in the vicinity of posterior leaflet 12), the scope of the invention includes anchoring the implants to other portions of the annulus (e.g., to the anterior side of the annulus).

It is to be noted that the implants and/or leaflet-restraining frames described with reference to FIGS. 12A-16 may be selected for the dimensions of their leaflet-restraining portions, according to particular circumstances (e.g., anatomy and/or pathology of the subject). For example, it may be desirable that the leaflet-restraining frame extend away from the support structure in the vicinity of the commissures of the native valve, or alternatively closer to the middle scallop of the leaflet.

Figure 17:
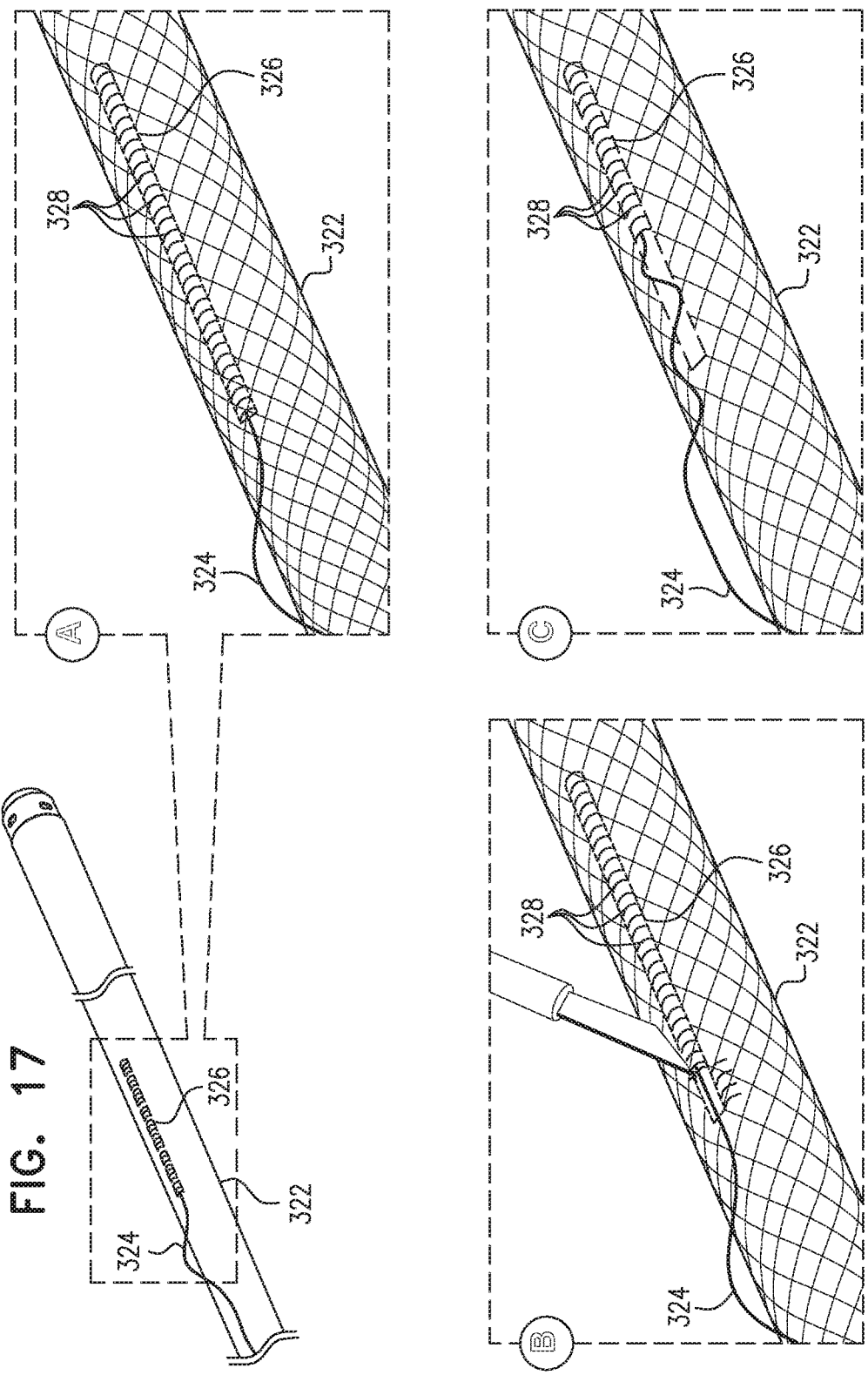
FIG. 17 is a schematic illustration showing adaptation of an implant to a particular subject, in accordance with some applications of the invention.

Reference is again made to FIGS. 5A-F, 6A-B, 7, 10, and 11A-B, and reference is further made to FIG. 17, which is a schematic illustration showing adaptation of an implant to a particular subject, in accordance with some applications of the invention. For some applications, the implant is adapted to the particular subject being treated prior to implantation, based on measurements of the heart valve being treated. For example, the longitudinal member (e.g., the tubular member) may be trimmed. Alternatively or additionally, the location of the linking sites on the tubular member may be adapted. For example, the linking member may be coupled to (e.g., threaded through) the tubular member based at least in part on such measurements. Alternatively or additionally, and as shown in FIG. 17, a linking member 324 may be provided pre-coupled (e.g., pre-threaded) to a tubular member 322 via a slit 326 that is held closed at a plurality of sites by a plurality of stitches 328, which are removed according to the desired location of the linking site. Removal of each stitch progressively increases the effective length of slit 326. (Tubular member 322 and linking member 324 may represent the tubular member and/or linking member of any implant described herein that comprises a tubular member and a linking member.)

Reference is now made to FIG. 18, which is a schematic illustration of an implant 40a comprising a flexible longitudinal member such as flexible tubular member 42 (described hereinabove). Implant 40a is identical to implant 40 (described hereinabove) except that instead of anchors 46, anchors 46a are used. Anchors 46a are dart- or harpoon-anchors. Anchors 46a may be used in place of anchors 46 for any of the implants described herein. Implant 40a is described in order to illustrate that, although helical anchors are shown throughout, for each application of the invention, the scope of the invention includes the use of other types of tissue anchor including, but not limited to, dart- or harpoon-anchors.

Figure 19A:
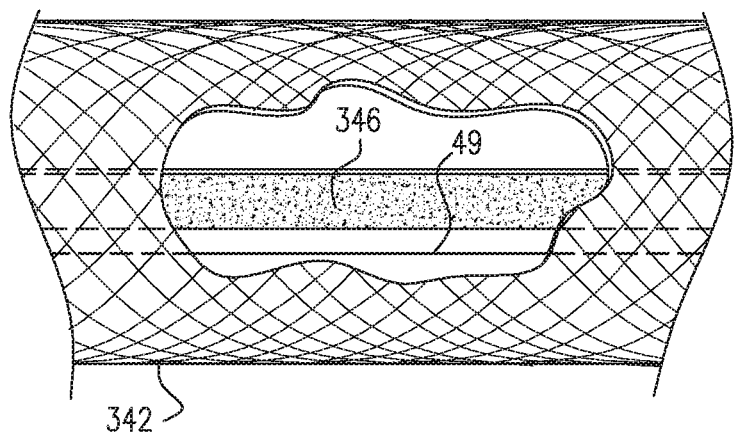
FIGS. 19A-B are schematic illustrations of a resilient strand disposed within at least a portion of a tubular member, in accordance with some applications of the invention.
Figure 19B:
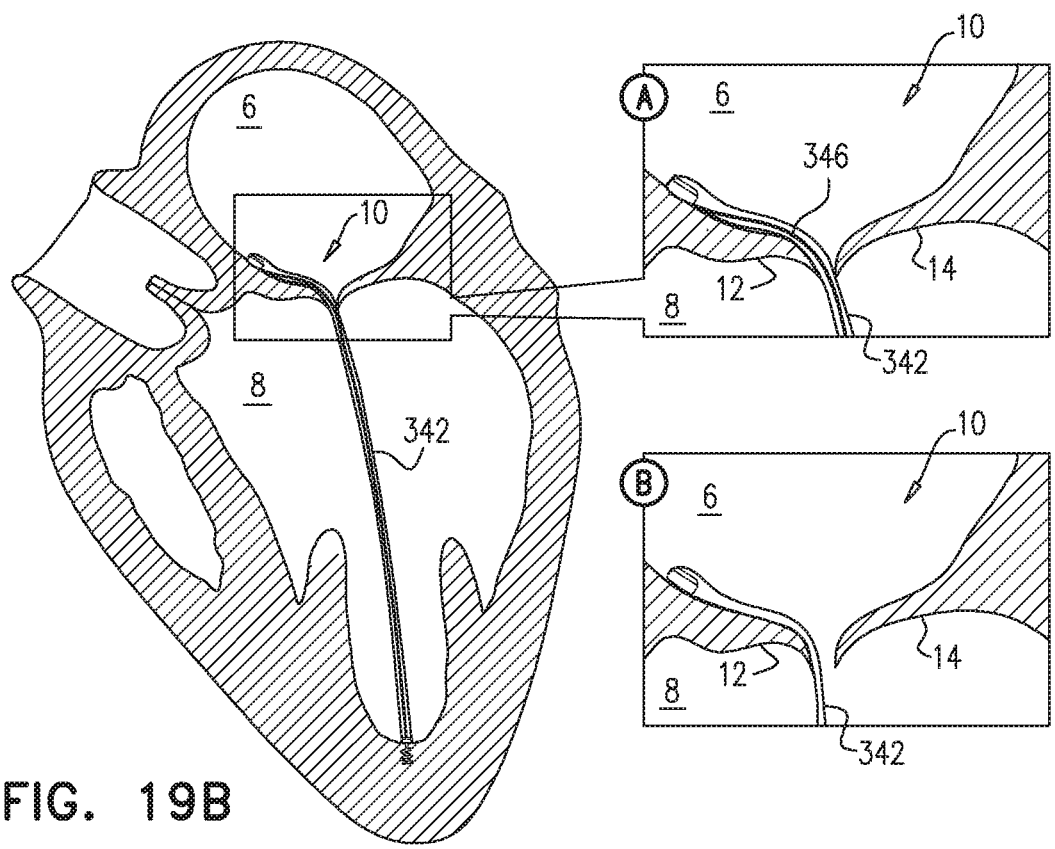

Reference is made to FIGS. 19A-B, which are schematic illustrations of a resilient strand 346 disposed within at least a portion of a tubular member 342, in accordance with some applications of the invention. Strand 346 may be used in combination with implants 40, 80, 100, 120, 140, 160, 180, 200 or 220 (e.g., tubular member 342 may comprise the tubular member of any of those implants). Strand 346 is configured to bias the tubular member toward assuming a particular shape, and as shown, is typically aligned along the portion of the longitudinal member.

Typically, strand 346 is used to control the position of the portion of tubular member 342 that traverses the native valve, so as to improve coaptation of the native leaflets. For example, as shown in FIG. 19B, strand 346 may be used to increase the curvature of a portion of tubular member 342, such that the native leaflet that is restrained by the tubular member is able to move sufficiently upstream during ventricular systole such that leaflet coaptation occurs. In FIG. 19B, tubular member 342 in the presence of strand 346 is shown in frame A, and tubular member 342 in the absence of strand 346 is shown in frame B. It is to be noted that in both cases the atrial and ventricular anchoring sites are the same.

For some applications, strand 346 is disposed at least in the portion of tubular member 342 in which a linking site (described hereinabove) is disposed. For some applications, strand 346 is disposed at least in the portion of tubular member 342 that traverses the native valve.

For some applications, the implant is provided with strand 346 already disposed therewithin. For some applications, strand 346 is introduced into the tubular member during or after implantation.

Figure 20:
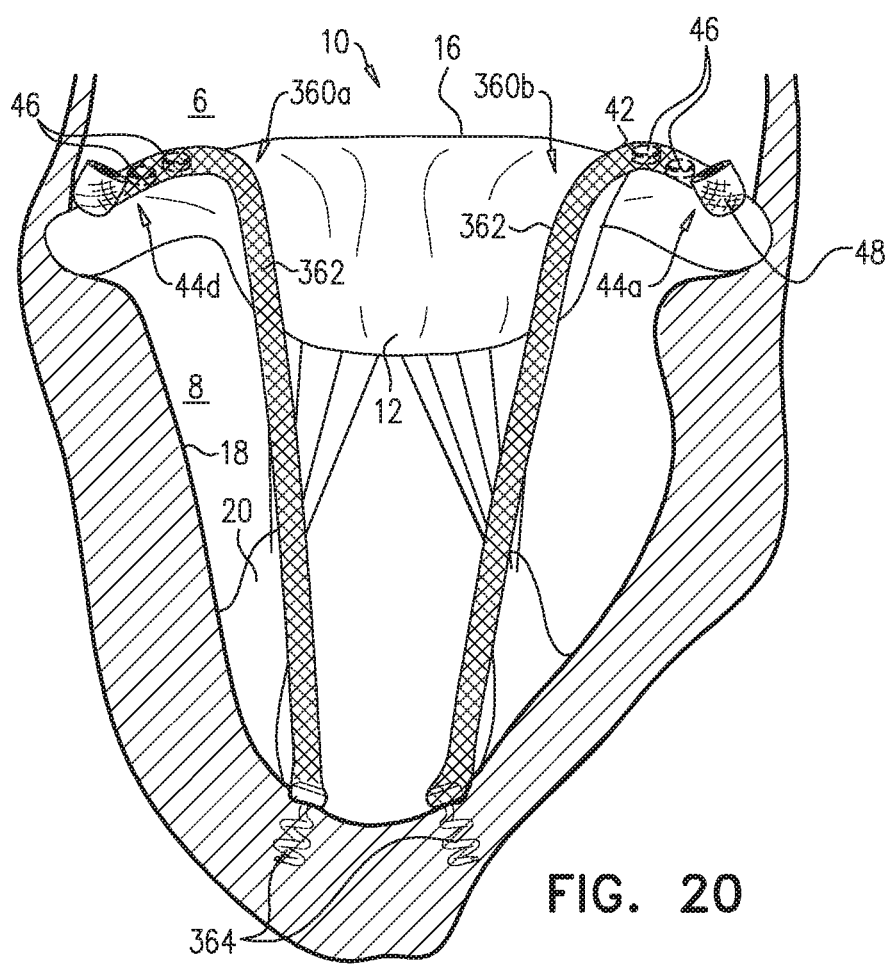
FIG. 20 is a schematic illustration of two implants, each comprising a respective flexible longitudinal member, having been implanted at the native mitral valve, in accordance with some applications of the invention.

Reference is made to FIG. 20, which is a schematic illustration of two implants 360 (e.g., an implant 360a and an implant 360b), each comprising a respective flexible longitudinal member such as a flexible tubular member 362, having been implanted at the native mitral valve, in accordance with some applications of the invention.

Described hereinabove are several embodiments in which a longitudinal member (e.g., a tubular member) is implanted so as to have multiple valve-traversing portions. For some applications, rather than a single longitudinal member being implanted in a back-and-forth pattern, multiple implants are implanted, each having a single valve-traversing portion. The implantation technique is typically the same as described hereinabove, mutatis mutandis. However it is to be noted that typically a distal portion of the longitudinal member is anchored in ventricle 8, rather than in atrium 6. For some applications, this is advantageous, e.g., by facilitating the use of an enlarged (e.g., wider) tissue anchor 364 within the ventricle, which is hypothesized to advantageously improve anchoring of the implant. In this context, the term "enlarged" means larger (typically wider) than other tissue anchors used to anchor the implant (e.g., tissue anchors 46). Moreover, this typically refers to the tissue-engaging portion of the anchor (i.e., the portion that anchors the anchor to tissue). The use of an enlarged tissue anchor is described in more detail with respect to FIGS. 21 and 22.

It is also to be noted that for such applications, adjusting mechanism 48 is typically disposed at a proximal end of each implant 360, and therefore is advanced out of catheter 64 subsequently to the proximal end of the longitudinal member (e.g., the tubular member).

Figure 22:
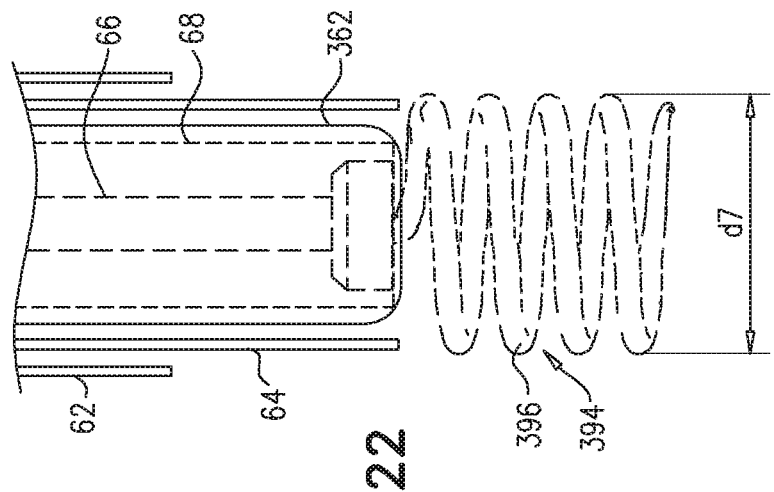
FIGS. 21 and 22 are schematic illustrations of enlarged tissue anchors, in accordance with some applications of the invention.
Figure 21:
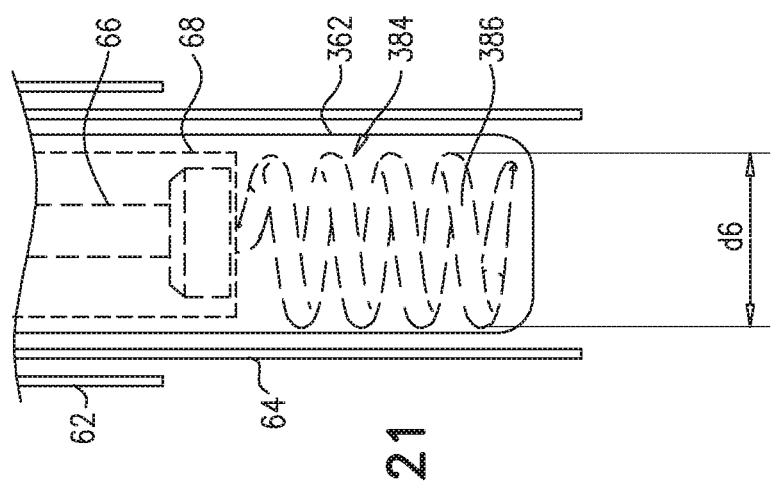

Reference is now made to FIGS. 21 and 22, which are schematic illustrations of enlarged tissue anchors, in accordance with some applications of the invention. FIG. 21 shows an enlarged tissue anchor 384 having a tissue-engaging portion 386, and FIG. 22 shows an enlarged tissue anchor 394 having a tissue-engaging portion 396. For each of these tissue anchors, a diameter of the tissue-engaging portion is greater than a corresponding diameter of the tissue-engaging portion of anchor 46.

Diameter d6 of tissue-engaging portion 386 of tissue anchor 384 is greater than an internal diameter of channel 68 (via which anchors 46 are advanced by anchor manipulator 66). When using tissue anchor 384, implant 360 (comprising tubular member 362) is advanced through catheter 62 while (i) tubular member 362 is disposed within catheter 64, (ii) manipulator 66 extends through channel 68 and is coupled to the anchor, and (iii) at least tissue-engaging portion 386 of anchor 384 is disposed outside of a distal end of channel 68, typically within tubular member 362, e.g., in a space between the distal end of channel 68 and the distal wall of the tubular member. Because anchor 384 is the first anchor to be used, it can be advanced in this manner, ahead of channel 68 (rather than through the channel), and therefore can be wider than the lumen of the channel FIG. 21 shows the implant already having been advanced slightly out of the distal end of catheter 62.

Diameter d7 of tissue-engaging portion 396 of tissue anchor 394 is greater than diameter d6, and is also greater than an internal diameter of catheter 64. When using tissue anchor 394, implant 360 (comprising tubular member 362) is advanced through catheter 62 while (i) tubular member 362 is disposed within catheter 64, (ii) manipulator 66 extends through channel 68 and is coupled to the anchor, and (iii) at least tissue-engaging portion 396 of anchor 394 is disposed outside of (a) a distal end of channel 68 (b) the tubular member (e.g., beyond the distal wall of the tubular member), and (c) a distal end of catheter 64. Because anchor 394 is the first anchor to be used, it can be advanced in this manner, ahead of catheter 64 (rather than through catheter 64), and therefore can be wider than the lumen of catheter 64. FIG. 22 shows the implant already having been advanced slightly out of the distal end of catheter 62.

Reference is made to FIGS. 23A-E, which are schematic illustrations of a system for implanting an implant in the heart of a subject, in accordance with some applications of the invention. A tissue anchor 406 comprises a tissue-engaging element 408 that has a distal tip configured to be pushed into tissue of a heart of a subject, and is configured to anchor the tissue anchor to the tissue. Tissue-engaging element 408 is shown as a helical tissue-engaging element, but may be a dart, a harpoon, or another type of tissue-engaging element, e.g., as described hereinabove. A proximal portion of tissue anchor 406 is shaped to define a carabiner 410. That is, anchor 406 comprises a carabiner coupled to a proximal portion of tissue-engaging element

408. Carabiner 410 may or may not be visually similar to a carabiner for use with rope in recreation or industry, but nonetheless comprises a hook or loop portion 412 and a spring-loaded gate portion 414. For some applications, a single loop of material (e.g., metal) forms both portion 412 and the portion 414. Typically, and as shown, gate portion 414 faces generally toward tissue-engaging element 408.

Figure 23A:
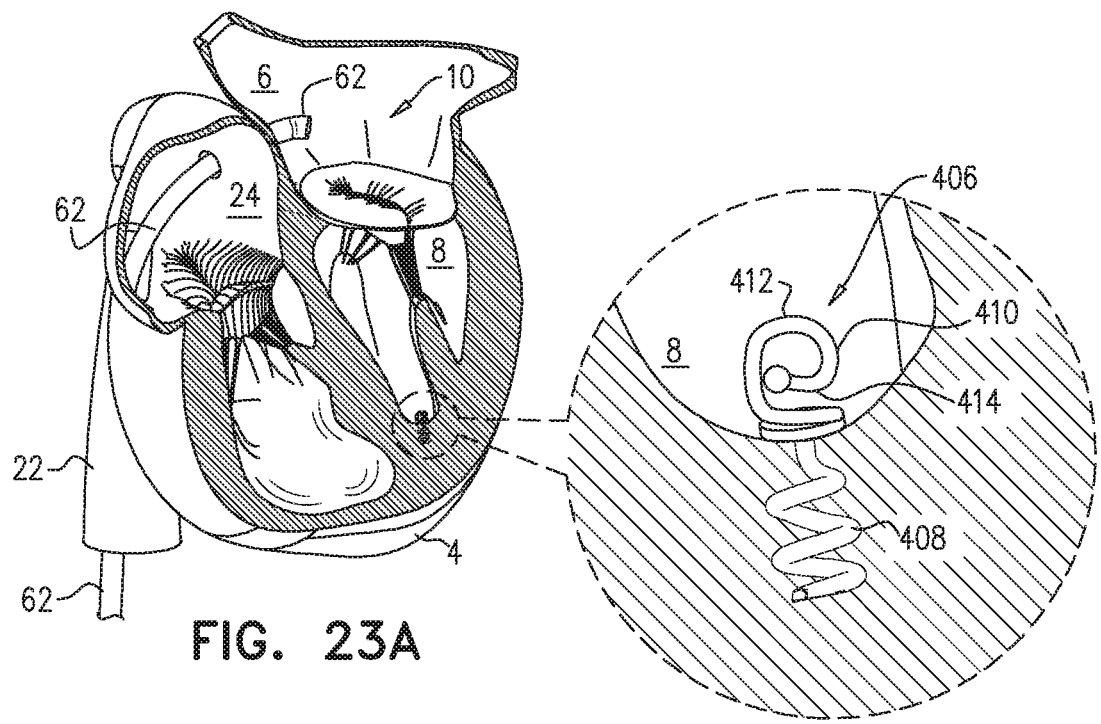
FIGS. 23A-E are schematic illustrations of a system for implanting an implant in the heart of a subject, in accordance with some applications of the invention.
Figure 23B:
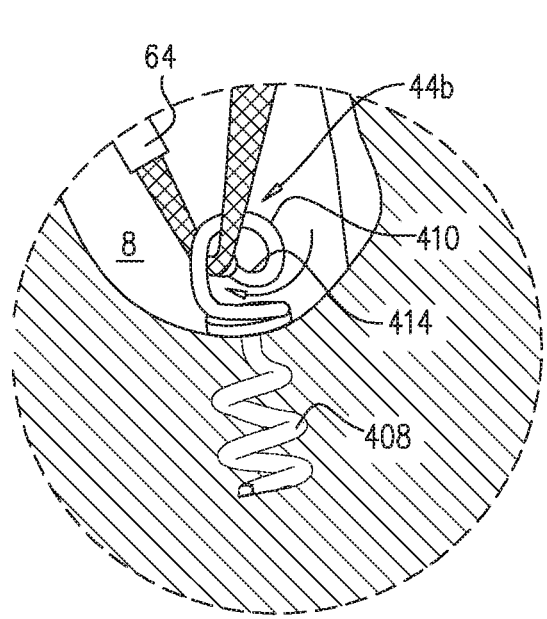
Figure 23C:
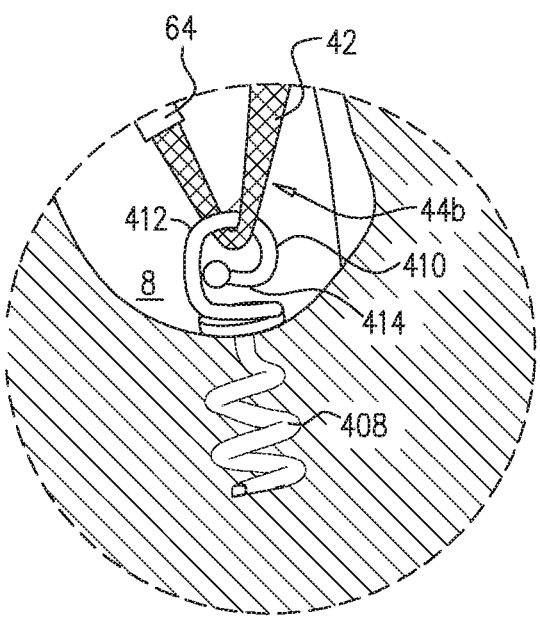
Figure 23D:
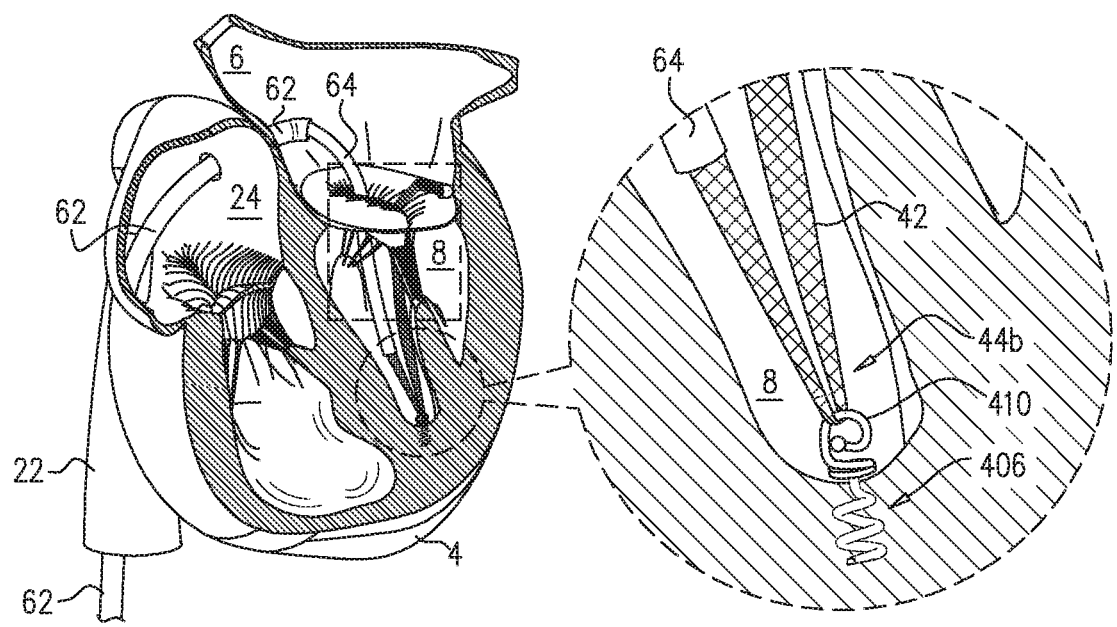
Figure 23E:
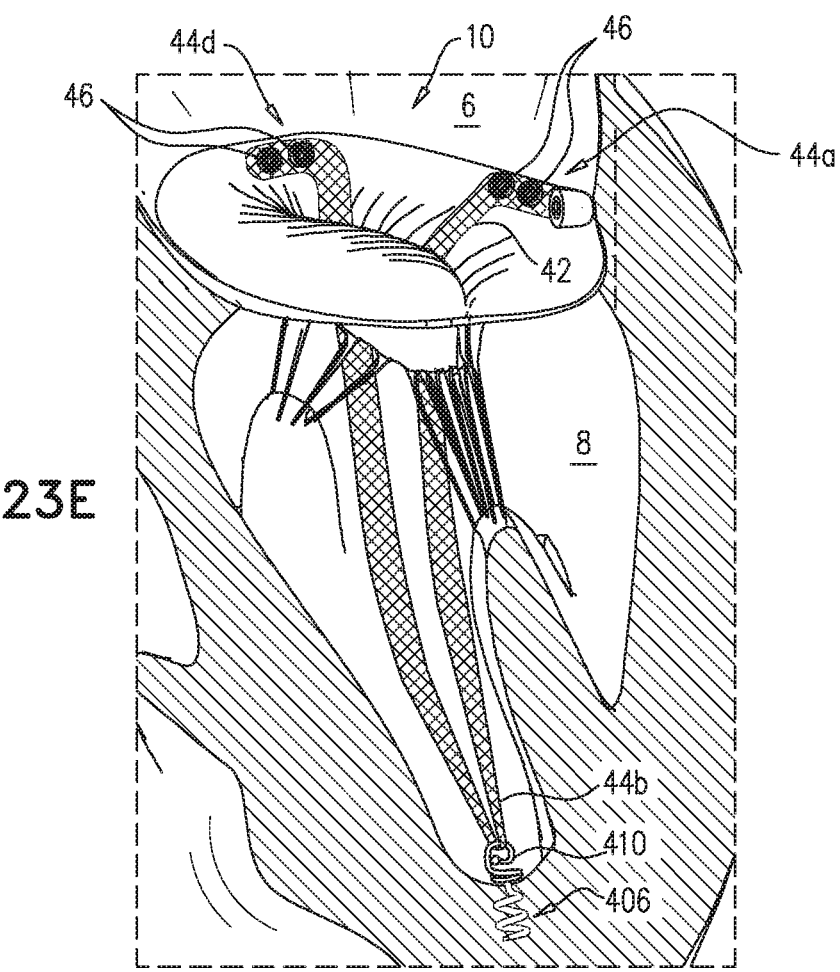

The use of anchor 406 is described with reference to implantation of implant 40, but it is to be understood that anchor 406 may be used to implant other implants described herein, mutatis mutandis. Anchor 406 is typically implanted before implant 40 is advanced toward the heart (e.g., before the implant is introduced into the subject) (FIG. 23A). Typically, anchor 406 is anchored to a ventricular tissue site. Subsequently, implant 40 is introduced, and a first portion of longitudinal member 42 is anchored within atrium 6 (e.g., using anchors 46 as described with reference to FIG. 2A, mutatis mutandis). Subsequently, portions of member 42 are released and drawn into ventricle 8, e.g., as described with reference to FIG. 2B, mutatis mutandis. In contrast to the technique described with reference to FIGS. 2A-G, rather than anchoring portion 44b to the ventricular tissue site by delivering another tissue anchor via channel 68, catheter 64 is used to pull portion 44b through gate portion 414 (typically by drawing portion 44b underneath carabiner 410 and then pulling upward). FIG. 23B shows portion 44b being pulled through gate portion 414, and the gate portion deflecting open responsively. FIG. 23C shows portion 44b having completely entered the carabiner, and gate portion 414 having moved back into its closed position.

Subsequently, more of longitudinal member 42 is exposed as the distal ends of catheter 64 and channel 68 are moved back toward atrium 6 (FIG. 23D), and portion 44e is anchored to a tissue site within the atrium (FIG. 23E), e.g., using anchors 46, as described with reference to FIG. 2D, mutatis mutandis.

Typically, once longitudinal member 42 is coupled to carabiner 410, the longitudinal member is slidable with respect to the carabiner. Therefore the carabiner typically serves as an eyelet. However, because coupling of longitudinal member 42 to anchor 406 does not require a free end of the longitudinal member (as would be required for threading through a closed-ring eyelet), it is also possible, mutatis mutandis, to anchor portions 44a and 44d of the longitudinal member to their respective tissue sites (e.g., atrial tissue sites), and then subsequently coupling portion 44b to the tissue anchor.

It is hypothesized that, for some applications, the slidable coupling provided by carabiner 410 allows difference in tension of different portions of longitudinal member 42 (e.g., generated during its implantation) to even out.

For some applications, rather than a carabiner, an open loop (e.g., a loop that extends in an arc of more than 300 degrees) or a helix may be used at the proximal end of the tissue anchor, and portion 44b may be slidably coupled thereto.

Reference is again made to FIGS. 1A-11B. It is to be noted that, although FIGS. 1A-11B show each longitudinal member (e.g., tubular member) of the implants as having an even number of valve-traversing portions, the scope of the invention also includes longitudinal members having an odd number of valve-traversing portions (e.g., with one end of the longitudinal member anchored in atrium 6, and the other end of the longitudinal member anchored in ventricle 8). It is to be further noted that, for some applications, the longitudinal member has only one valve-traversing portion.

Typically, the contraction of the longitudinal member (e.g., the tubular member) is performed off-pump, while heart structures and/or blood flow are observed using imaging techniques, so as to attain a desired degree of leaflet restraint is provided.

For some applications, the contraction of the longitudinal member reduces a height of ventricle 8, e.g., by reducing a length of one or more of the valve-traversing portions of the longitudinal member. For some such applications, this is achieved by contracting one or more valve-traversing portions of the longitudinal member that have been positioned to traverse the valve at respective commissures 26. It is hypothesized that such positioning reduces obstruction of the native leaflets caused by tensioning of the one or more valve-traversing portions.

Reference is again made to FIGS. 1A-23E. It is to be noted that, although each longitudinal member described herein is shown as a tubular member, the longitudinal member may alternatively be a belt (e.g., a strip of fabric), a cord, or a wire. Furthermore, for applications in which the longitudinal member is a tubular member, it is to be noted that empty portions of the tubular member may assume a generally belt-like shape, e.g., following implantation, e.g., as described with reference to FIG. 7.

For some applications, one or more implants described herein (such as implants 120, 140, 160, 180, 240, 260, 280, 300, and/or 340) provide both annuloplasty functionality and leaflet-restraining functionality.

Typically, the procedures described hereinabove are performed "off-pump", i.e., in the absence of a cardiopulmonary bypass.

For some implants described hereinabove (e.g., implant 100), a linking member is positioned to facilitate restraining of a valve leaflet. For some implants described hereinabove (e.g., implant 120), a linking member is positioned to facilitate annuloplasty. It is to be noted that the scope of the invention includes implants in which at least one linking member is positioned to facilitate restraining of the valve leaflets and at least one linking member is positioned to facilitate annuloplasty.

For some implants described hereinabove, the implant is configured and/or implanted such that a linking member and/or a harness of the implant is generally the only part of the implant that restrains (e.g., significantly) the leaflet of the native valve. For example, the longitudinal member (e.g., the tubular member) may traverse the native valve at the commissures so as to reduce (e.g., prevent) restraint of the native leaflets by the longitudinal member, and such that the longitudinal member serves only as a support for the linking member and/or harness, which restrains the native leaflet.

Typically, the longitudinal members (e.g., tubular members) described hereinabove are longer than longitudinal members (e.g., tubular members) used as partial annuloplasty rings. For example, the longitudinal members may have a length of at least 13 cm (e.g., at least 14 cm, e.g., at least 15 cm, such as at least 18 cm), and/or less than 30 cm (e.g., less than 25 cm, such as less than 22 cm), e.g., 14-25 cm, e.g., 15-25 cm, such as 18-25 cm.

It is to be noted that for applications of the invention that don't include sheet 228, the leaflet-restraining portion(s) of each implant typically cover less than 30 percent (e.g., less than 20 percent, such as less than 10 percent) of the leaflet being restrained. This is therefore in contrast to implanting a prosthetic leaflet over the native leaflet, whereby it would typically be desirable for the prosthetic leaflet to have a large surface area.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for use with a heart of a subject, the apparatus comprising:
   a catheter, transluminally advanceable to the heart;
   an implant, comprising:
      a flexible longitudinal member, and
      a linking member that extends from a first linking site of the longitudinal member to a second linking site of the longitudinal member,
   a plurality of tissue anchors comprising at least a first tissue anchor, a second tissue anchor and a third tissue anchor, each of the tissue anchors being slidable through the catheter, and configured to anchor a respective one of a plurality of portions of the longitudinal member to a respective one of a plurality of locations of tissue of the heart; and
   at least one anchor driver, configured to anchor the plurality of portions of the longitudinal member to the plurality of locations using the plurality of tissue anchors; the anchor driver and the implant being slidable through the catheter and with respect to each other such that:
   a distal portion of the plurality of portions is anchorable to a first location of tissue by the first tissue anchor while the first linking site is disposed within the catheter,
   while (1) the distal portion is anchored to the first location, and (2) the second linking site is disposed within the catheter, a second portion of the plurality of portions is advanceable distally out of the catheter and anchorable to a second location of tissue by the second tissue anchor,
   while the second portion is anchored to the second location, the second linking site and a third portion of the plurality of portions are advanceable distally out of the catheter, and
   after the second linking site has been advanced out of the catheter, the third portion is anchorable to a third location of tissue by the third tissue anchor.

2. The apparatus according to claim 1, wherein:
   the first location of tissue is a location of a first tissue selected from the group consisting of: atrial tissue and ventricular tissue,
   the second location of tissue is a location of a second tissue (1) selected from the group consisting of: atrial tissue and ventricular tissue, and (2) not the first selected tissue, and
   the distal portion of the longitudinal member is configured to be anchored by the first tissue anchor to the location of the first selected tissue, and the second portion of the longitudinal member is configured to be anchored by the second tissue anchor to the location of the second selected tissue.

3. The apparatus according to claim 1, wherein the second portion is disposed 1-6 cm along the longitudinal member from the distal portion.

4. The apparatus according to claim 3, wherein the second portion is disposed 1.5-3 cm along the longitudinal member from the distal portion.

5. The apparatus according to claim 3, wherein the first linking site is disposed 0.5-4 cm along the longitudinal member from the distal portion, and 1-5 cm along the longitudinal member from the second portion.

6. The apparatus according to claim 3, wherein the third portion is disposed 1-6 cm along the longitudinal member from the second portion.

7. The apparatus according to claim 6, wherein the third portion is disposed 1.5-3 cm along the longitudinal member from the second portion.

8. The apparatus according to claim 6, wherein the second linking site is disposed 0.5-4 cm along the longitudinal member from the second portion, and 1-5 cm along the longitudinal member from the third portion.

9. The apparatus according to claim 1, wherein the linking member is elastic.

10. The apparatus according to claim 1, wherein the implant has:
    a delivery state in which (1) the implant is slidable through at least part of the catheter, (2) the longitudinal member is coaxial with the catheter, and (3) at least a portion of the linking member is disposed alongside the longitudinal member, and
    an implanted state in which (1) a first distance between the first linking site and the second linking site, measured along the longitudinal member, is greater than a second distance between the first linking site and the second linking site, measured along the linking member, (2) the linking member has a mid-portion disposed between the first linking site and the second linking site, and (3) the mid-portion is not in contact with the longitudinal member.

11. The apparatus according to claim 10, wherein in the implanted state, the mid-portion is disposed at least 10 mm from the longitudinal member.

12. The apparatus according to claim 10, wherein the portion of the linking member includes the mid-portion of the linking member.

13. The apparatus according to claim 10, wherein in the delivery state, the portion of the linking member that is disposed alongside the longitudinal member is disposed less than 1 mm from the linking member.

14. The apparatus according to claim 13, wherein in the delivery state, the portion of the linking member that is disposed alongside the longitudinal member is in contact with the linking member.

15. The apparatus according to claim 10, wherein the second distance is adjustable by the linking member being slidable with respect to the longitudinal member at at least one of the linking sites.

16. The apparatus according to claim 15, wherein the implant further comprises a locking mechanism, and the second distance is fixable by locking the locking mechanism to the linking member.

17. The apparatus according to claim 16, wherein the locking mechanism comprises a ratcheting mechanism.

18. The apparatus according to claim 1, wherein:
    the flexible longitudinal member is a flexible tubular member, comprising a wall that defines a lumen,
    the linking member extends from the first linking site outside of the tubular member to the second linking site,
    the plurality of tissue anchors are slidable within the lumen of the tubular member, and the anchor driver is slidable within the lumen of the tubular member, and is configured to drive the plurality of tissue anchors from the lumen, through the wall and into the tissue.

19. The apparatus according to claim 18, wherein the wall comprises a lateral wall that circumscribes the lumen and a distal wall that defines a distal end of the lumen, and the apparatus is configured such that (1) at least one tissue anchor of the plurality of tissue anchors is drivable by the anchor driver through the distal wall, and (2) another at least one tissue anchor of the plurality of tissue anchors is drivable by the anchor driver through the lateral wall.

* * * * *